US010017511B2

(12) United States Patent
Sawant et al.

(10) Patent No.: US 10,017,511 B2
(45) Date of Patent: Jul. 10, 2018

(54) PYRAZOLOPYRIMIDINONES FOR THE TREATMENT OF IMPOTENCE AND PROCESS FOR THE PREPARATION THEREOF

(71) Applicant: COUNCIL OF SCIENTIFIC & INDUSTRIAL RESEARCH, New Delhi (IN)

(72) Inventors: Sanghapal Damodhar Sawant, Jammu (IN); Lakshma Reddy Ginnereddy, Jammu (IN); Srinivas Mahesuni, Jammu (IN); Sajad Hussain Syed, Jammu (IN); Mohd Ishaq Dar, Jammu (IN); Amit Nargotra, Jammu (IN); Priya Mahajan, Jammu (IN); Ram Asrey Vishwakarma, Jammu (IN)

(73) Assignee: Council of Scientific & Industrial Research, New Delhi (IN)

(*) Notice: Subject to any disclaimer, the term of this patent is extended or adjusted under 35 U.S.C. 154(b) by 0 days.

(21) Appl. No.: 15/115,573

(22) PCT Filed: Oct. 20, 2014

(86) PCT No.: PCT/IN2014/000662
§ 371 (c)(1),
(2) Date: Jul. 29, 2016

(87) PCT Pub. No.: WO2015/114647
PCT Pub. Date: Aug. 6, 2015

(65) Prior Publication Data
US 2017/0066771 A1    Mar. 9, 2017

(30) Foreign Application Priority Data
Jan. 30, 2014    (IN) .......................... 0281/DEL/2014

(51) Int. Cl.
*A01N 43/90* (2006.01)
*A61K 31/519* (2006.01)
*C07D 487/04* (2006.01)

(52) U.S. Cl.
CPC .......... *C07D 487/04* (2013.01); *A61K 31/519* (2013.01)

(58) Field of Classification Search
None
See application file for complete search history.

(56) References Cited

U.S. PATENT DOCUMENTS 5,958,926 A * 9/1999 Garvey ............... C07D 405/14
514/12.1

FOREIGN PATENT DOCUMENTS

| AU | 2004201386 A1 | 4/2004 | |
| BR | 9803911 | * 3/2000 | ........... A61K 31/505 |
| EP | 1630164 A1 | 3/2006 | |
| EP | 2589601 A1 | 5/2013 | |
| WO | 9954333 A1 | 10/1999 | |
| WO | 013644 A2 | 1/2001 | |
| WO | 015386 A2 | 1/2001 | |
| WO | 0187888 A1 | 11/2001 | |

OTHER PUBLICATIONS

ISA/EP International Search Report and Written Opinion prepared for PCT/IN2014/000662 dated Apr. 2, 2015.
IPRP/EP International Preliminary Examining Authority prepared for PCT/IN2014/000662 dated Feb. 1, 2016.
IPRP/EP Notification of Transmittal of the International Preliminary Report on Patentability prepared for PCT/IN2014/000662 dated Jun. 6, 2016.

* cited by examiner

*Primary Examiner* — Jeffrey H Murray
(74) *Attorney, Agent, or Firm* — Dinsmore & Shohl LLP

(57) ABSTRACT

The present invention relates to Pyrazolopyrimidinone compounds as PDE5 inhibitors with better $IC_{50}$ value, good in vivo efficacy and PK profile and a process for the preparation thereof. The present invention covers the pyrazolo pyrimidinone based compounds that have been designed, synthesized and screened for PDE5 inhibitory activity and its PDE5 inhibitory potential is provided in this invention. These designer compounds have shown nanomolar potency when screened for PDE5 inhibitory activity and also shown better in vivo efficacy. These compounds can be used in the treatment of male erectile dysfunction or in the treatment of impotence.

7 Claims, 7 Drawing Sheets

Figure 1:
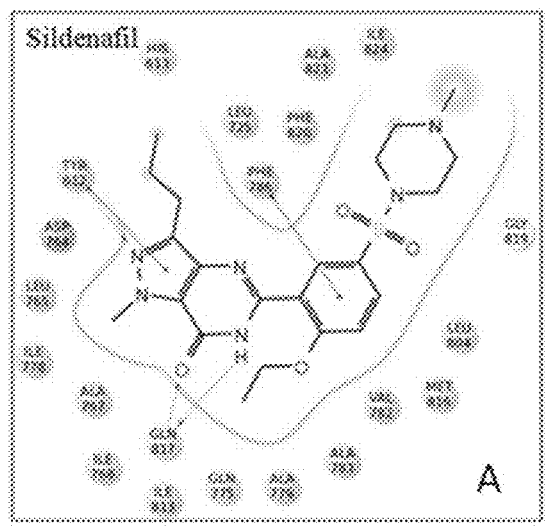
Figure 1:
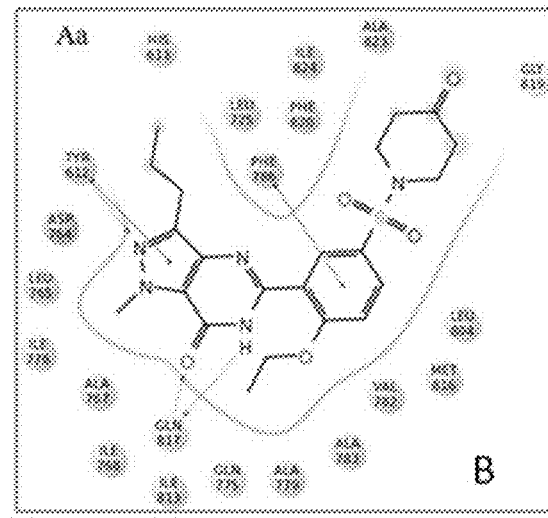

PYRAZOLOPYRIMIDINONES FOR THE TREATMENT OF IMPOTENCE AND PROCESS FOR THE PREPARATION THEREOF

CROSS REFERENCE TO RELATED APPLICATIONS

This application is a 35 U.S.C. 371 national stage filing and claims priority to International Application No. PCT/IN/2014/000662 filed on Oct. 20, 2014, entitled "Pyrazolopyrimidinones for the treatment of impotence and process for the preparation thereof," which claims the benefit of Indian Patent Application No. 0281/DEL/2014 filed on Jan. 30, 2014, each of which is incorporated herein in its entirety by reference.

FIELD OF THE INVENTION

The present invention relates to pyrazolo pyrimidinone based compounds as PDE5 inhibitors for the treatment of impotence. The pyrazolopyrimidinone based compounds have been designed, synthesized and the PDE5 inhibitory potential is provided in this invention. These designer compounds have shown nanomolar potency when screened for PDE5 inhibitory activity. These compounds are having better efficacy and PK profile than the existing PDE5 inhibitors. The use of a cGMP PDE inhibitors and their method of treating a male mammal, including human, to cure or prevent erectile dysfunction comprising effective amount of compound of formula 1 or pharmaceutically acceptable salts thereof or a pharmaceutical composition in provided in this invention. The present invention also relates to the process for the preparation of pyrazolopyrimidinone based compounds.

BACKGROUND OF THE INVENTION

Pyrazolopyrimidinones are very well reported for their PDE5 (Phosphodiesterase) inhibitory activity. The well known drug used for erectile dysfunction is 'Sildenafil', it contains 5-(2-ethoxyphenyl)-1-methyl-3-propyl-1H-pyrazolo[4,3-d]pyrimidin-7(6H)-one as an active ingredient in Viagra.

Phosphodiesterase is an ubiquitous enzyme which selectively catalyzes the hydrolysis of the 3'-cyclic phosphate bonds of adenosine and/or guanosine 3',5'-cyclicmonophosphate into their respective 5'-nucleosidemonophosphates. cAMP (3',5'-cyclic adenosine monophosphate) and cGMP (3',5'-cyclic guanosine monophosphate) are second messengers within cells. These signaling molecules can be generated in two ways. They can carry signals generated by extra-cellular signaling molecules that are incapable of entering the cells. These extracellular signaling molecules, such as hormones or neurotransmitters, bind to membrane bound proteins that in turn activate the particulate forms of adenylate or guanylate cyclase. This activation results in the generation of cAMP or cGMP from adenosine triphosphate (ATP) and guanosine triphosphate (GTP), respectively. Soluble (cytosolic) forms of adenylate and guanylate cyclase also exist and can be activated by messengers within the cell. Soluble adenylate cyclase is activated by calcium signaling to generate cAMP, and soluble guanylate cyclase is activated by nitric oxide (NO) which in turn generates cGMP. The generation and resulting regulation of this signaling are important to many functions throughout the cell. Temporal and spatial regulation of cAMP and cGMP falls to the phosphodiesterases. This is done through the hydrolysis of cAMP and cGMP into their non signaling forms AMP and GMP, respectively (Chappie T. A., Helal C. J., Hou X. *J. Med. Chem.* 2012, 55, 7299-7331).

There are 11 different PDE families, with each family typically having several different isoforms and splice variants. These unique PDEs differ in their three-dimensional structure, kinetic properties, modes of regulation, intracellular localization, cellular expression, and inhibitor sensitivities. Current data suggest that individual isozymes modulate distinct regulatory pathways in the cell. These properties therefore offer the opportunity for selectively targeting specific PDEs for treatment of specific disease states. (Soderling S. H., Beavo J. A.; *Curr. Opin. Cell. Biol.* 2000, 12, 174-179; Cote R. H.; *Int. J. Impotence. Res.* 2004, 16 (Suppl. 1), S28-S33; Bender A. T., Beavo J A.; *Pharmacol. Rev.* 2006, 58, 488-520.)

Several recently developed compounds are more potent and selective in inhibiting particular PDEs namely PDE-1 (Vinpocetine), PDE-2 (EHNA (erythro-9-(2-hydroxy-3-nonyl)adenine), PDE-3 (Amrinone, Anagrelide, Cilostazol), PDE-4 (Piclamilast, Tibenelast, Benafentrine and Zardaverine) and PDE-5 (Sildenafil, Tadalafin, Vardenafil and Avanafil).

PDE5 inhibitors: Phosphodiesterase (V) inhibitors (PDE5 inhibitors) are an important class of pharmaceutical compounds. The first clinical use of these compounds was in the treatment of male erectile dysfunction (MED), (Boolell M., et al.; *Int. J. Impot. Res.* 1996, 8, 47-52). Further uses are being proposed and investigated, including pulmonary hypertension (Wilkens H., et al.; *Circulation* 2001, 104, 1218-1222). There are currently four commercial PDE5 inhibitors which have been approved by the FDA, and these are shown below.

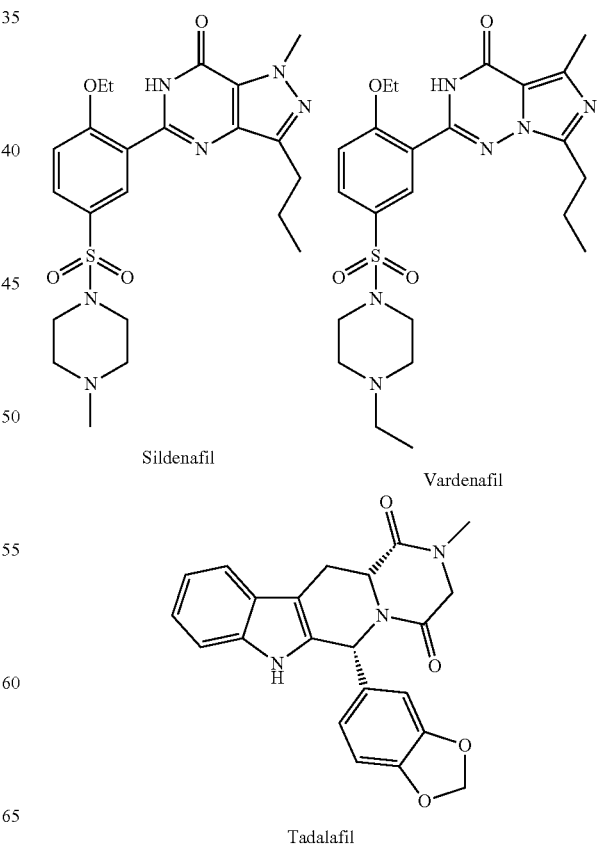

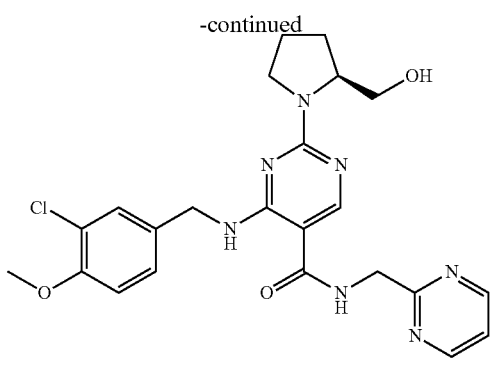

Avanafil

Commercial PDE-5 Inhibitors

The utility of sildenafil as an efficacious, orally active agent for the treatment of male erectile dysfunction (MED), (Terrett N. K., Bell A. S., Brown D., Ellis P.; Bioorg. Med. Chem. Lett. 1996, 6, 1819-1824) has created significant interest in the discovery of additional phosphodiesterase type 5 (PDE5) inhibitors. (Eardley, I. *Exp. Opin. Invest. Drugs.* 1997, 6, 1803-1810). PDE5 is the primary cGMP-hydrolyzing enzyme present in the corpus cavernosum, the smooth muscle in the penis which helps control vascular tone. When a man is sexually stimulated, nitric oxide is released from the cavernosal nerve. This activates soluble guanylyl cyclase in the corpus cavernosum, causing an increase in intracellular cGMP, which is normally hydrolyzed by PDE5. Inhibition of PDE5 elevates levels of the cyclic nucleotide, leading to enhanced relaxation of smooth muscle, increased arterial inflow, venous congestion, and ultimately an erection. Despite the efficacy of this molecule as a treatment for MED, there are notable drawbacks associated with its use. Clinically significant adverse effects such as nausea, headache, cutaneous flushing, and visual disturbances have been noted and their incidence is dose-dependent. Certain of these are thought to be due to nonspecific inhibition of other PDEs, specifically PDE1 and PDE6. (Beavo, J. A. *Physiol. Rev.* 1995, 75, 725-748). Thus, the identification of potent and more selective PDE5 inhibitors is of primary interest. We evolved a program for design, synthesis and its evaluation as isoform selective PDE inhibitor.

OBJECTS OF THE PRESENT INVENTION

The main object of the present invention is to provide compounds of pyrazolo pyrimidinone as PDE5 inhibitors.

Another object of the present invention is to provide a process for the preparation of pyrazolo pyrimidinone compounds.

Still another object of the present invention is to evaluate biological activity of pyrazolo pyrimidinone compounds as PDE5 inhibitors.

Yet another object of the present invention is to identify isoform selectivity of these compounds for different PDE enzymes to find enzyme specificity.

Still another object of the present invention is to evaluate in vivo biological activity in animals (rabbit or rat models) of pyrazolo pyrimidinone compounds as PDE5 inhibitors.

Yet another object of the present invention is that the compounds of the present invention are useful for the treatment of the male erectile dysfunction and for the treatment of impotence.

SUMMARY OF THE INVENTION

The present invention relates to the novel compounds of pyrazolo pyrimidinone based scaffold as PDE5 inhibitors. Several compounds in the series have been designed and synthesized based on pyrazolo pyrimidinone scaffold. These molecules were screened for PDE5 activity and they are found to be potential PDE5 inhibitors. Some of the compounds have shown $IC_{50}$ value in nano molar range.

Accordingly the present invention provides a compound having formula 1 and pharmaceutically acceptable salts thereof Formula 1

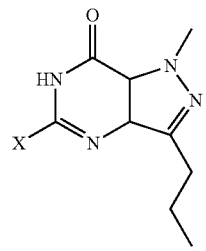

wherein 'X' is selected from the group consisting of

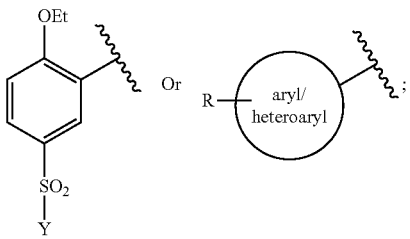

wherein
Y=

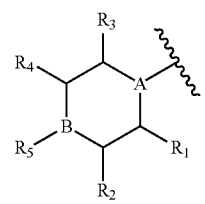

wherein, A and B represents —N, —S, —CH, —CR, —NH, —NR;
wherein, R is BocHN, substituted aryl, heteroaryl, alkyl, heterocycloalkane with substitution selected from the group consisting of ketone, aryl, methyl, ethyl, propyl, butyl, pentyl, hexyl, heptyl, octyl, nonyl and decyl optionally having hydroxyl, amino, halo group at the terminal position of the carbon chain optionally having unsaturation on carbon chain at any position with different substitutions,
wherein, $R_1$ to $R_5$ are either independently selected from H, alkyl, aryl, halo, oxy, hydroxy, alkoxy, alkyl halide, alkyne ether, allyl ether, substituted alkene, amino, formyl, nitro with substitutions optionally having heteroaryl substitutions,
wherein, R in general represents an independently selected groups with substitutions on aryl ring selected from the group consisting of halo, alkoxy, nitro, amino, oxy, thio, carboxylic, formyl, hydroxyl, prenyl and isoprenyl, wherein, the heteroaryl group is selected from the group consisting of pyridyl, furyl, thiphenyl, thiobenzyl, indolyl, thioindolyl, quinolyl, quinazolinyl, isoquinolyl, benzopyranyl, benzothiozolyl, benzooxazolyl, oxazolyl, triazolyl and tetrazolyl.

In an embodiment of the present invention the compound of formula 1 having formula

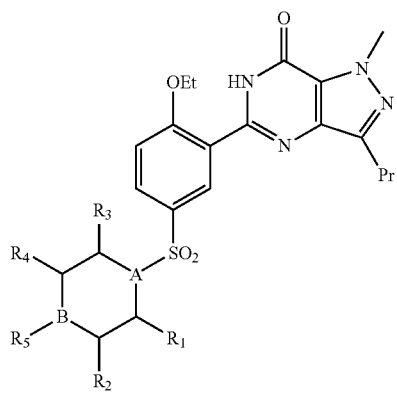

Formula 1A

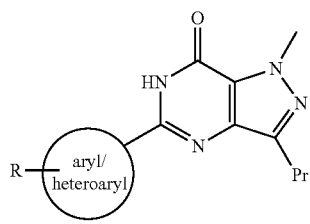

Formula 1B wherein, Formula 1A represents general structure for cyclic ring containing compounds wherein, the cyclic ring is directly bonded to —SO$_2$ placed on arylring at $4^{th}$ position of —OEt substitution, wherein, the cyclic ring is selected from the group consisting of five membered, six membered and seven membered, wherein, the cyclic ring contains substitutions, wherein, A and B represents —N, —S, —CH, —CR, —NH, —NR;

wherein, R is BocHN, substituted aryl, heteroaryl, alkyl, heterocycloalkane with substitution selected from the group consisting of ketone, aryl, methyl, ethyl, propyl, butyl, pentyl, hexyl, heptyl, octyl, nonyl and decyl optionally having hydroxyl, amino, halo group at the terminal position of the carbon chain optionally having unsaturation on carbon chain at any position with different substitutions, wherein, $R_1$ to $R_5$ are either independently selected from H, alkyl, aryl, halo, oxy, hydroxy, alkoxy, alkyl halide, alkyne ether, allyl ether, substituted alkene, amino, formyl, nitro with substitutions optionally having heteroaryl substitutions, wherein, R in general represents an independently selected groups with substitutions on aryl ring selected from the group consisting of halo, alkoxy, nitro, amino, oxy, thio, carboxylic, formyl, hydroxyl, prenyl and isoprenyl, wherein, the heteroaryl group is selected from the group consisting of pyridyl, furyl, thiphenyl, thiobenzyl, indolyl, thioindolyl, quinolyl, quinazolinyl, isoquinolyl, benzopyranyl, benzothiozolyl, benzooxazolyl, oxazolyl, triazolyl and tetrazolyl.

In another embodiment of the present invention, the representative compounds of formula 1A are selected from the group consisting of

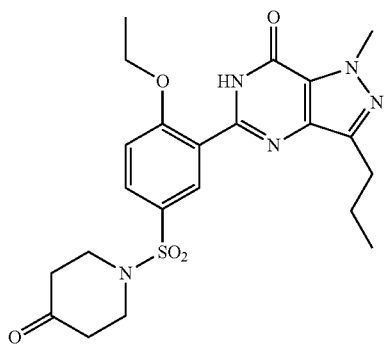 [SMILES: CCCc1nn(C)c2c(=O)[nH]c(-c3cc(S(=O)(=O)N4CCC(=O)CC4)ccc3OCC)nc12]

5-(2-ethoxy-5-((4-oxopiperidin-1-yl)sulfonyl)phenyl)-1-methyl-3-propyl-1H-pyrazolo[4,3-d]pyrimidin-7(6H)-one,

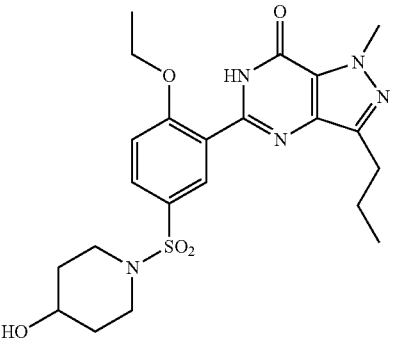 [SMILES: CCCc1nn(C)c2c(=O)[nH]c(-c3cc(S(=O)(=O)N4CCC(O)CC4)ccc3OCC)nc12]

5-(2-ethoxy-5-((4-hydroxypiperidin-1-yl)sulfonyl)phenyl)-1-methyl-3-propyl-1H-pyrazolo[4,3-d]pyrimidin-7(6H)-one,

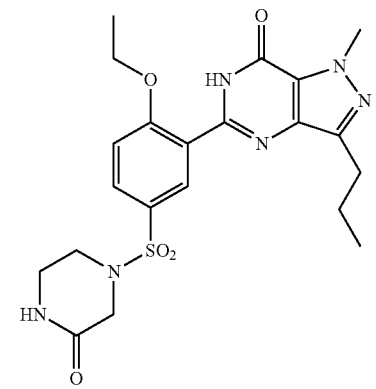 [SMILES: CCCc1nn(C)c2c(=O)[nH]c(-c3cc(S(=O)(=O)N4CCNC(=O)C4)ccc3OCC)nc12]

5-(2-ethoxy-5-((3-oxopiperazin-1-yl)sulfonyl)phenyl)-1-methyl-3-propyl-1H-pyrazolo[4,3-d]pyrimidin-7(6H)-one,

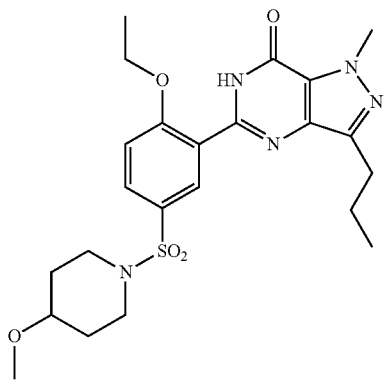 [SMILES: CCCc1nn(C)c2c(=O)[nH]c(-c3cc(S(=O)(=O)N4CCC(OC)CC4)ccc3OCC)nc12]

5-(2-ethoxy-5-(4-methoxypiperidin-1-yl)sulfonyl)phenyl)-1-methyl-3-propyl-1H-pyrazolo[4,3-d]pyrimidin-7(6H)-one,

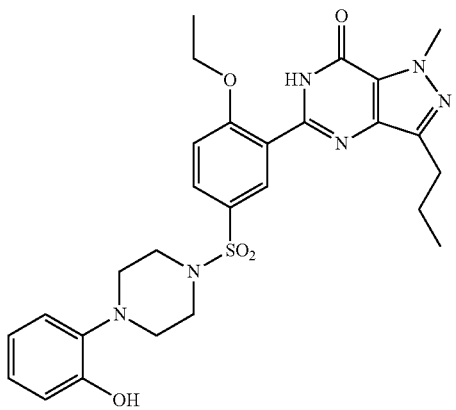

5-(2-ethoxy-5-((4-(2-hydroxyphenyl)piperazin-1-yl)sulfonyl) phenyl)-1-methyl-3-propyl-1H-pyrazolo[4,3-d]pyrimidin-7(6H)-one),

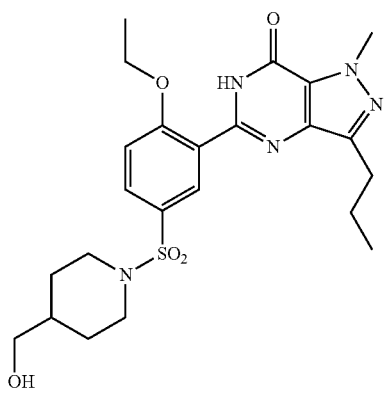 [SMILES: CCCc1nn(C)c2c(=O)[nH]c(-c3cc(S(=O)(=O)N4CCC(CO)CC4)ccc3OCC)nc12]

5-(2-ethoxy-5-((4-(hydroxymethyl)piperidin-1-yl)sulfonyl) phenyl)-1-methyl-3-propyl-1H-pyrazolo[4,3-d]pyrimidin-7(6H)-one,

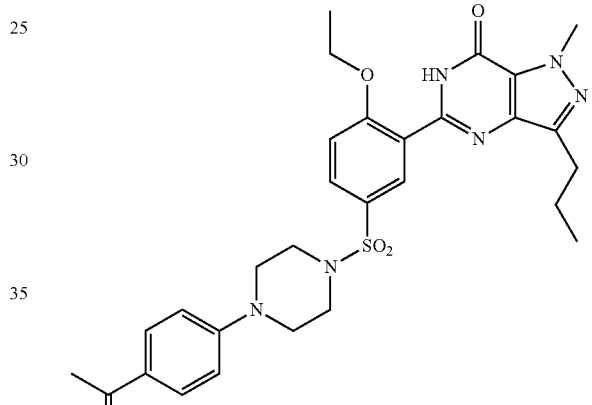

5-(5-((4-(4-acetylphenyl)piperazin-1-yl)sulfonyl)-2-ethoxy phenyl)-1-methyl-3-propyl-1H-pyrazolo[4,3-d]pyrimidin-7(6H)-one,

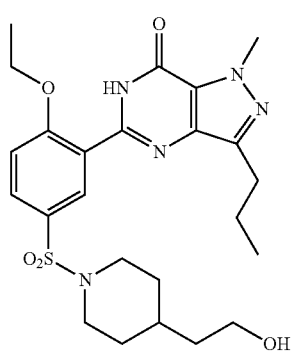 [SMILES: CCCc1nn(C)c2c(=O)[nH]c(-c3cc(S(=O)(=O)N4CCC(CCO)CC4)ccc3OCC)nc12]

5-(2-ethoxy-5-((4-(2-hydroxyethyl)piperidin-1-yl)sulfonyl) phenyl)-1-methyl-3-propyl-1H-pyrazolo[4,3-d]pyrimidin-7(6H)-one,

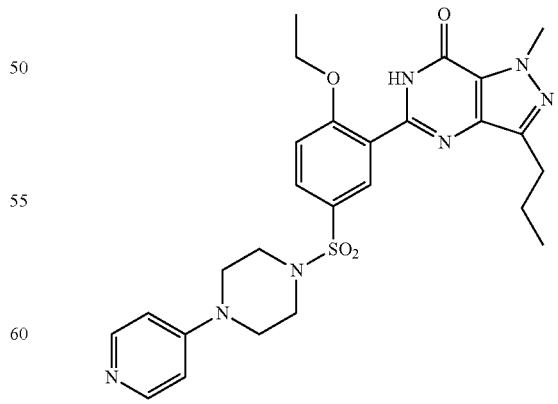

5-(2-ethoxy-5-((4-(pyridin-4-yl)piperazin-1-yl)sulfonyl) phenyl)-1-methyl-3-propyl-1H-pyrazolo[4,3-d]pyrimidin-7(6H)-one,

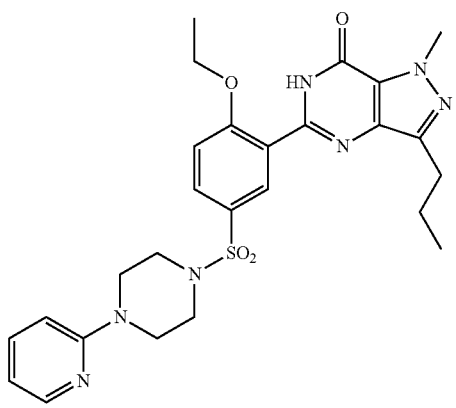 [SMILES: CCCc1nn(C)c2c(=O)[nH]c(-c3cc(S(=O)(=O)N4CCN(c5ccccn5)CC4)ccc3OCC)nc12]

5-(2-ethoxy-5-((4-(pyridin-2-yl)piperazin-1-yl)sulfonyl)phenyl)-1-methyl-3-propyl-1H-pyrazolo[4,3-d]pyrimidin-7(6H)-one,

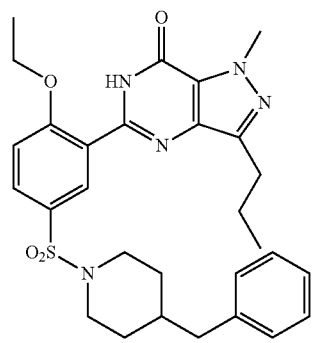

5-(5-((4-benzylpiperidin-1-yl)sulfonyl)-2-ethoxyphenyl)-1-methyl-3-propyl-1H-pyrazolo[4,3-d]pyrimidin-7(6H)-one,

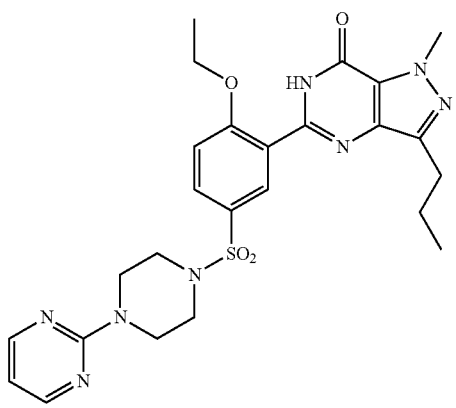 [SMILES: CCCc1nn(C)c2c(=O)[nH]c(-c3cc(S(=O)(=O)N4CCN(c5ncccn5)CC4)ccc3OCC)nc12]

5-(2-ethoxy-5-((4-(pyrimidin-2-yl)piperazin-1-yl)sulfonyl)phenyl)-1-methyl-3-propyl-1H-pyrazolo[4,3-d]pyrimidin-7(6H)-one,

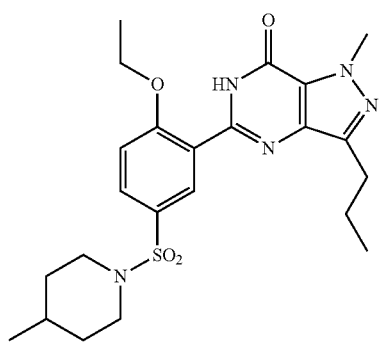

5-(2-ethoxy-5-((4-methylpiperidin-1-yl)sulfonyl)phenyl)-1-methyl-3-propyl-1H-pyrazolo[4,3-d]pyrimidin-7(6H)-one,

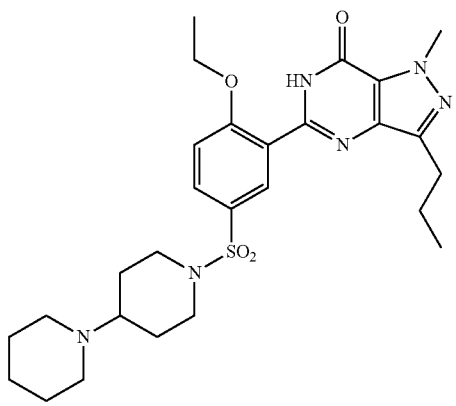 [SMILES: CCCc1nn(C)c2c(=O)[nH]c(-c3cc(S(=O)(=O)N4CCC(N5CCCCC5)CC4)ccc3OCC)nc12]

5-(5-([1,4'-bipiperidin]-1'-ylsulfonyl)-2-ethoxyphenyl)-1-methyl-3-propyl-1H-pyrazolo[4,3-d]pyrimidin-7(6H)-one,

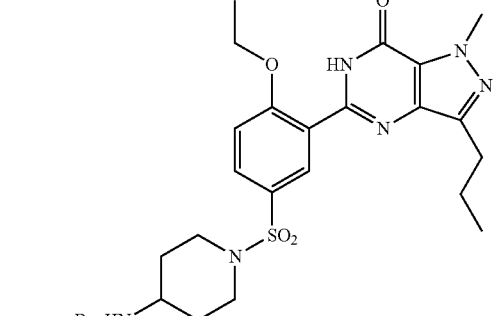

tert-butyl (1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)carbamate,

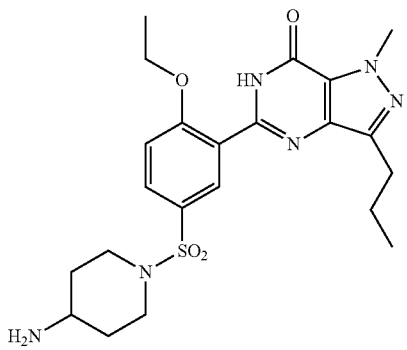 [SMILES: CCCc1nn(C)c2c(=O)[nH]c(-c3cc(S(=O)(=O)N4CCC(N)CC4)ccc3OCC)nc12]

5-(5-((4-aminopiperidin-1-yl)sulfonyl)-2-ethoxyphenyl)-1-methyl-3-propyl-1H-pyrazolo[4,3-d]pyrimidin-7(6H)-one,

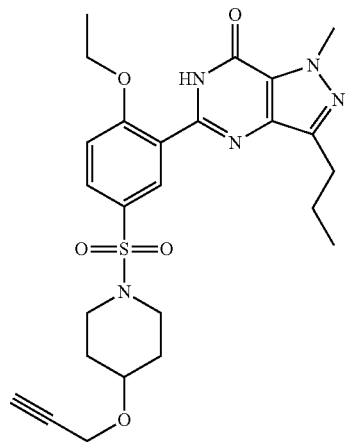

5-(2-ethoxy-5-((4-(prop-2-yn-1-yloxy)piperidin-1-yl)sulfonyl)phenyl)-1-methyl-3-propyl-1H-pyrazolo[4,3-d]pyrimidin-7(6H)-one,

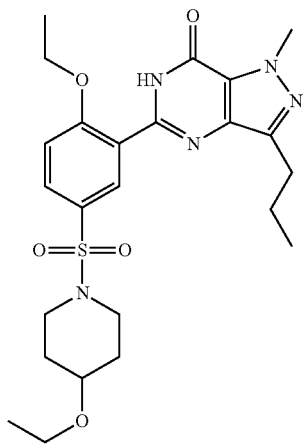 [SMILES: CCCc1nn(C)c2c(=O)[nH]c(-c3cc(S(=O)(=O)N4CCC(OCC)CC4)ccc3OCC)nc12]

5-(2-ethoxy-5-((4-ethoxypiperidin-1-yl)sulfonyl)phenyl)-1-methyl-3-propyl-1H-pyrazolo[4,3-d]pyrimidin-7(6H)-one,

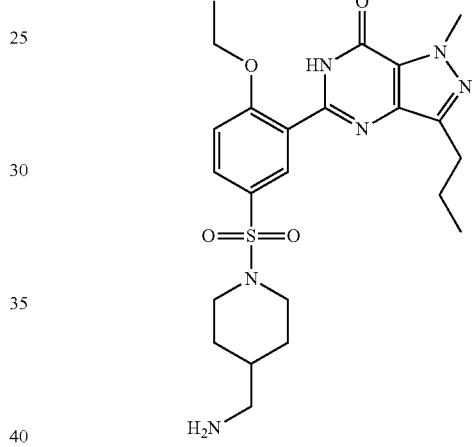

5-(5-((4-(aminomethyl)piperidin-1-yl)sulfonyl)-2-ethoxyphenyl)-1-methyl-3-propyl-1H-pyrazolo[4,3-d]pyrimidin-7(6H)-one,

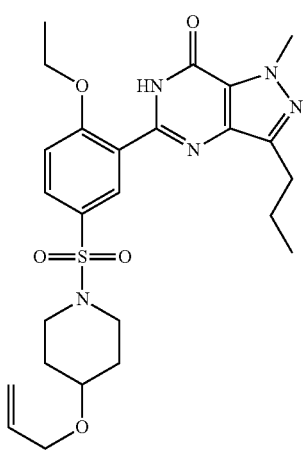 [SMILES: C=CCOC1CCN(S(=O)(=O)c2ccc(OCC)c(-c3nc4c(CCC)nn(C)c4c(=O)[nH]3)c2)CC1]

5-(5-((4-(allyloxy)piperidin-1-yl)sulfonyl)-2-ethoxyphenyl)-1-methyl-3-propyl-1H-pyrazolo[4,3-d]pyrimidin-7(6H)-one,

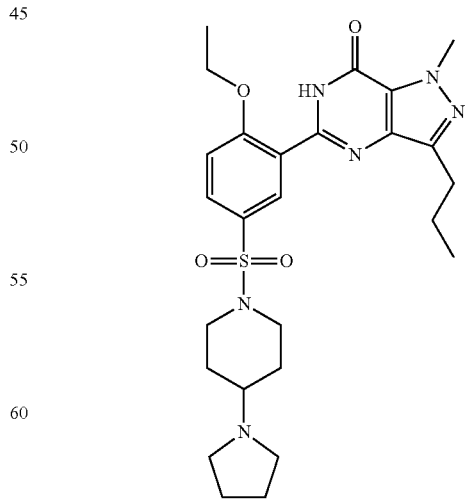

5-(2-ethoxy-5-((4-(pyrrolidin-1-yl)piperidin-1-yl)sulfonyl)phenyl)-1-methyl-3-propyl-1H-pyrazolo[4,3-d]pyrimidin-7(6H)-one,

| 13 | 14 |
|---|---|
| 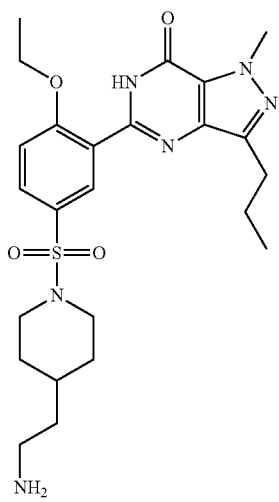 [SMILES: CCCc1nn(C)c2c(=O)[nH]c(-c3cc(S(=O)(=O)N4CCC(CCN)CC4)ccc3OCC)nc12] 5-(5-((4-(2-aminoethyl)piperidin-1-yl) sulfonyl)-2-ethoxyphenyl)-1-methyl-3-propyl-1H-pyrazolo[4,3-d]pyrimidin-7(6H)-one, | 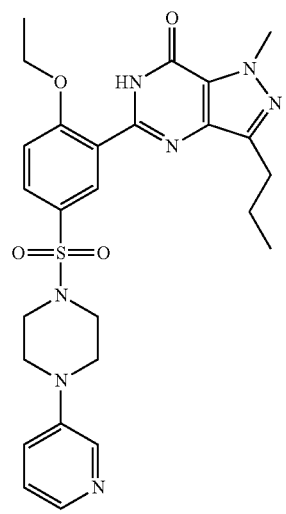 5-(2-ethoxy-5-((4-(pyridin-3-yl)piperazin-1-yl)sulfonyl)phenyl)-1-methyl-3-propyl-1H-pyrazolo[4,3-d]pyrimidin-7(6H)-one, |
| 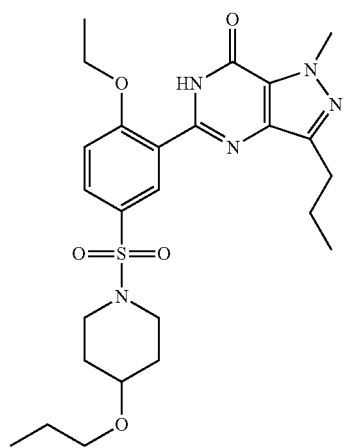 [SMILES: CCCOC1CCN(S(=O)(=O)c2ccc(OCC)c(-c3nc4c(CCC)nn(C)c4c(=O)[nH]3)c2)CC1] 5-(2-ethoxy-5-((4-propoxypiperidin-1-yl)sulfonyl)phenyl)-1-methyl-3-propyl-1H-pyrazolo[4,3-d]pyrimidin-7(6H)-one, | 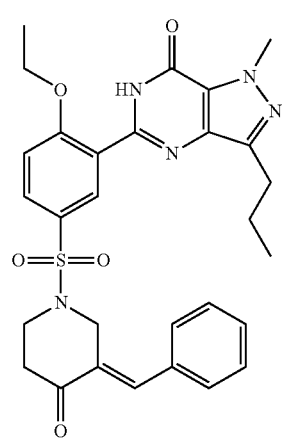 (E)-5-(5-(3-benzylidene-4-oxopiperidin-1-yl)sulfonyl)-2-ethoxyphenyl)-1-methyl-3-propyl-1H-pyrazolo[4,3-d]pyrimidin-7(6H)-one, |
| 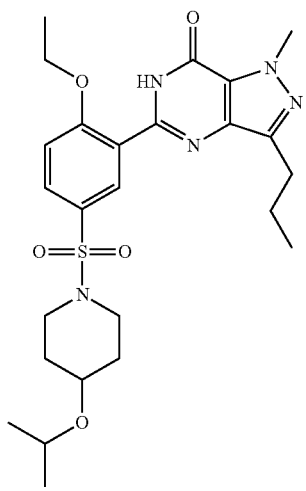 [SMILES: CCCc1nn(C)c2c(=O)[nH]c(-c3cc(S(=O)(=O)N4CCC(OC(C)C)CC4)ccc3OCC)nc12] 5-(2-ethoxy-5-((4-isopropoxypiperidin-1-yl)sulfonyl)phenyl)-1-methyl-3-propyl-1H-pyrazolo[4,3-d]pyrimidin-7(6H)-one, | 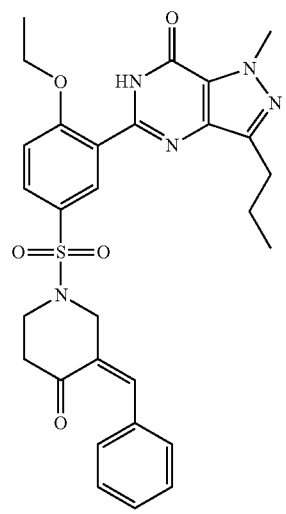 [SMILES: CCCc1nn(C)c2c(=O)[nH]c(-c3cc(S(=O)(=O)N4CCC(=O)/C(=C\c5ccccc5)C4)ccc3OCC)nc12] (Z)-5-(5-((3-benzylidene-4-oxopiperidin-1-yl)sulfonyl)-2-ethoxyphenyl)-1-methyl-3-propyl-1H-pyrazolo[4,3-d]pyrimidin-7(6H)-one, |

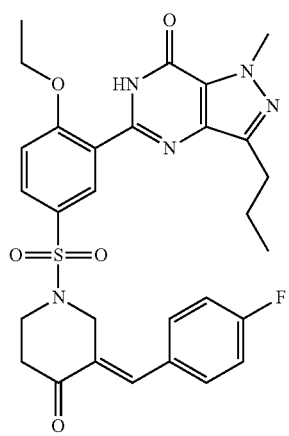 [SMILES: CCCc1nn(C)c2c(=O)[nH]c(-c3cc(S(=O)(=O)N4CCC(=O)/C(=C/c5ccc(F)cc5)C4)ccc3OCC)nc12]

(E)-5-(2-ethoxy-5-((3-(4-fluorobenzylidene)-4-oxopiperidin-1-yl)sulfonyl)phenyl)-1-methyl-3-propyl-1H-pyrazolo[4,3-d]pyrimidin-7(6H)-one,

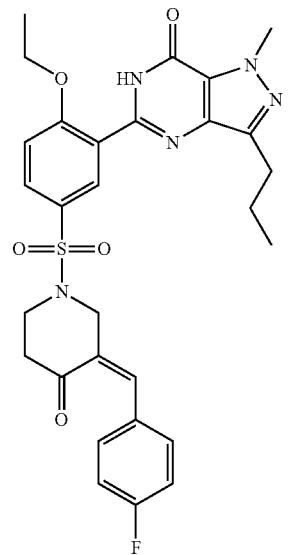 [SMILES: CCCc1nn(C)c2c(=O)[nH]c(-c3cc(S(=O)(=O)N4CCC(=O)/C(=C\c5ccc(F)cc5)C4)ccc3OCC)nc12]

(Z)-5-(2-ethoxy-5-((3-(4-fluorobenzylidene)-4-oxopiperidin-1-yl)sulfonyl)phenyl)-1-methyl-3-propyl-1H-pyrazolo[4,3-d]pyrimidin-7(6H)-one,

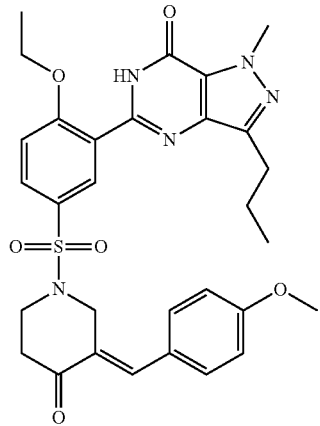 [SMILES: CCCc1nn(C)c2c(=O)[nH]c(-c3cc(S(=O)(=O)N4CCC(=O)/C(=C/c5ccc(OC)cc5)C4)ccc3OCC)nc12]

(E)-5-(2-ethoxy-5-((3-(4-methoxybenzylidene)-4-oxopiperidin-1-yl)sulfonyl)phenyl)-1-methyl-3-propyl-1H-pyrazolo[4,3-d]pyrimidin-7(6H)-one,

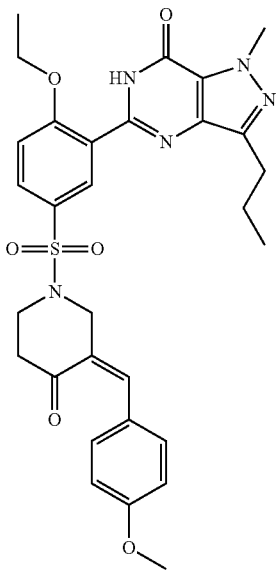 [SMILES: CCCc1nn(C)c2c(=O)[nH]c(-c3cc(S(=O)(=O)N4CCC(=O)/C(=C\c5ccc(OC)cc5)C4)ccc3OCC)nc12]

(Z)-5-(2-ethoxy-5-((3-(4-methoxybenzylidene)-4-oxopiperidin-1-yl)sulfonyl)phenyl)-1-methyl-3-propyl-1H-pyrazolo[4,3-d]pyrimidin-7(6H)-one,

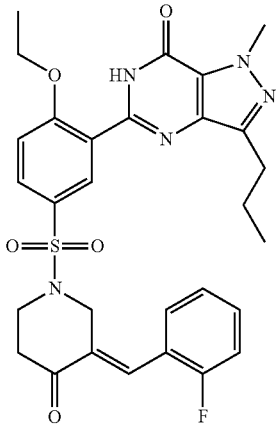 [SMILES: CCCc1nn(C)c2c(=O)[nH]c(-c3cc(S(=O)(=O)N4CCC(=O)/C(=C/c5ccccc5F)C4)ccc3OCC)nc12]

(E)-5-(2-ethoxy-5-((3-(2-fluorobenzylidene)-4-oxopiperidin-1-yl)sulfonyl)phenyl)-1-methyl-3-propyl-1H-pyrazolo[4,3-d]pyrimidin-7(6H)-one,

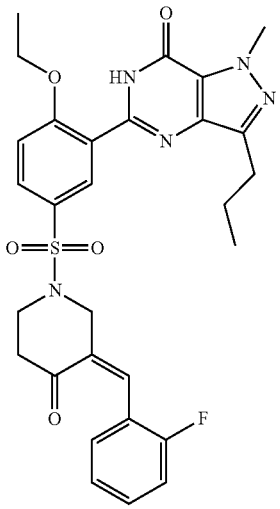 [SMILES: CCCc1nn(C)c2c(=O)[nH]c(-c3cc(S(=O)(=O)N4CCC(=O)/C(=C\c5ccccc5F)C4)ccc3OCC)nc12]

(Z)-5-(2-ethoxy-5-((3-(2-fluorobenzylidene)-4-oxopiperidin-1-yl)sulfonyl)phenyl)-1-methyl-3-propyl-1H-pyrazolo[4,3-d]pyrimidin-7(6H)-one,

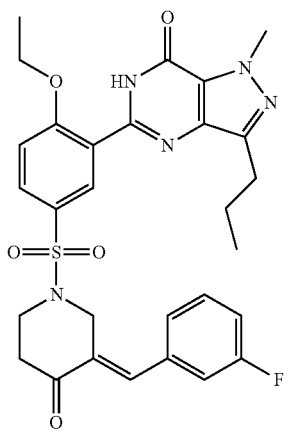 [SMILES: CCCc1nn(C)c2c(=O)[nH]c(-c3cc(S(=O)(=O)N4CCC(=O)/C(=C/c5cccc(F)c5)C4)ccc3OCC)nc12]

(E)-5-(2-ethoxy-5-((3-(3-fluorobenzylidene)-4-oxopiperidin-1-yl)sulfonyl)phenyl)-1-methyl-3-propyl-1H-pyrazolo[4,3-d]pyrimidin-7(6H)-one,

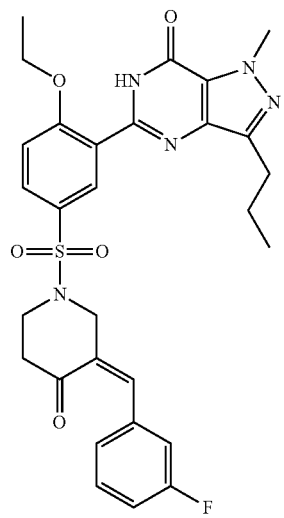 [SMILES: CCCc1nn(C)c2c(=O)[nH]c(-c3cc(S(=O)(=O)N4CCC(=O)/C(=C\c5cccc(F)c5)C4)ccc3OCC)nc12]

(Z)-5-(2-ethoxy-5-((3-(3-fluorobenzylidene)-4-oxopiperidin-1-yl)sulfonyl)phenyl)-1-methyl-3-propyl-1H-pyrazolo[4,3-d]pyrimidin-7(6H)-one,

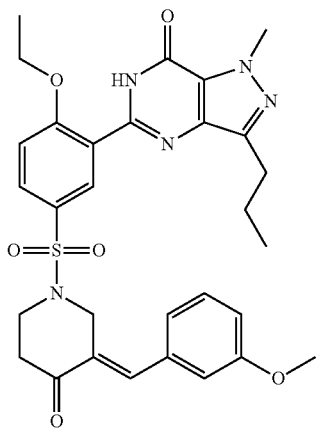 [SMILES: CCCc1nn(C)c2c(=O)[nH]c(-c3cc(S(=O)(=O)N4CCC(=O)/C(=C/c5cccc(OC)c5)C4)ccc3OCC)nc12]

(E)-5-(2-ethoxy-5-((3-(3-methoxybenzylidene)-4-oxopiperidin-1-yl)sulfonyl)phenyl)-1-methyl-3-propyl-1H-pyrazolo[4,3-d]pyrimidin-7(6H)-one,

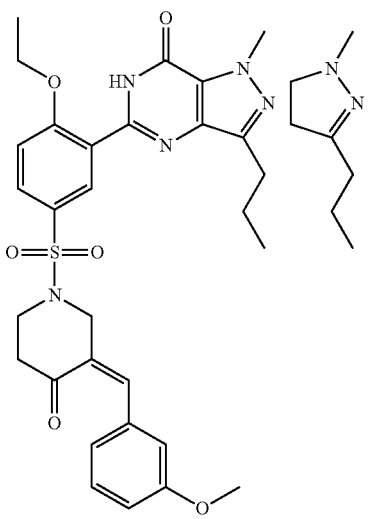

(Z)-5-(2-ethoxy-5-((3-(3-methoxybenzylidene)-4-oxopiperidin-1-yl)sulfonyl)phenyl)-1-methyl-3-propyl-1H-pyrazolo[4,3-d]pyrimidin-7(6H)-one,

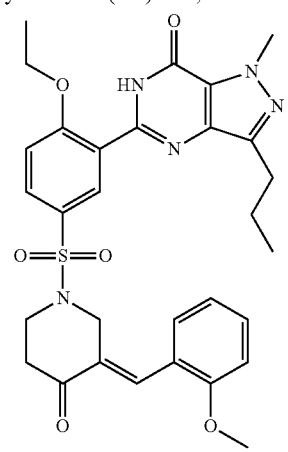

(E)-5-(2-ethoxy-5-((3-(2-methoxybenzylidene)-4-oxopiperidin-1-yl)sulfonyl)phenyl)-1-methyl-3-propyl-1H-pyrazolo[4,3-d]pyrimidin-7(6H)-one,

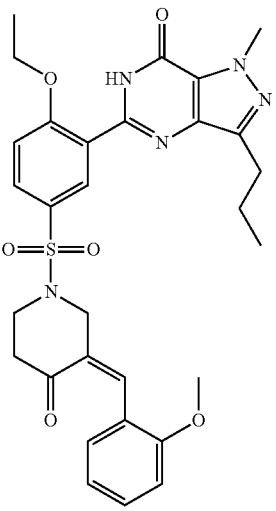 [SMILES: CCCc1nn(C)c2c(=O)[nH]c(-c3cc(S(=O)(=O)N4CCC(=O)/C(=C\c5ccccc5OC)C4)ccc3OCC)nc12]

(Z)-5-(2-ethoxy-5-((3-(2-methoxybenzylidene)-4-oxopiperidin-1-yl)sulfonyl)phenyl)-1-methyl-3-propyl-1H-pyrazolo[4,3-d]pyrimidin-7(6H)-one,

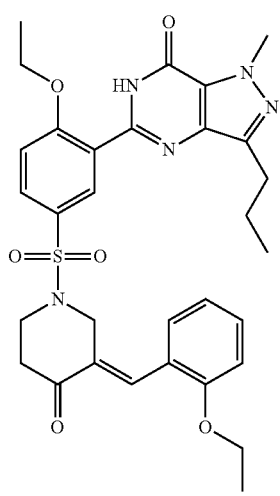 [SMILES: CCCc1nn(C)c2c(=O)[nH]c(-c3cc(S(=O)(=O)N4CCC(=O)/C(=C/c5ccccc5OCC)C4)ccc3OCC)nc12]

(E)-5-(2-ethoxy-5-((3-(2-ethoxybenzylidene)-4-oxopiperi-din-1-yl)sulfonyl)phenyl)-1-methyl-3-propyl-1H-pyra-zolo[4,3-d]pyrimidin-7(6H)-one,

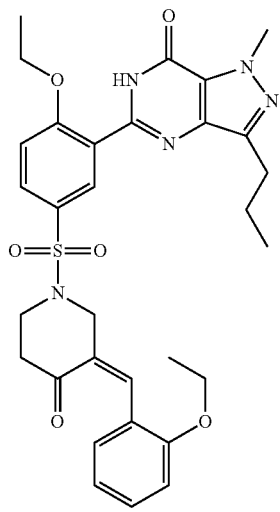 [SMILES: CCCc1nn(C)c2c(=O)[nH]c(-c3cc(S(=O)(=O)N4CCC(=O)/C(=C\c5ccccc5OCC)C4)ccc3OCC)nc12]

(Z)-5-(2-ethoxy-5-((3-(2-ethoxybenzylidene)-4-oxopiperi-din-1-yl)sulfonyl)phenyl)-1-methyl-3-propyl-1H-pyra-zolo[4,3-d]pyrimidin-7(6H)-one,

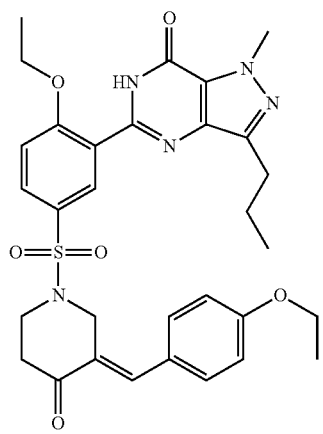 [SMILES: CCCc1nn(C)c2c(=O)[nH]c(-c3cc(S(=O)(=O)N4CCC(=O)/C(=C/c5ccc(OCC)cc5)C4)ccc3OCC)nc12]

(E)-5-(2-ethoxy-5-((3-(4-ethoxybenzylidene)-4-oxopiperi-din-1-yl)sulfonyl)phenyl)-1-methyl-3-propyl-1H-pyra-zolo[4,3-d]pyrimidin-7(6H)-one,

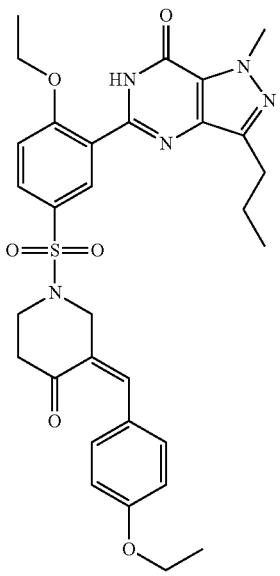 [SMILES: CCCc1nn(C)c2c(=O)[nH]c(-c3cc(S(=O)(=O)N4CCC(=O)/C(=C\c5ccc(OCC)cc5)C4)ccc3OCC)nc12]

(Z)-5-(2-ethoxy-5-((3-(4-ethoxybenzylidene)-4-oxopiperi-din-1-yl)sulfonyl)phenyl)-1-methyl-3-propyl-1H-pyra-zolo[4,3-d]pyrimidin-7(6H)-one,

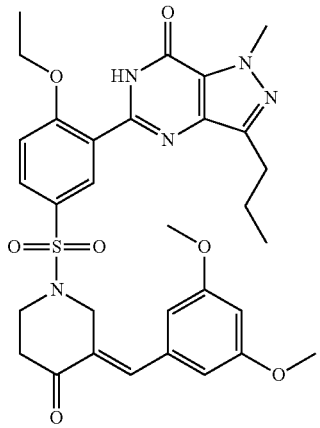 [SMILES: CCCc1nn(C)c2c(=O)[nH]c(-c3cc(S(=O)(=O)N4CCC(=O)/C(=C/c5cc(OC)cc(OC)c5)C4)ccc3OCC)nc12]

(E)-5-(5-((3-(3,5-dimethoxybenzylidene)-4-oxopiperidin-1-yl)sulfonyl)-2-ethoxyphenyl)-1-methyl-3-propyl-1H-pyrazolo[4,3-d]pyrimidin-7(6H)-one,

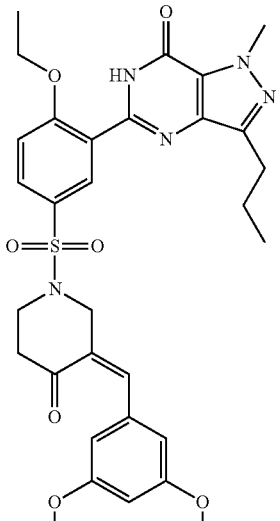

(Z)-5-(5-((3-(3,5-dimethoxybenzylidene)-4-oxopiperidin-1-yl)sulfonyl)-2-ethoxyphenyl)-1-methyl-3-propyl-1H-pyrazolo[4,3-d]pyrimidin-7(6H)-one,

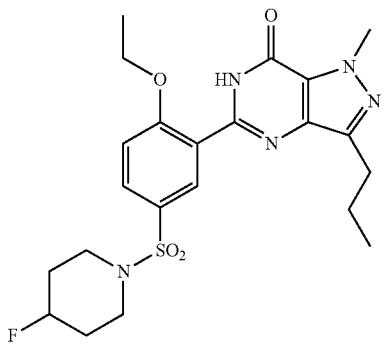 [SMILES: CCCc1nn(C)c2c(=O)[nH]c(-c3cc(S(=O)(=O)N4CCC(F)CC4)ccc3OCC)nc12]

5-(2-ethoxy-5-((4-fluoropiperidin-1-yl)sulfonyl)phenyl)-1-methyl-3-propyl-1H-pyrazolo[4,3-d]pyrimidin-7(6H)-one,

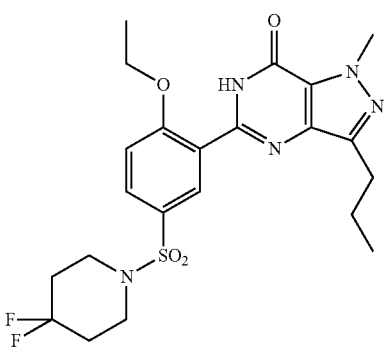 [SMILES: CCCc1nn(C)c2c(=O)[nH]c(-c3cc(S(=O)(=O)N4CCC(F)(F)CC4)ccc3OCC)nc12]

5-(5-((4,4-difluoropiperidin-1-yl)sulfonyl)-2-ethoxyphenyl)-1-methyl-3-propyl-1H-pyrazolo[4,3-d]pyrimidin-7(6H)-one, and

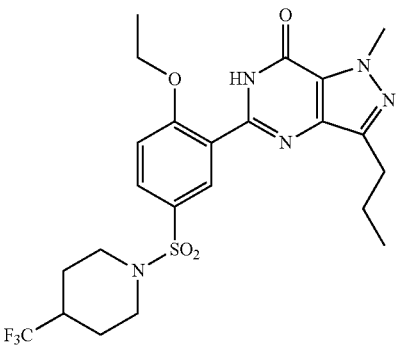 [SMILES: CCCc1nn(C)c2c(=O)[nH]c(-c3cc(S(=O)(=O)N4CCC(C(F)(F)F)CC4)ccc3OCC)nc12]

5-(2-ethoxy-5-((4-(trifluoromethyl)piperidin-1-yl)sulfonyl)phenyl)-1-methyl-3-propyl-1H-pyrazolo[4,3-d]pyrimidin-7(6H)-one.

In an embodiment of the present invention the representative compounds of formula 1B are selected from the group consisting of:

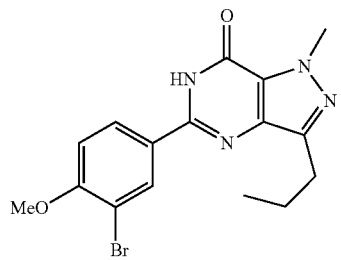 [SMILES: CCCc1nn(C)c2c(=O)[nH]c(-c3ccc(OC)c(Br)c3)nc12]

5-(3-bromo-4-methoxyphenyl)-1-methyl-3-propyl-1H-pyrazolo[4,3-d]pyrimidin-7(6H)-one,

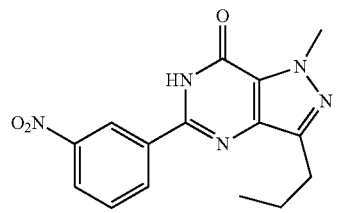 [SMILES: CCCc1nn(C)c2c(=O)[nH]c(-c3cccc([N+](=O)[O-])c3)nc12]

1-methyl-5-(3-nitrophenyl)-3-propyl-1H-pyrazolo[4,3-d] pyrimidin-7(6H)-one,

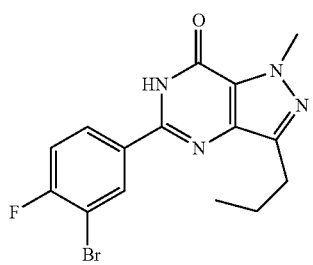 [SMILES: CCCc1nn(C)c2c(=O)[nH]c(-c3ccc(F)c(Br)c3)nc12]

5-(3-bromo-4-fluorophenyl)-1-methyl-3-propyl-1H-pyrazolo [4,3-d]pyrimidin-7(6H)-one,

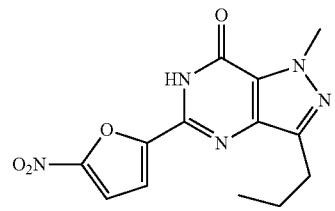 [SMILES: CCCc1nn(C)c2c(=O)[nH]c(-c3ccc([N+](=O)[O-])o3)nc12]

1-methyl-5-(5-nitrofuran-2-yl)-3-propyl-1H-pyrazolo[4,3-d] pyrimidin-7(6H)-one,

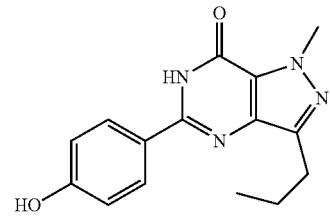 [SMILES: CCCc1nn(C)c2c(=O)[nH]c(-c3ccc(O)cc3)nc12]

5-(4-hydroxyphenyl)-1-methyl-3-propyl-1H-pyrazolo[4,3-d] pyrimidin-7(6H)-one,

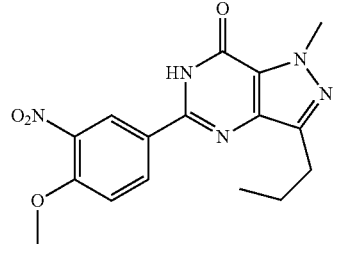 [SMILES: CCCc1nn(C)c2c(=O)[nH]c(-c3ccc(OC)c([N+](=O)[O-])c3)nc12]

5-(4-methoxy-3-nitrophenyl)-1-methyl-3-propyl-1H-pyrazolo [4,3-d]pyrimidin-7(6H)-one,

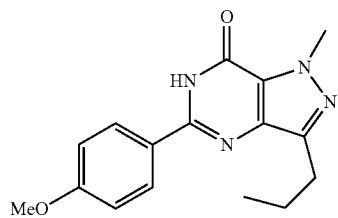 [SMILES: CCCc1nn(C)c2c(=O)[nH]c(-c3ccc(OC)cc3)nc12]

5-(4-methoxyphenyl)-1-methyl-3-propyl-1H-pyrazolo[4,3-d] pyrimidin-7(6H)-one,

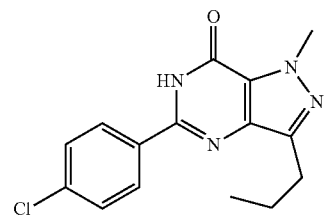 [SMILES: CCCc1nn(C)c2c(=O)[nH]c(-c3ccc(Cl)cc3)nc12]

5-(4-chlorophenyl)-1-methyl-3-propyl-1H-pyrazolo[4,3-d] pyrimidin-7(6H)-one,

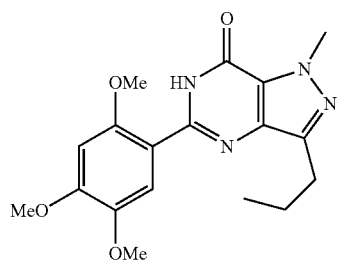 [SMILES: CCCc1nn(C)c2c(=O)[nH]c(-c3cc(OC)c(OC)cc3OC)nc12]

1-methyl-3-propyl-5-(2,4,5-trimethoxyphenyl)-1H-pyrazolo [4,3-d]pyrimidin-7(6H)-one,

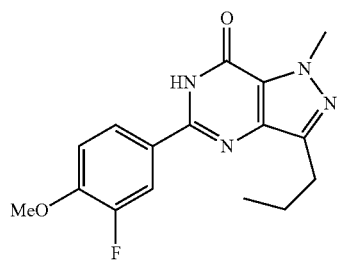 [SMILES: CCCc1nn(C)c2c(=O)[nH]c(-c3ccc(OC)c(F)c3)nc12]

5-(3-fluoro-4-methoxyphenyl)-1-methyl-3-propyl-1H-pyrazolo [4,3-d]pyrimidin-7(6H)-one,

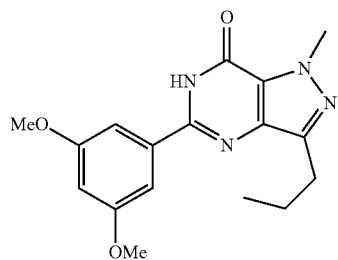 [SMILES: CCCc1nn(C)c2c(=O)[nH]c(-c3cc(OC)cc(OC)c3)nc12]

5-(3,5-dimethoxyphenyl)-1-methyl-3-propyl-1H-pyrazolo [4,3-d]pyrimidin-7(6H)-one,

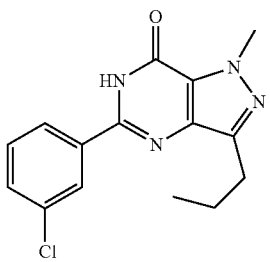 [SMILES: CCCc1nn(C)c2c(=O)[nH]c(-c3cccc(Cl)c3)nc12]

5-(3-chlorophenyl)-1-methyl-3-propyl-1H-pyrazolo[4,3-d] pyrimidin-7(6H)-one,

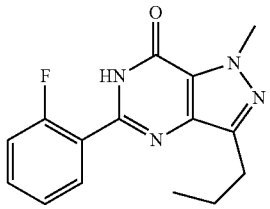 [SMILES: CCCc1nn(C)c2c(=O)[nH]c(-c3ccccc3F)nc12]

5-(2-fluorophenyl)-1-methyl-3-propyl-1H-pyrazolo[4,3-d] pyrimidin-7(6H)-one,

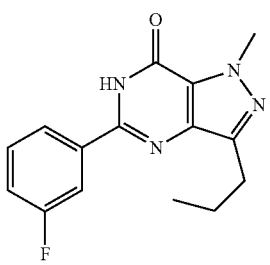

5-(3-fluorophenyl)-1-methyl-3-propyl-1H-pyrazolo[4,3-d] pyrimidin-7(6H)-one,

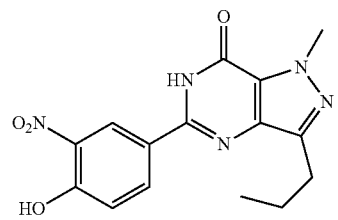 [SMILES: CCCc1nn(C)c2c(=O)[nH]c(-c3ccc(O)c([N+](=O)[O-])c3)nc12]

5-(4-hydroxy-3-nitrophenyl)-1-methyl-3-propyl-1H-pyrazolo [4,3-d]pyrimidin-7(6H)-one,

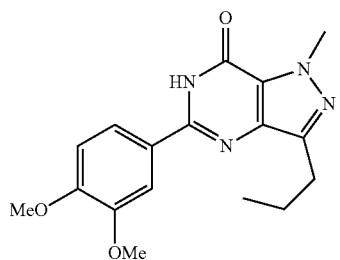 [SMILES: CCCc1nn(C)c2c(=O)[nH]c(-c3ccc(OC)c(OC)c3)nc12]

5-(3,4-dimethoxyphenyl)-1-methyl-3-propyl-1H-pyrazolo [4,3-d]pyrimidin-7(6H)-one,

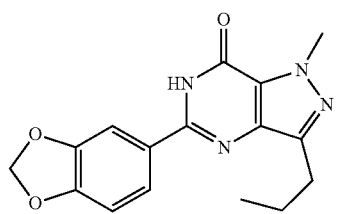 [SMILES: CCCc1nn(C)c2c(=O)[nH]c(-c3ccc4c(c3)OCO4)nc12]

5-(benzo[d][1,3]dioxol-5-yl)-1-methyl-3-propyl-1H-pyrazolo [4,3-d]pyrimidin-7(6H)-one, and

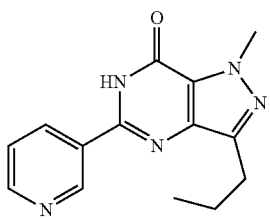 [SMILES: CCCc1nn(C)c2c(=O)[nH]c(-c3cccnc3)nc12]

1-methyl-3-propyl-5-(pyridin-3-yl)-1H-pyrazolo[4,3-d]pyrimidin-7(6H)-one.

The present invention also provides a process for the preparation of the compound of claim 1, wherein the steps comprising—

(i) reacting diethyl oxalate and 2-pentanone to obtain ethyl 3-propyl-1H-pyrazole-5-carboxylate (compound 1);

(ii) reacting compound 1 of step (i) with dimethyl sulfate to obtain ethyl 1-methyl-3-propyl-1H-pyrazole-5-carboxylate (compound 2);

(iii) treating compound 2 of step (ii) with NaOH solution to obtain 1-methyl-3-propyl-1H-pyrazole-5-carboxylic acid (compound 3);

(iv) reacting compound 3 of step (iii) with conc. $H_2SO_4$ and nitric acid to obtain 1-methyl-4-nitro-3-propyl-1H-pyrazole-5-carboxylic acid (compound 4);

(v) reacting compound 4 of step (iv) with $SOCl_2$ to obtain 1-methyl-4-nitro-3-propyl-1H-pyrazole-5-carboxamide (compound 5);

(vi) treating compound 5 of step (v) with $EtOH:H_2O$, Fe powder and $NH_4Cl$ to obtain 4-amino-1-methyl-3-propyl-1H-pyrazole-5-carboxamide (compound 6);

Compound 6

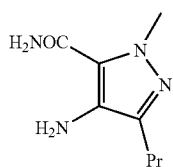

(vii) reacting compound 6 of step (vi) with a compound selected from the group consisting of substituted aryl and heterocyclic aldehydes in the presence of a solvent and $CuCl_2$ at a temperature ranging between 40 to 80° C. for a period ranging between 2 to 5 hr under oxygen atmosphere or under ordinary conditions to obtain compound of formula 1B;

Formula 1B

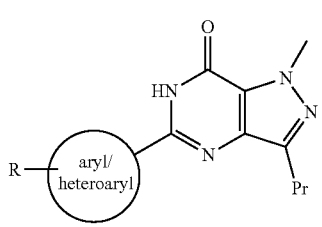

(viii) alternatively, reacting compound 6 of step (vi) with 2-ethoxybenzaldehyde to obtain 5-(2-ethoxyphenyl)-1-methyl-3-propyl-1H-pyrazolo[4,3-d]pyrimidin-7(6H)-one (compound 7);

(ix) treating compound 7 of step (viii) with chlorosulphonic acid to obtain 4-ethoxy-3-(6,7-dihydro-1-methyl-7-oxo-3-propyl-1H-pyrazolo[4,3-d]pyrimidin-5-yl)benzene-1-sulfonyl chloride (compound 8);

Compound 8

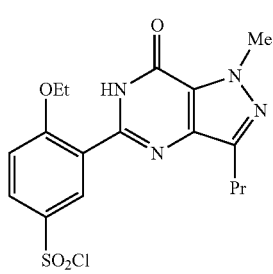

(x) reacting compound 8 of step (ix) with an amino compound selected from the group consisting of cyclic, acyclic, aliphatic, aromatic amino in the presence of a base in a solvent at a temperature ranging between 10 to 35° C. for a period ranging between 45 min to 4 hrs, adding cold water to quench the reaction and obtaining the compound of formula 1A Formula 1A

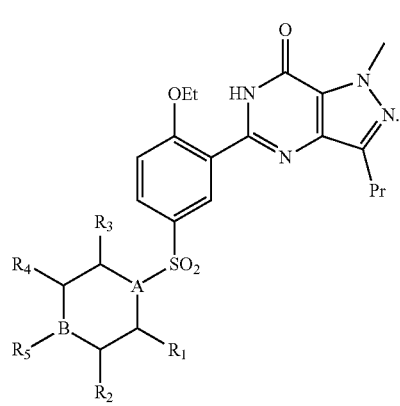

In an embodiment of the present invention there is provided a process for the preparation of pyrazolo-pyrimidinone compound, wherein the solvent is selected from the group consisting of DMF, DCM, $CHCl_3$, DCE, dioxane, acetonitrile, acetone and ethanol.

In still another embodiment of the present invention there is provided a process for the preparation of pyrazolo-pyrimidinone compound, wherein the base is selected from the group consisting of $K_2CO_3$, $Cs_2CO_3$, $Na_2CO_3$, TEA, TMA, DIPEA, Pyridine and DMAP.

In an embodiment of the present invention there is provided a pharmaceutical composition comprising an effective amount of the compound of formula 1, optionally along with the pharmaceutically acceptable salt, excipient, diluent, and carrier.

In another embodiment of the present invention there is provided a pharmaceutical composition, wherein pharmaceutically acceptable carrier containing aqueous solution is selected from the group consisting of water, buffered saline, glycol, glycerol, olive oil and liposome.

In still another embodiment of the present invention there is provided a pharmaceutical composition, wherein the dose of compound of formula 1 is ranging between 0.1 mg/kg to 100 mg/kg.

In an embodiment of the present invention there is provided a method of treating a subject in a need to cure or prevent erectile dysfunction comprising, administering the effective amount of compound of formula 1 or pharmaceutically acceptable salts thereof or a pharmaceutical composition containing either entity.

In another embodiment of the present invention there is provided a use of the compound as claimed in claim 1, or a pharmaceutically acceptable salt thereof, or a pharmaceutical composition containing either entity, for the treatment of erectile dysfunction in a male mammal, preferably human.

In yet another embodiment of the present invention there is provided a method of inhibiting PDE5 enzyme wherein the $IC_{50}$ value for compound of claim 1 ranges from 0.3 nM to 100 µM, wherein the in vivo activity of said compound is with the AUC range from 100 to 1000 at the dose of 3 mg/kg and it may vary with the dose pattern.

BRIEF DESCRIPTION OF ACCOMPANYING DRAWINGS

FIG. 1: Results of structural binding (in silico) studies of a representative compound viz. A) Sildenafil; (B) Compound Aa with PDE5 enzyme.

Figure 2A:
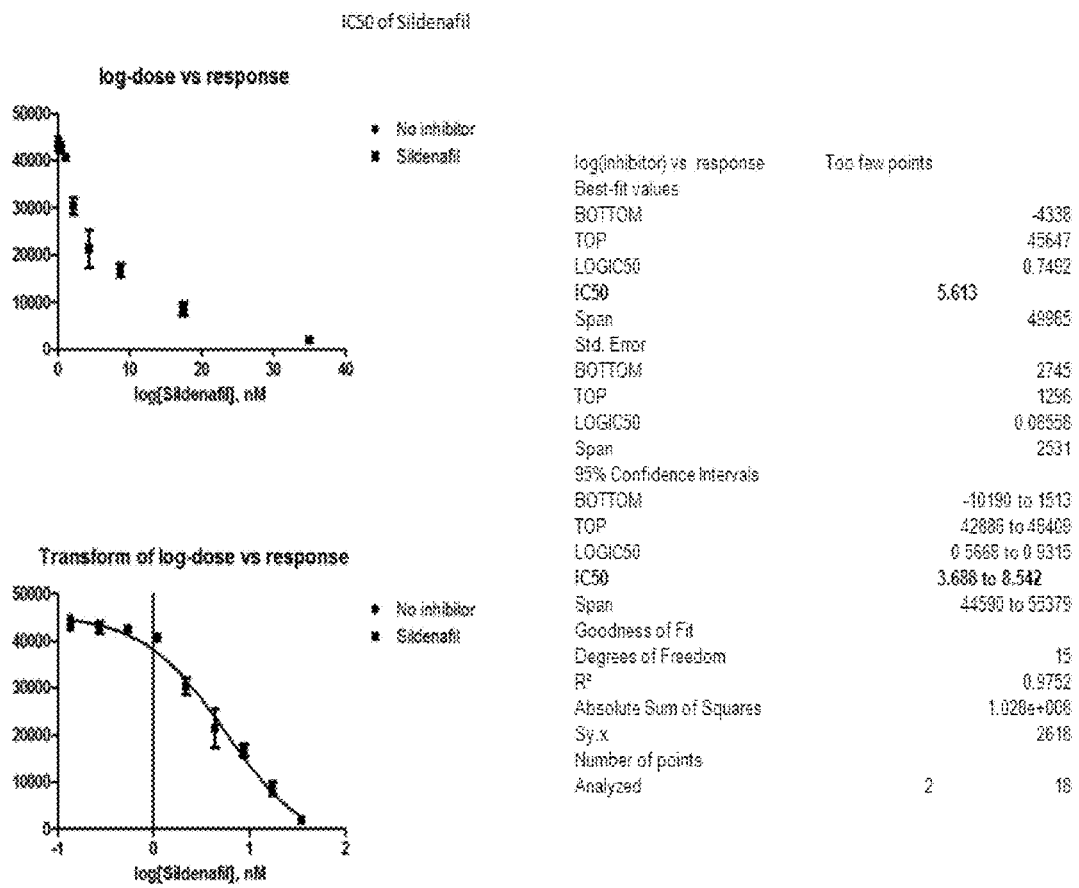
Figure 2B:
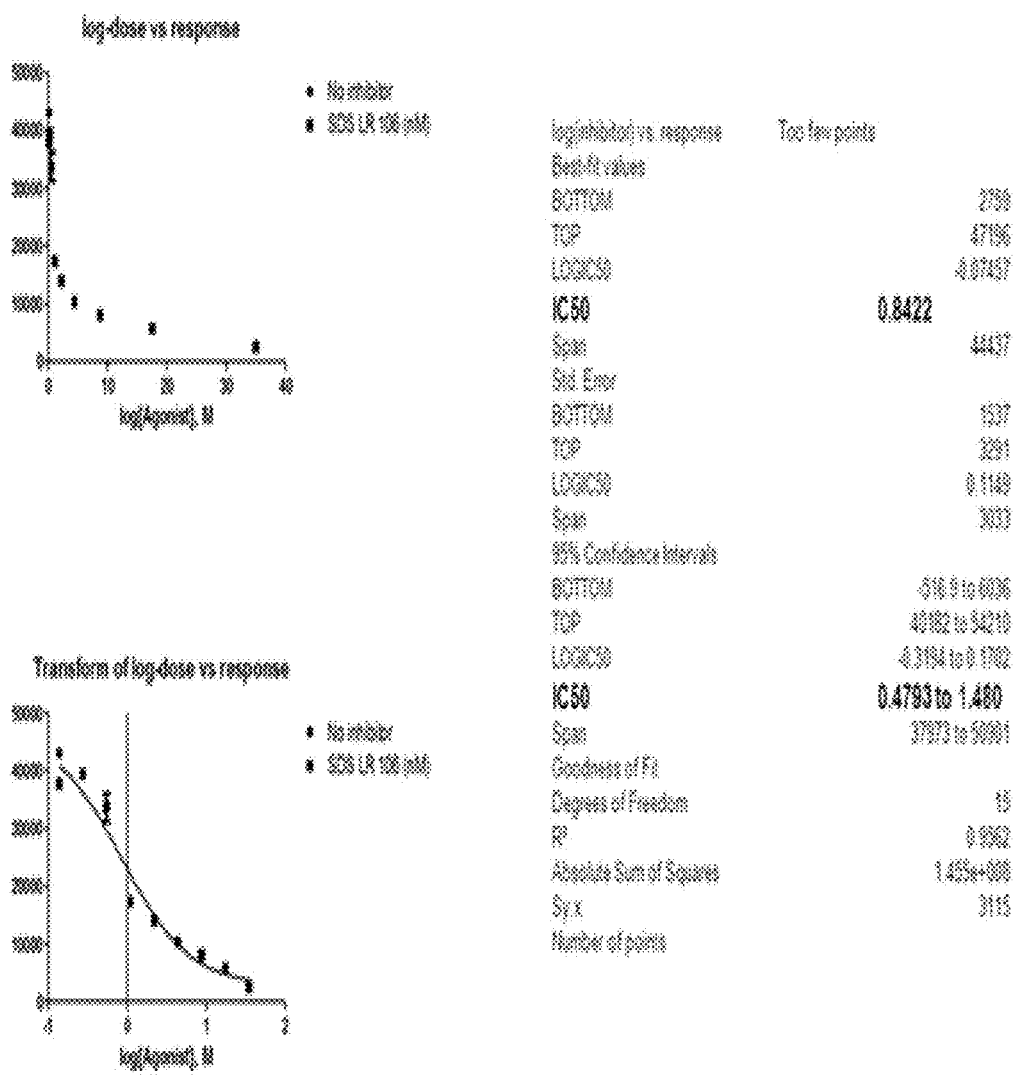

FIG. 2: Graph showing $IC_{50}$ value of (a) Sildenafil and (b) most potent PDE5 inhibitor i.e. 'Compound Aa' of the present invention.

Figure 3:
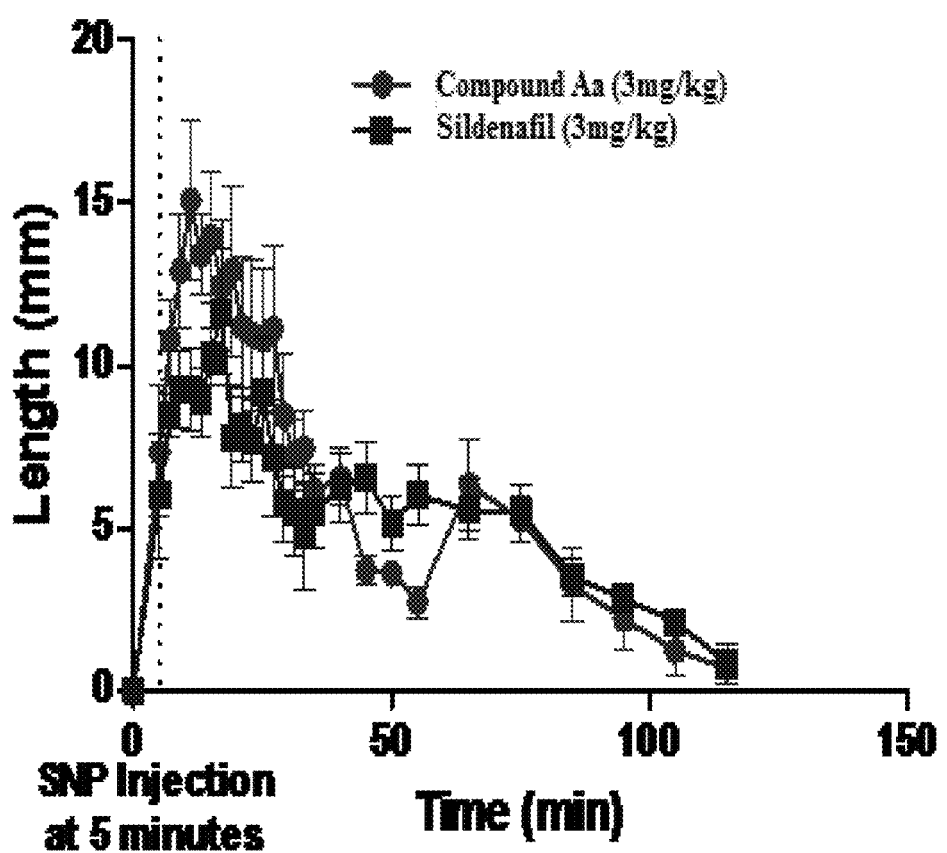

FIG. 3: In vivo study result for a representative compound Aa and comparative graph with reference molecule Sildenafil (Length of uncovered penile mucosa in rabbits was measured after intravenous administration of compound Aa (3 mg/kg) and Sildenafil (3 mg/kg) in a group of 5 animals each followed 5 mins later by an injection of Sodium nitroprusside (0.2 mg/kg). SNP alone was also used as a control and the values obtained were subtracted from both the molecules).

Figure 4:
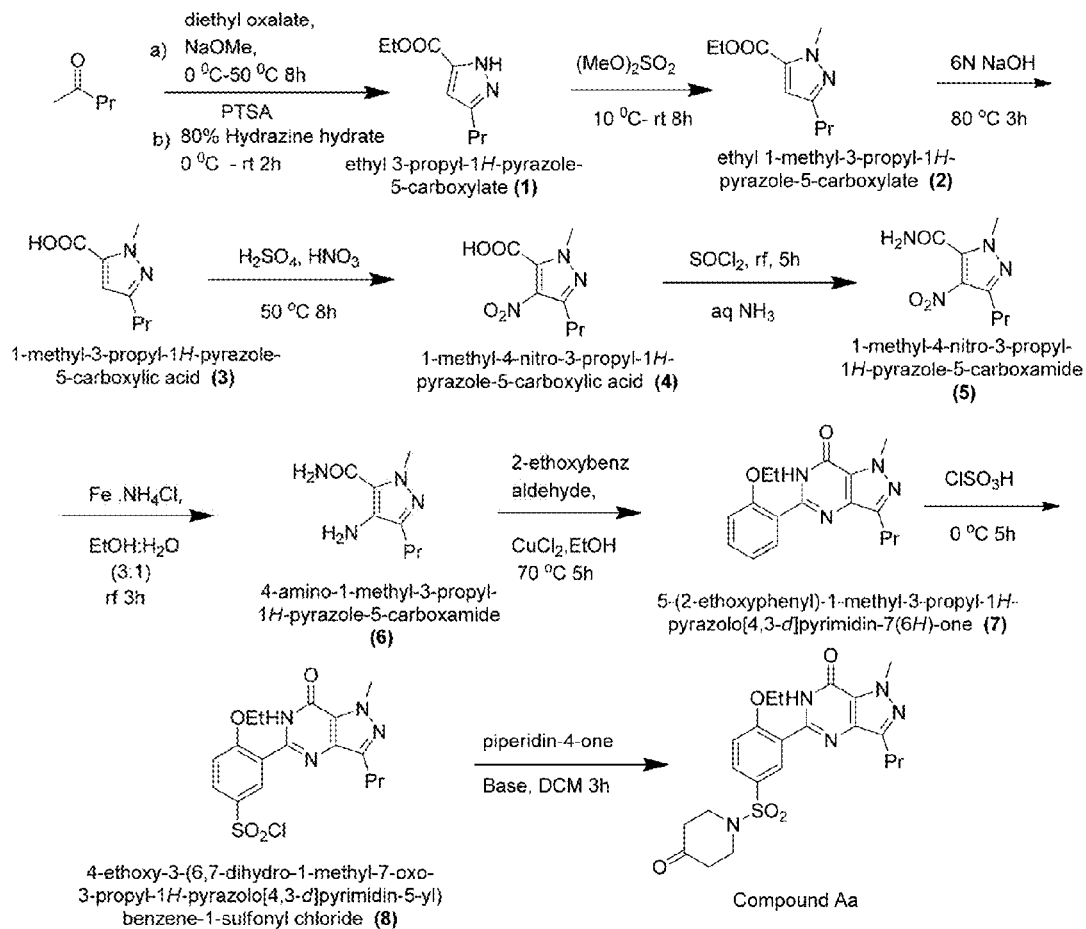
Figure 5:
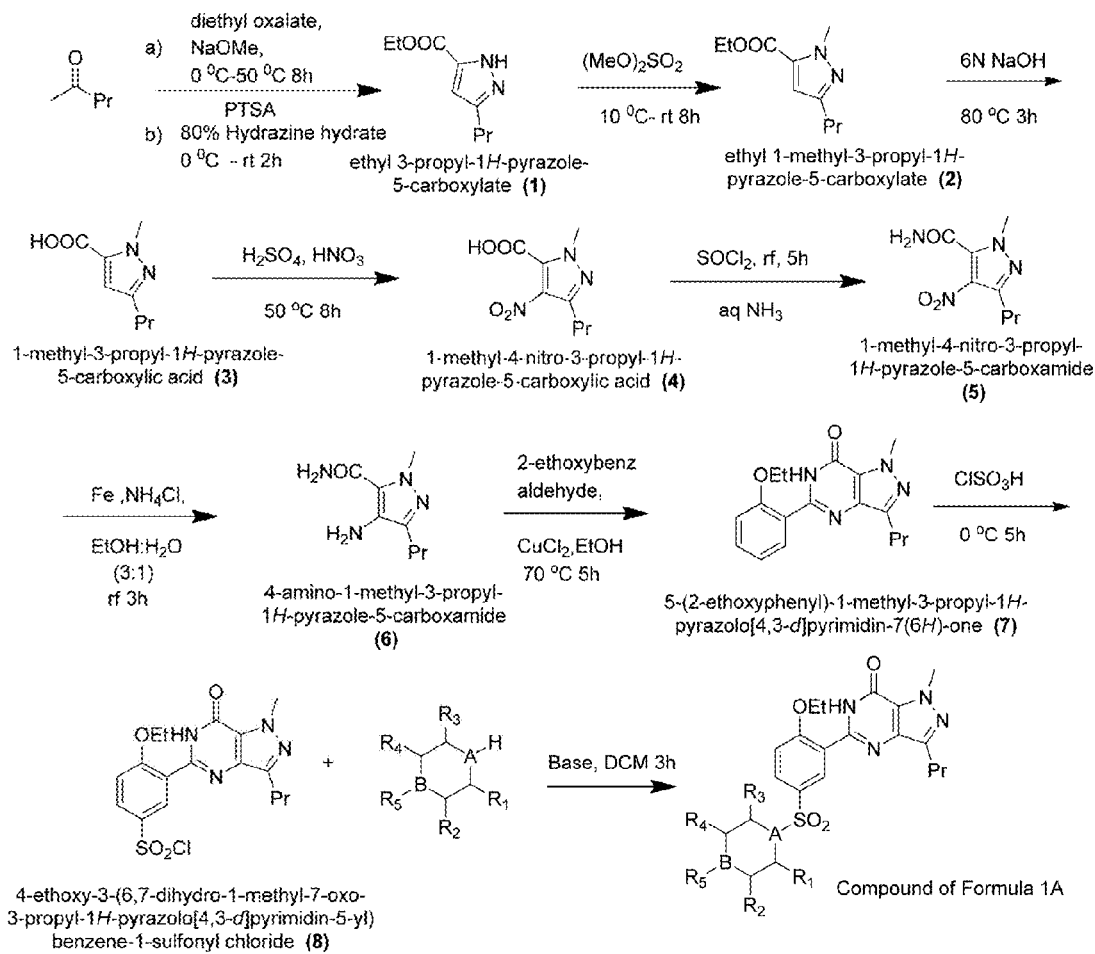
Figure 6:
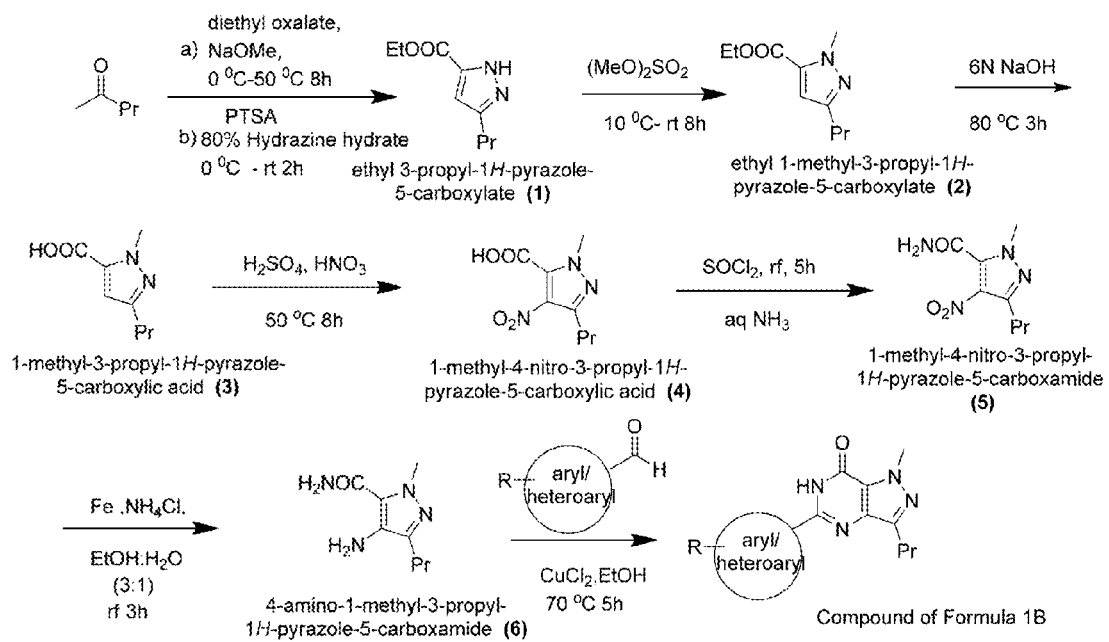

FIG. 4: Scheme for synthesis of compound Aa.
FIG. 5: Scheme for synthesis of compound of formula 1A.
FIG. 6: Scheme for synthesis of compound of formula 1B.

DETAILED DESCRIPTION OF THE INVENTION

The present invention relates to the pyrazolopyrimidinone scaffold that are well reported for their PDE5 (Phosphodiesterase) inhibitory activity. Sildenafil is the well known drug used for erectile dysfunction and it contains 5-(2-ethoxyphenyl)-1-methyl-3-propyl-1H-pyrazolo[4,3-d]pyrimidin-7(6H)-one as a active ingredient in Viagra.

This invention is based on the design, synthesis and biological evaluation of pyrazolopyrimidinone compounds and their pharmaceutical salts as PDE5 inhibitors and their use in the treatment of male erectile dysfunction and for the treatment of impotence.

The compound is presented as below in formula 1, wherein it contains the general structure as shown—

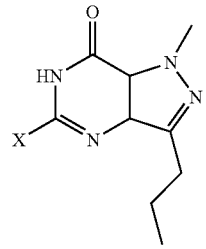

Formula 1 wherein, 'X' is selected from the group consisting of

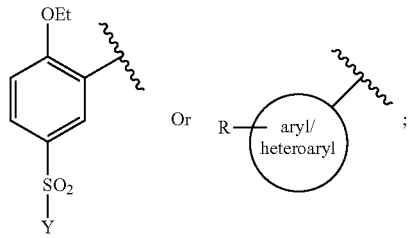

wherein, 'Y' is selected from

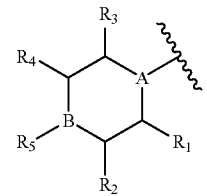

wherein, A, B, and $R_1$ to $R_5$ are independently selected from the groups described below;
wherein, A and B represents —N, —S, —CH, —CR, —NH, —NR;
wherein, R is BocHN, substituted aryl, heteroaryl, alkyl, heterocycloalkane with substitution selected from the group consisting of ketone, aryl, methyl, ethyl, propyl, butyl, pentyl, hexyl, heptyl, octyl, nonyl and decyl optionally having hydroxyl, amino, halo group at the terminal position of the carbon chain optionally having unsaturation on carbon chain at any position with different substitutions,
wherein, $R_1$ to $R_5$ are either independently selected from H, alkyl, aryl, halo, oxy, hydroxy, alkoxy, alkyl halide, alkyne ether, allyl ether, substituted alkene, amino, formyl, nitro with substitutions optionally having heteroaryl substitutions,
wherein, R in general represents an independently selected groups with substitutions on aryl ring selected from the group consisting of halo, alkoxy, nitro, amino, oxy, thio, carboxylic, formyl, hydroxyl, prenyl and isoprenyl,
wherein, the heteroaryl group is selected from the group consisting of pyridyl, furyl, thiphenyl, thiobenzyl, indolyl, thioindolyl, quinolyl, quinazolinyl, isoquinolyl, benzopyranyl, benzothiozolyl, benzooxazolyl, oxazolyl, triazolyl and tetrazolyl.

Further formula 1, is represented by the following structures

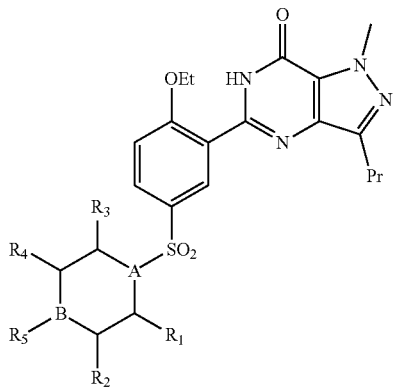

Formula 1A

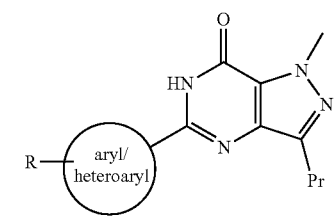

Formula 1B

Formula 1

In an embodiment of the present invention, Formula 1 comprises of two representative structures that independently represents different compounds based on pyrazolopyrimidinone scaffold. wherein, A and B represents —N, —S, —CH, —CR, —NH, —NR; wherein, R is BocHN, substituted aryl, heteroaryl, alkyl, heterocycloalkane with substitution selected from the group consisting of ketone, aryl, methyl, ethyl, propyl, butyl, pentyl, hexyl, heptyl, octyl, nonyl and decyl optionally having hydroxyl, amino, halo group at the terminal position of the carbon chain optionally having unsaturation on carbon chain at any position with different substitutions, wherein, $R_1$ to $R_5$ are either independently selected from H, alkyl, aryl, halo, oxy, hydroxy, alkoxy, alkyl halide, alkyne ether, allyl ether, substituted alkene, amino, formyl, nitro with substitutions optionally having heteroaryl substitutions, wherein, R in general represents an independently selected groups with substitutions on aryl ring selected from the group consisting of halo, alkoxy, nitro, amino, oxy, thio, carboxylic, formyl, hydroxyl, prenyl and isoprenyl, wherein, the heteroaryl group is selected from the group consisting of pyridyl, furyl, thiphenyl, thiobenzyl, indolyl, thioindolyl, quinolyl, quinazolinyl, isoquinolyl, benzopyranyl, benzothiozolyl, benzooxazolyl, oxazolyl, triazolyl and tetrazolyl.

In an another embodiment, all formulas (1A) in formula 1, represents 5-(2-ethoxyphenyl)-1-methyl-3-propyl-1H-pyrazolo[4,3-d]pyrimidin-7(6H)-one as common core in the structure and formula 1B represents aryl and heteroaryl pyrazolo pyrimidinone structures.

In yet another embodiment of the present invention, the formula 1B, having R on aryl, heteroaryl ring represents different substitutions selected from the group consisting of halo, alkyl, amino, substituted amino, nitro, carboxylates, ethers and arylethers.

In an embodiment of the present invention, the method used for the in silico bioinformatics study of pyrazolo pyrimidinone based compounds is preformed wherein all the computational studies were carried out in the Schrodinger suite 2010 molecular modeling software. The 2D structures of all the molecules were built in the maestro window (Maestro, version 9.2, Schrödinger, LLC, New York, N.Y., 2011). All the molecules were then converted to their respective 3D structure, with various conformers, tautomers and ionization states using the Ligprep and Confgen modules. (ConfGen, version 2.3, Schrödinger, LLC, New York, N.Y., 2011; LigPrep, version 2.5, Schrödinger, LLC, New York, N.Y., 2011; Watts, K. S.; Dalal, P.; Murphy, R. B.; Sherman, W.; Friesner, R. A.; Shelley, J. C.; "ConfGen: A Conformational Search Method for Efficient Generation of Bioactive Conformers," J. Chem. Inf. Model., 2010, 50, 534-546; Chen, I.; Foloppe, N.; "Drug-like Bioactive Structures and Conformational Coverage with the LigPrep/ConfGen Suite: Comparison to Programs MOE and Catalyst," J. Chem. Inf. Model., 2010, 50, 822-839.). The molecules were then minimized using the OPLS 2005 force field. The 3D crystal structure of PDE5 reported in Protein Data Bank (PDB) was used as receptor for docking studies (PDB ID: 1TBF for PDE5A) (Molecular Cell, 2004, 15, 279-286,). The protein was downloaded from the PDB and was prepared for docking using the Protein Preparation wizard. Hydrogen's were added to the protein and the missing loops were built. Bond length and bond order correction was also carried out for preparing the protein for docking studies. The active site grid was generated based on the already co-crystalised ligand of the receptor using receptor grid generation module. The ligands were docked on to the receptor through this grid using Glide module and flexible docking was carried out for all the conformers in order to find out the binding mode of these ligands. The extra precision (XP) scoring function of Glide was used for carrying out these studies. (Glide, version 5.6, Schrödinger, Inc., New York, N.Y., 2010; Friesner, R. A.; Banks, J. L.; Murphy, R. B.; Halgren, T. A.; Klicic, J. J.; Mainz, D. T.; Repasky, M. P.; Knoll, E. H.; Shaw, D. E.; Shelley, M.; Perry, J. K.; Francis, P.; Shenkin, P. S., "Glide: A New Approach for Rapid, Accurate Docking and Scoring. 1. Method and Assessment of Docking Accuracy," J. Med. Chem., 2004, 47, 1739-1749; Halgren, T. A.; Murphy, R. B.; Friesner, R. A.; Beard, H. S.; Frye, L. L.; Pollard, W. T.; Banks, J. L., "Glide: A New Approach for Rapid, Accurate Docking and Scoring. 2. Enrichment Factors in Database Screening," J. Med. Chem., 2004, 47, 1750-1759.).

In yet another embodiment of the present invention, the results obtained in the in silico studies of pyrazolo pyrimidinone based designer structures which is based on the docking studies showed that the molecule compound-Aa bind with better affinity to PDE5 when compared with sildenafil as standard (FIG. 1).

The process for the preparation of the compounds of formula 1 comprising formula 1A, wherein, the process comprises following steps—
  (i) reacting diethyl oxalate and 2-pentanone to obtain ethyl 3-propyl-1H-pyrazole-5-carboxylate (compound 1);
  (ii) reacting compound 1 of step (i) with dimethyl sulfate to obtain ethyl 1-methyl-3-propyl-1H-pyrazole-5-carboxylate (compound 2);
  (iii) treating compound 2 of step (ii) with NaOH solution to obtain 1-methyl-3-propyl-1H-pyrazole-5-carboxylic acid (compound 3);

(iv) reacting compound 3 of step (iii) with conc. H₂SO₄ and nitric acid to obtain 1-methyl-4-nitro-3-propyl-1H-pyrazole-5-carboxylic acid (compound 4);
(v) reacting compound 4 of step (iv) with SOCl₂ to obtain 1-methyl-4-nitro-3-propyl-1H-pyrazole-5-carboxamide (compound 5);
(vi) treating compound 5 of step (v) with EtOH:H₂O, Fe powder and NH₄Cl to obtain 4-amino-1-methyl-3-propyl-1H-pyrazole-5-carboxamide (compound 6);

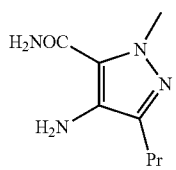

Compound 6

(vii) reacting compound 6 of step (vi) with a compound selected from the group consisting of substituted aryl and heterocyclic aldehydes in the presence of a solvent and CuCl₂ at a temperature ranging between 40 to 80° C. for a period ranging between 2 to 5 hr under oxygen atmosphere or under ordinary conditions to obtain compound of formula 1B;

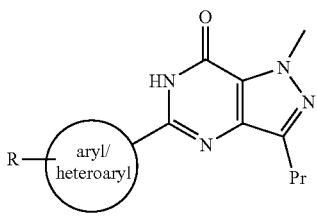

Formula 1B (viii) alternatively, reacting compound 6 of step (vi) with 2-ethoxybenzaldehyde to obtain 5-(2-ethoxyphenyl)-1-methyl-3-propyl-1H-pyrazolo[4,3-d]pyrimidin-7(6H)-one (compound 7);
(ix) treating compound 7 of step (viii) with chlorosulphonic acid to obtain 4-ethoxy-3-(6,7-dihydro-1-methyl-7-oxo-3-propyl-1H-pyrazolo[4,3-d]pyrimidin-5-yl)benzene-1-sulfonyl chloride (compound 8);

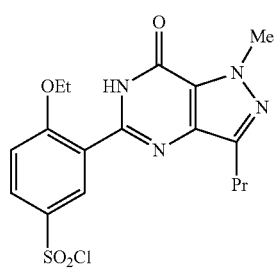

Compound 8

(x) reacting compound 8 of step (ix) with an amino compound selected from the group consisting of cyclic, acyclic, aliphatic, aromatic amino in the presence of a base in a solvent at a temperature ranging between 10 to 35° C. for a period ranging between 45 min to 4 hrs, adding cold water to quench the reaction and obtaining the compound of formula 1A

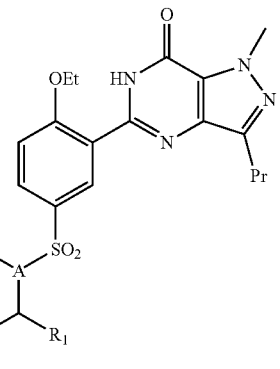

Formula 1A

In an another embodiment, the representative compounds of Formula 1A are selected from the group consisting of: 5-(2-ethoxy-5-((4-oxopiperidin-1-yl)sulfonyl)phenyl)-1-methyl-3-propyl-1H-pyrazolo[4,3-d]pyrimidin-7(6H)-one, 5-(2-ethoxy-5-((4-hydroxypiperidin-1-yl)sulfonyl)phenyl)-1-methyl-3-propyl-1H-pyrazolo[4,3-d]pyrimidin-7(6H)-one, 5-(2-ethoxy-5-((3-oxopiperazin-1-yl)sulfonyl)phenyl)-1-methyl-3-propyl-1H-pyrazolo[4,3-d]pyrimidin-7(6H)-one, 5-(2-ethoxy-5-((4-methoxypiperidin-1-yl)sulfonyl)phenyl)-1-methyl-3-propyl-1H-pyrazolo[4,3-d]pyrimidin-7(6H)-one, 5-(2-ethoxy-5-((4-(hydroxymethyl)piperidin-1-yl)sulfonyl) phenyl)-1-methyl-3-propyl-1H-pyrazolo[4,3-d]pyrimidin-7(6H)-one, 5-(2-ethoxy-5-((4-(2-hydroxyethyl)piperidin-1-yl)sulfonyl) phenyl)-1-methyl-3-propyl-1H-pyrazolo[4,3-d]pyrimidin-7(6H)-one, 5-(2-ethoxy-5-((4-(2-hydroxyphenyl)piperazin-1-yl)sulfonyl) phenyl)-1-methyl-3-propyl-1H-pyrazolo[4,3-d]pyrimidin-7(6H)-one), 5-(5-((4-(4-acetylphenyl)piperazin-1-yl)sulfonyl)-2-ethoxy phenyl)-1-methyl-3-propyl-1H-pyrazolo[4,3-d]pyrimidin-7(6H)-one, 5-(2-ethoxy-5-((4-(pyridin-4-yl)piperazin-1-yl) sulfonyl)phenyl)-1-methyl-3-propyl-1H-pyrazolo[4,3-d]pyrimidin-7(6H)-one, 5-(2-ethoxy-5-((4-(pyridin-2-yl) piperazin-1-yl)sulfonyl) phenyl)-1-methyl-3-propyl-1H-pyrazolo[4,3-d]pyrimidin-7(6H)-one, 5-(2-ethoxy-5-((4-(pyrimidin-2-yl)piperazin-1-yl)sulfonyl) phenyl)-1-methyl-3-propyl-1H-pyrazolo[4,3-d]pyrimidin-7(6H)-one, 5-(5-([1,4'-bipiperidin]-1'-ylsulfonyl)-2-ethoxyphenyl)-1-methyl-3-propyl-1H-pyrazolo[4,3-d]pyrimidin-7(6H)-one, 5-(5-((4-benzylpiperidin-1-yl)sulfonyl)-2-ethoxyphenyl)-1-methyl-3-propyl-1H-pyrazolo[4,3-d]pyrimidin-7(6H)-one, 5-(2-ethoxy-5-((4-methylpiperidin-1-yl)sulfonyl)phenyl)-1-methyl-3-propyl-1H-pyrazolo[4,3-d]pyrimidin-7(6H)-one, tert-butyl (1-((4-ethoxy-3-(1-methyl-7-oxo-3-propyl-6,7-dihydro-1H-pyrazolo[4,3-d]pyrimidin-5-yl)phenyl)sulfonyl) piperidin-4-yl)carbamate, 5-(5-((4-aminopiperidin-1-yl)sulfonyl)-2-ethoxyphenyl)-1-methyl-3-propyl-1H-pyrazolo[4,3-d]pyrimidin-7(6H)-one, 5-(2-ethoxy-5-((4-ethoxypiperidin-1-yl)sulfonyl)phenyl)-1-methyl-3-propyl-1H-pyrazolo[4,3-d]pyrimidin-7(6H)-one, 5-(5-((4-(allyloxy)piperidin-1-yl)sulfonyl)-2-ethoxyphenyl)-1-methyl-3-propyl-1H-pyrazolo[4,3-d]pyrimidin-7(6H)-one, 5-(2-ethoxy-5-((4-(prop-2-yn-1-yloxy)piperidin-1-yl)sulfonyl)phenyl)-1-methyl-3-propyl-1H-pyrazolo[4,3-d]pyrimidin-7(6H)-one, 5-(5-((4-(aminomethyl)piperidin-1-yl)sulfonyl)-2-ethoxyphenyl)-1-methyl-3-propyl-1H-pyrazolo[4,3-d]pyrimidin-7(6H)-one, 5-(2-ethoxy-5-((4-(pyrrolidin-1-yl) piperidin-1-yl)sulfonyl)phenyl)-1-methyl-3-propyl-1H-pyrazolo[4,3-d]pyrimidin-7(6H)-one, 5-(5-((4-(2-aminoethyl)piperidin-1-yl)sulfonyl)-2-ethoxyphenyl)-1- methyl-3-propyl-1H-pyrazolo[4,3-d]pyrimidin-7(6H)-one, 5-(2-ethoxy-5-((4-propoxypiperidin-1-yl)sulfonyl)phenyl)-1-methyl-3-propyl-1H-pyrazolo[4,3-d]pyrimidin-7(6H)-one, 5-(2-ethoxy-5-((4-isopropoxypiperidin-1-yl)sulfonyl)phenyl)-1-methyl-3-propyl-1H-pyrazolo[4,3-d]pyrimidin-7 (6H)-one, 5-(2-ethoxy-5-((4-(pyridin-3-yl)piperazin-1-yl)sulfonyl)phenyl)-1-methyl-3-propyl-1H-pyrazolo[4,3-d]pyrimidin-7(6H)-one, (E)-5-(5-((3-benzylidene-4-oxopiperidin-1-yl)sulfonyl)-2-ethoxyphenyl)-1-methyl-3-propyl-1H-pyrazolo[4,3-d]pyrimidin-7(6H)-one, (Z)-5-(5-((3-benzylidene-4-oxopiperidin-1-yl)sulfonyl)-2-ethoxyphenyl)-1-methyl-3-propyl-1H-pyrazolo[4,3-d]pyrimidin-7(6H)-one, (E)-5-(2-ethoxy-5-((3-(4-fluorobenzylidene)-4-oxopiperidin-1-yl)sulfonyl)phenyl)-1-methyl-3-propyl-1H-pyrazolo[4,3-d]pyrimidin-7(6H)-one, (Z)-5-(2-ethoxy-5-((3-(4-fluorobenzylidene)-4-oxopiperidin-1-yl)sulfonyl)phenyl)-1-methyl-3-propyl-1H-pyrazolo[4,3-d]pyrimidin-7(6H)-one, (E)-5-(2-ethoxy-5-((3-(4-methoxybenzylidene)-4-oxopiperidin-1-yl)sulfonyl)phenyl)-1-methyl-3-propyl-1H-pyrazolo[4,3-d]pyrimidin-7(6H)-one, (Z)-5-(2-ethoxy-5-((3-(4-methoxybenzylidene)-4-oxopiperidin-1-yl)sulfonyl)phenyl)-1-methyl-3-propyl-1H-pyrazolo[4,3-d]pyrimidin-7(6H)-one, (E)-5-(2-ethoxy-5-((3-(2-fluorobenzylidene)-4-oxopiperidin-1-yl)sulfonyl)phenyl)-1-methyl-3-propyl-1H-pyrazolo[4,3-d]pyrimidin-7 (6H)-one, (Z)-5-(2-ethoxy-5-((3-(2-fluorobenzylidene)-4-oxopiperidin-1-yl)sulfonyl)phenyl)-1-methyl-3-propyl-1H-pyrazolo[4,3-d]pyrimidin-7(6H)-one, (E)-5-(2-ethoxy-5-((3-(3-fluorobenzylidene)-4-oxopiperidin-1-yl)sulfonyl)phenyl)-1-methyl-3-propyl-1H-pyrazolo[4, 3-d]pyrimidin-7 (6H)-one, (Z)-5-(2-ethoxy-5-((3-(3-fluorobenzylidene)-4-oxopiperidin-1-yl)sulfonyl)phenyl)-1-methyl-3-propyl-1H-pyrazolo[4,3-d]pyrimidin-7(6H)-one, (E)-5-(2-ethoxy-5-((3-(3-methoxybenzylidene)-4-oxopiperidin-1-yl)sulfonyl)phenyl)-1-methyl-3-propyl-1H-pyrazolo[4, 3-d]pyrimidin-7 (6H)-one, (Z)-5-(2-ethoxy-5-((3-(3-methoxybenzylidene)-4-oxopiperidin-1-yl)sulfonyl)phenyl)-1-methyl-3-propyl-1H-pyrazolo[4,3-d]pyrimidin-7(6H)-one, (E)-5-(2-ethoxy-5-((3-(2-methoxybenzylidene)-4-oxopiperidin-1-yl)sulfonyl)phenyl)-1-methyl-3-propyl-1H-pyrazolo[4, 3-d]pyrimidin-7(6H)-one, (Z)-5-(2-ethoxy-5-((3-(2-methoxybenzylidene)-4-oxopiperidin-1-yl)sulfonyl)phenyl)-1-methyl-3-propyl-1H-pyrazolo[4,3-d]pyrimidin-7 (6H)-one, (E)-5-(2-ethoxy-5-((3-(2-ethoxybenzylidene)-4-oxopiperidin-1-yl)sulfonyl)phenyl)-1-methyl-3-propyl-1H-pyrazolo[4,3-d]pyrimidin-7(6H)-one, (Z)-5-(2-ethoxy-5-((3-(2-ethoxybenzylidene)-4-oxopiperidin-1-yl)sulfonyl)phenyl)-1-methyl-3-propyl-1H-pyrazolo[4,3-d]pyrimidin-7 (6H)-one, (E)-5-(2-ethoxy-5-((3-(4-ethoxybenzylidene)-4-oxopiperidin-1-yl)sulfonyl)phenyl)-1-methyl-3-propyl-1H-pyrazolo[4, 3-d]pyrimidin-7(6H)-one, (Z)-5-(2-ethoxy-5-((3-(4-ethoxybenzylidene)-4-oxopiperidin-1-yl)sulfonyl)phenyl)-1-methyl-3-propyl-1H-pyrazolo[4,3-d]pyrimidin-7 (6H)-one, (E)-5-(5-((3, 5-dimethoxybenzylidene)-4-oxopiperidin-1-yl)sulfonyl)-2-ethoxyphenyl)-1-methyl-3-propyl-1H-pyrazolo[4,3-d]pyrimidin-7(6H)-one, and (Z)-5-(5-((3-(3,5-dimethoxybenzylidene)-4-oxopiperidin-1-yl)sulfonyl)-2-ethoxyphenyl)-1-methyl-3-propyl-1H-pyrazolo[4,3-d]pyrimidin-7(6H)-one.

In yet another embodiment of the present invention, the representative compounds of Formula 1B are selected from the group consisting of: 5-(3-bromo-4-methoxyphenyl)-1-methyl-3-propyl-1H-pyrazolo[4, 3-d]pyrimidin-7(6H)-one, 1-methyl-5-(3-nitrophenyl)-3-propyl-1H-pyrazolo[4,3-d]pyrimidin-7(6H)-one, 5-(3-bromo-4-fluorophenyl)-1-methyl-3-propyl-1H-pyrazolo [4,3-d]pyrimidin-7(6H)-one, 1-methyl-5-(5-nitrofuran-2-yl)-3-propyl-1H-pyrazolo[4, 3-d] pyrimidin-7(6H)-one, 5-(4-hydroxyphenyl)-1-methyl-3-propyl-1H-pyrazolo[4,3-d] pyrimidin-7(6H)-one, 5-(4-methoxy-3-nitrophenyl)-1-methyl-3-propyl-1H-pyrazolo [4,3-d]pyrimidin-7(6H)-one, 5-(4-methoxyphenyl)-1-methyl-3-propyl-1H-pyrazolo[4,3-d] pyrimidin-7(6H)-one, 5-(4-chlorophenyl)-1-methyl-3-propyl-1H-pyrazolo[4, 3-d] pyrimidin-7(6H)-one, 1-methyl-3-propyl-5-(2,4,5-trimethoxyphenyl)-1H-pyrazolo [4,3-d]pyrimidin-7(6H)-one, 5-(3-fluoro-4-methoxyphenyl)-1-methyl-3-propyl-1H-pyrazolo[4,3-d]pyrimidin-7(6H)-one, 5-(3, 5-dimethoxyphenyl)-1-methyl-3-propyl-1H-pyrazolo[4,3-d]pyrimidin-7(6H)-one, 5-(3-chlorophenyl)-1-methyl-3-propyl-1H-pyrazolo[4,3-d] pyrimidin-7(6H)-one, 5-(2-fluorophenyl)-1-methyl-3-propyl-1H-pyrazolo[4,3-d] pyrimidin-7(6H)-one, 5-(3-fluorophenyl)-1-methyl-3-propyl-1H-pyrazolo[4,3-d] pyrimidin-7(6H)-one, 5-(4-hydroxy-3-nitrophenyl)-1-methyl-3-propyl-1H-pyrazolo[4,3-d]pyrimidin-7(6H)-one; 5-(3,4-dimethoxyphenyl)-1-methyl-3-propyl-1H-pyrazolo[4,3-d]pyrimidin-7(6H)-one, 5-(benzo[d][1,3]dioxol-5-yl)-1-methyl-3-propyl-1H-pyrazolo[4,3-d]pyrimidin-7(6H)-one, and 1-methyl-3-propyl-5-(pyridin-3-yl)-1H-pyrazolo[4, 3-d] pyrimidin-7(6H)-one.

EXAMPLES

The following examples are given by way of illustrating the present invention and should not be construed to limit the scope of the present invention:

The invention is further described by reference to following representative examples which are intended to illustrate, not to limit the scope of the invention.

As described in FIG. 4, the details of steps 1 to 8 are described below in Example 1, the synthetic procedure for these steps were used from the reported method (Peter J. Dunn, Org. Process Res. Dev. 2005, 9, 88-97) by employing minor modifications; and the step 9, the coupling of chlorosulphonyl intermediate with different amino groups is also described for some representative compounds.

Example 1: Representative and Typical Procedure for Synthesis of Compound Aa

The steps involved for the synthesis of compound Aa are described as below (FIG. 4), as representative example. The steps 1 to 8 are used as per literature reported method (Peter J. Dunn, Org. Process Res. Dev. 2005, 9, 88-97.)

Step 1

Synthesis of ethyl 3-propyl-1H-pyrazole-5-carboxylate:—Diethyl oxalate (20 gm 13.7 m·ml) and 2-pentanone (11.8 gm 13.7 m·ml) are mixed and then the reaction mix is cooled to 2° C. and sodium methoxide (8.12 gm 15.0 m. ml) are added in four portions of each according to the following procedure. The first lot of sodium methoxide (4.03 gm) is added at 0° C. to the mixture maintained over an ice bath at 5-0° C., then the temperature is allowed to reach 40° C. and when stabilized the ice bath is removed and the reaction mixture is stirred for 30 minutes and cooled again to 5° C. over an ice bath. The second lot of sodium methoxide (4.03 gm) is added at 5° C. to the mixture kept over an ice bath at 5° C. for 10 minutes, the temperature is allowed to reach 40° C. and when stabilized the ice bath is removed and the reaction mixture is stirred for 30 minutes and cooled again to 5° C. over an ice bath. The third lot of sodium methoxide (4.03 gm) is added at 5° C. to the mixture kept over an ice bath at 5° C. for 10 minutes, the temperature is allowed to reach 40° C. and when stabilized the ice bath is removed, the reaction mixture is stirred for 30 minutes and cooled again to 5° C. over an ice bath. The fourth lot of sodium methoxide (4.03 gm) is added at 5° C. to the mixture kept over an ice bath at 5° C. for 10 minutes, the temperature is allowed to reach 55° C. stirred for 2 hours at 55° C. and the mixture is cooled at 10° C. and 300 ml ethyl acetate is added, stirred for 20 minutes and added water to the reaction mixture. Then the pH of the reaction mixture is adjusted to 1.8-2.0 by adding 6N HCl solution, stirred for 15 minutes and the layers are separated. The aqueous layer is re-extracted with 2×100 ml ethyl acetate two times and obtained organic layers are combined together and washed with brine solution. Solid PTSA (0.59 gm) are added to the organic phase cooled to 5° C., then the reaction temperature is slowly raised to 10° C. and (4.4 ml 16.7 m·ml) hydrazine hydrate (80%) are added in a period of 1 hour while the temperature is not to exceed 25° C. The reaction mixture is then stirred for 45 min at 25° C., cooled to 5° C. and added 150 ml water. Then the pH is adjusted to 7.2 by adding 30% NaOH solution. The layers were separated and the aqueous solution was re-extracted with 100 ml ethylacetate. The combined organic layer are washed with brine solution, concentrated under vacuum till dryness. Yield 95%. $^1$H NMR (400 MHz, CDCl$_3$) δ 11.33 (s, 1H), 7.16 (s, 1H), 4.30 (q, J=7.0 Hz 3H), 2.50 (t J=7.6 Hz 3H) 1.70 (m 2H) 1.39 (t J=7.0 Hz) 1.02 (1 J=7.6 Hz 3H). ppm. MASS: ESI [M+H]$^+$: 183.12

Step 2

Synthesis of ethyl 1-methyl-3-propyl-1H-pyrazole-5-carboxylate:—Take ethyl 3-propyl-1H-pyrazole-5-carboxylate (20 gm 10.9 m·ml) in round bottom flask cooled to 5° C. and then added dimetyl sulfate (10.93 ml 11.5 m·ml) over a period of 1 h. The temperature is allowed to reach 25° C. and it is kept under stirring for 8 hours. Then it is cooled to 10° C. by adding 200 ml DCM, 100 ml water. The pH is adjusted to 7-7.3 by adding 30% NaOH solution while the temperature is kept below 15° C. After stirring for 15 minutes the layers are separated and water layer re-extracted with 2×50 ml DCM. The organic phase distilled under vacuum at 30° C.; Yield 95%. $^1$H NMR (400 MHz, CDCl$_3$) 6.8 (s, 1H), 4.30 (q, J=7.0 Hz 3H), 4.15 (s, 3H) 2.50 (t, J=7.6 Hz 3H) 1.70 (m, 2H) 1.39 (t, J=7.0 Hz) 1.02 (t, J=7.6 Hz 3H). ppm. MASS: ESI [M+H]$^+$: 197.12

Step 3

Synthesis of 1-methyl-3-propyl-1H-pyrazole-5-carboxylic acid:—Ethyl 1-methyl-3-propyl-1H-pyrazole-5-carboxylate (19 gm 9.6 mml) was suspended in 6N NaOH solution (48 ml 20.0 m·ml). The mixture was heated to 75° C. for 3 hours then cooled to 20° C., diluted with 50 ml water and acidified with conc. HCl. Filtration gave the carboxylic acid as pale brown compound; Yield 90%. $^1$H NMR (400 MHz, CDCl$_3$) δ 9.15 (br s 1H) 6.8 (s, 1H), 4.15 (s, 3H) 2.50 (t, J=7.6 Hz 3H) 1.75 (m 2H) 0.98 (t J=7.6 Hz 3H). ppm. MASS: ESI [M+Na]$^+$: 191.09

Step 4

Synthesis of 1-methyl-4-nitro-3-propyl-1H-pyrazole-5-carboxylic acid:—Dissolve 1-methyl-3-propyl-1H-pyrazole-5-carboxylic acid (13.0 gm 7.7 m·ml) in 20 ml of conc. H$_2$SO$_4$ and heated at 50° C. After that nitric mixture (9 ml) was added slowly over an 1 hour after the addition mixture was stirred at 50° C. for 7 hours and then cooled to room temperature before being poured onto ice. Filteration of the precipitate gave the nitropyrazole as a white solid; Yield 88%. $^1$H NMR (400 MHz, CDCl$_3$) δ 4.10 (s, 3H) 2.50 (t, J=7.6 Hz, 3H) 1.70 (m 2H) 1.02 (t, J=7.6 Hz, 3H) ppm ESI [M+Na]$^+$: 236.07

Step 5

Synthesis of 1-methyl-4-nitro-3-propyl-1H-pyrazole-5-carboxamide:—1-methyl-4-nitro-3-propyl-1H-pyrazole-5-carboxylic acid (14.0 gm 6.5 m·ml) was added to SOCl$_2$ (25 ml) and the resulting mixture heated under reflux for 5 hours. The reaction mixture was then cooled and excess SOCl$_2$ removed by evaporation under vacuum. The oily residue was dissolved in dry acetone (25 ml) and the solution was cautiously added to a mixture of ice and con aqueous ammonium hydroxide solution (40 ml). The precipitate was collected by filtration to provide the 1-methyl-4-nitro-3-propyl-1H-pyrazole-5-carboxamide as a pale yellow solid; Yield 90%. $^1$H NMR (400 MHz, CDCl$_3$) δ 9.15 (br. s 1H) 8.75 (s, 2H) 4.10 (s, 3H) 2.50 (t, J=7.6 Hz 3H) 1.70 (m 2H) 1.02 (t, J=7.6 Hz 3H). MASS: ESI [M+Na]$^+$: 214.07

Step 6

Synthesis of 4-amino-1-methyl-3-propyl-1H-pyrazole-5-carboxamide:—1-methyl-4-nitro-3-propyl-1H-pyrazole-5-carboxamide (11.0 gm 5.1 m·ml) was dissolved in 40 ml EtOH/H$_2$O (3:1), added Fe powder (8.7 gm 15.5 m·ml) and NH$_4$Cl (2.75 gm 5.1 m·ml). The mixture was heated up to 80° C. for 4.5 hours. The reaction mixture was cooled to 25° C. and filtered through celite and filterate was concentrated under vacuum. Trituration of the residue with either gave the 4-amino-1-methyl-3-propyl-1H-pyrazole-5-carboxamide as an off-white solid; Yield 88%. $^1$H NMR (400 MHz, CDCl$_3$) δ 9.01 (s, 2H) 6.6 (s, 2H) 4.10 (s, 3H) 2.50 (t, J=7.6 Hz 3H) 1.70 (m, 2H) 1.02 (t, J=7.6 Hz, 3H). MASS: ESI [M+H]$^+$: 183.14

Step 7

Synthesis of 5-(2-ethoxyphenyl)-1-methyl-3-propyl-1H-pyrazolo[4,3-d]pyrimidin-7(6H)-one:—4-amino-1-methyl-3-propyl-1H-pyrazole-5-carboxamide (7.0 gm 3.84 m·ml) and 2-ethoxybenz-aldehyde (6.0 gm 4.0 m·ml) were suspended in ethanol and the mixture was heated at 70° C. for 1.5 hours after conformation of forming of imine by TLC. Added CuCl$_2$ (15.4 gm 11.5 m ml) and the reaction mixture heated at 70° C. under O$_2$ for 1.5 hours. After there action was completed, the ethanol was removed under vacuum. Then work up was carried out using ethyl acetate and water. The organic layer was separated and water layer re-extracted with 100 ml ethyl acetate. The combined organic layers are washed with brine solution, concentrated under vacuum; Yield 83%. $^1$H NMR (400 MHz CDCl$_3$): δ; 10.80 (s 1H), 8.46 (m 1H), 7.47 (m 1H), 7.14 (m 1H) 7.06 (m 1H) 4.38 (q, J=7.0 Hz 2H), 4.27 (s 3H), 2.94 (t, J=7.6 Hz 2H), 1.87 (m 2H), 1.64 (t, J=7.0 Hz 3H). 1.03 (tJ=7.2 Hz 3H). ppm MASS: ESI [M+H]$^+$: 313.14

Step 8

Synthesis of 4-ethoxy-3-(6, 7-dihydro-1-methyl-7-oxo-3-propyl-1H-pyrazolo[4, 3-d] pyrimidin-5-yl) benzene-1-sulfonyl chloride:—To the chlorosulphonic acid (10 eq) was added 5-(2-ethoxyphenyl)-1-methyl-3-propyl-1H-pyrazolo[4,3-d]pyrimidin-7(6H)-one (1 eq) while maintaining the temperature 0° C. Then reaction was allowed to proceed at 5° C. until TLC analysis indicated the absence of starting material. After the reaction was completed then cooled CHCl$_3$ and ice in ice bath was added to the reaction mixture. Organic layer was separated. Water layer was re-extracted with 2×100 ml cold CHCl$_3$ and the combined organic layer are washed with brine solution, concentrated under vacuum; Yield 75%. $^1$H NMR (400 MHz, CDCl$_3$) δ 10.78 (s 1H), 8.72 (d, J=1.4 Hz, 1H), 8.04 (dd, J=7.5, 1.4 Hz, 1H), 7.33 (d, J=7.5 Hz, 1H), 4.38 (q J=6.8 Hz 2H), 4.27 (s 3H), 2.92 (t J=7.6 Hz 2H), 1.87 (m 2H), 1.65 (t J=6.8 Hz 3H). 1.02 (t J=7.2 Hz 3H). ESI [M+H]$^+$: 411.13

Step 9: Synthesis of compound Aa (5-(2-ethoxy-5-((4-oxopiperidin-1-yl)sulfonyl)phenyl)-1-methyl-3-propyl-1H-pyrazolo[4,3-d]pyrimidin-7(6H)-one)

Piperidin-4-one (1 eq) was dissolved in dry DCM and added DIPEA (3 eq), stirred the reaction mixture for 10 minutes at 15° C., added 4-ethoxy-3-(1-methyl-7-oxo-3-propyl-6,7-dihydro-1H-pyrazolo[4,3-d]pyrimidin-5-yl)benzene-1-sulfonyl chloride (1 eq) and stirred the reaction for 6 hours at 25° C. After completion of the reaction, added 30 ml DCM, 30 ml water organic layer was separated. Water layer re-extracted with 20 ml DCM and the combined organic layer are washed with brine solution, concentrated under vacuum Yield 90%. $^1$H NMR (400 MHz CDCl$_3$): δ; 10.78 (s, 1H), 8.87 (d, J=2.4 Hz, 1H), 7.88 (dd, J=8.8, 2.4 Hz, 1H), 7.17 (d, J=8.8 Hz, 1H), 4.38 (q, J=6.8 Hz, 2H), 4.27 (s, 3H), 3.48 (t, J=6.2 Hz, 4H), 2.92 (t, J=7.6 Hz, 2H), 2.57 (t, J=6.2 Hz, 4H), 1.87 (m, 2H), 1.65 (t, J=6.8 Hz, 3H). 1.02 (t, J=7.2 Hz, 3H). MASS: ESI [M+Na]$^+$: 496.00

All the compounds of formula 1A mentioned below are prepared by employing the similar method for step 1 to step 8 containing different substitutions at R and R1 to R5 positions, as described for the preparation of compound Aa. The intermediates from 1 to 8 are prepared as per the literature reported methods (Peter J. Dunn, Org. Process Res. Dev. 2005, 9, 88-97). Furthermore, the procedure for step 9 is provided for some representative examples, the similar conditions are used for all the examples.

Example 2: Compound Ab (5-(2-ethoxy-5-((4-hydroxypiperidin-1-yl)sulfonyl)phenyl)-1-methyl-3-propyl-1H-pyrazolo[4,3-d]pyrimidin-7(6H)-one)

Synthesis of Ab; Step 9:
Dissolve 4-Hydroxypiperidine (1 eq) dry DCM and added DIPEA (3 eq) stirred the reaction mixture for 10 minutes at 15° C., added 4-ethoxy-3-(1-methyl-7-oxo-3-propyl-6,7-dihydro-1H-pyrazolo[4,3-d]pyrimidin-5-yl)benzene-1-sulfonyl chloride (1 eq) and stirred the reaction for 4 hours at 25° C. After completion of the reaction, added 30 ml DCM, 30 ml water organic layer was separated. Water layer was re-extracted with 20 ml DCM and the combined organic layer are washed with brine solution, concentrated under vacuum. The residue was purified by column chromatography on silica the desired product Ab as a white solid; yield 88%.
$^1$H NMR (500 MHz CDCl$_3$): δ; 10.84 (s 1H), 8.83 (d, J=2.4 Hz 1H), 7.84 (ddJ=8.8, 2.4 Hz 1H), 7.17 (d J=8.8 Hz 1H), 4.34 (q J=6.8 Hz 2H), 4.27 (s, 3H), 3.8 (bs 1H), 3.61 (1 J=7.6 Hz 2H) 2.97-2.90 (m 4H), 1.96 (m 2H), 1.87 (m 2H), 1.69-1.63 (m, 5H) 1.02 (t J=7.2 Hz 3H). MASS: ESI [M+Na]$^+$: 498.00. Elemental anal. calcd. for C$_{22}$H$_{29}$N$_5$O$_5$S; C, 55.56; H, 6.15; N, 14.73; O, 16.82; S, 6.74; found C, 55.46; H, 6.25; N, 14.63; O, 16.87; S, 6.79.

Example 3: Compound Ac (5-(2-ethoxy-5-((3-oxopiperazin-1-yl)sulfonyl)phenyl)-1-methyl-3-propyl-1H-pyrazolo[4,3-d]pyrimidin-7(6H)-one)

Synthesis of Ac; Step 9:
Dissolve 2-Oxopiperazine (1 eq) dry CHCl$_3$ and added TEA (3 eq), stirred the reaction mixture for 10 minutes at 10° C., added 4-ethoxy-3-(1-methyl-7-oxo-3-propyl-6, 7-dihydro-1H-pyrazolo[4,3-d]pyrimidin-5-yl)benzene-1-sulfonyl chloride (1 eq) and stirred the reaction for 6 hours at 25° C. After completion of the reaction, added 30 ml CHCl$_3$, 30 ml water organic layer was separated. Water layer was re-extracted with 20 ml CHCl$_3$ and the combined organic layer are washed with brine solution, concentrated under vacuum. The residue was purified by column chromatography on silica the desired product Ac as a white solid; yield 95%.
$^1$H NMR (400 MHz, CDCl$_3$) δ 10.88 (s, 1H), 8.82 (d, J=2.4 Hz, 1H), 7.88 (dd, J=8.8, 2.4 Hz, 1H), 7.19 (d, J=8.8 Hz, 1H), 6.43 (s, 1H), 4.39 (q, J=6.9 Hz, 2H), 4.28 (s, 3H), 3.74 (s, 2H), 3.54-3.44 (m, 2H), 3.43-3.34 (m, 2H), 2.94 (t, J=7.5 Hz, 2H), 1.86 (m, 2H), 1.65 (t, J=7.0 Hz, 3H), 1.03 (t, J=7.4 Hz, 3H). MASS: ESI [M+Na]$^+$: 497.00. Elemental anal. calcd. for C$_{21}$H$_{26}$N$_6$O$_5$S; C, 53.15; H, 5.52; N, 17.71; O, 16.86; S, 6.76; found C, 53.10; H, 5.58; N, 17.76; O, 16.86; S, 6.70.

Example 4: Compound Ad (5-(2-ethoxy-5-((4-methoxypiperidin-1-yl)sulfonyl)phenyl)-1-methyl-3-propyl-1H-pyrazolo[4,3-d]pyrimidin-7(6H)-one)

Synthesis of Ad; Step 9:
Dissolve 4-methoxypiperidine (1 eq) dry acetone and added K$_2$CO$_3$ (3 eq) stirred the reaction mixture for 10 minutes at 20° C., added 4-ethoxy-3-(1-methyl-7-oxo-3-propyl-6,7-dihydro-1H-pyrazolo[4,3-d]pyrimidin-5-yl)benzene-1-sulfonyl chloride (1 eq) and stirred the reaction for 5 hours at 35° C. After completion of the reaction remove the acetone under vacuum added 30 ml DCM, 30 ml water organic layer was separated. Water layer was re-extracted with 20 ml DCM and the combined organic layer are washed with brine solution, concentrated under vacuum. The residue was purified by column chromatography on silica the desired product Ad as a white solid; yield 90%.
$^1$H NMR (400 MHz, CDCl$_3$) δ 10.84 (s, 1H), 8.83 (d, J=2.4 Hz, 1H), 7.84 (dd, J=8.7, 2.4 Hz, 1H), 7.15 (d, J=8.7 Hz, 1H), 4.38 (q, J=7.0 Hz, 2H), 4.28 (s, 3H), 3.34-3.28 (m, 1H), 3.26 (s, 3H), 3.18 (m 2H), 3.12-3.04 (m, 2H), 2.93 (t, J=7.5 Hz, 2H), 1.95-1.71 (m, 6H), 1.65 (t, J=7.0 Hz, 3H), 1.03 (t, J=7.4 Hz, 3H). MASS: ESI [M+H]$^+$: 490.10. Elemental anal. calcd. for C$_{23}$H$_{31}$N$_5$O$_5$S; C, 56.42; H, 6.38; N, 14.30; O, 16.34; S, 6.55; found C, 56.52; H, 6.33; N, 14.35; O, 16.27; S, 6.52.

Example 5: Compound Ae (5-(2-ethoxy-5-((4-(hydroxymethyl)piperidin-1-yl)sulfonyl) phenyl)-1-methyl-3-propyl-1H-pyrazolo[4,3-d]pyrimidin-7(6H)-one)

Synthesis of Ae; Step 9:
Dissolve 4-piperidinylmethanol (1 eq) dry DCM and added DMAP (3 eq) stirred the reaction mixture for 10 minutes at 20° C., added 4-ethoxy-3-(1-methyl-7-oxo-3-propyl-6,7-dihydro-1H-pyrazolo[4,3-d]pyrimidin-5-yl)benzene-1-sulfonyl chloride (1 eq) and stirred the reaction for 3 hours at 35° C. After completion of the reaction, added 30 ml DCM, 30 ml water organic layer was separated. Water layer was re-extracted with 20 ml DCM and the combined organic layer are washed with brine solution, concentrated under vacuum. The residue was purified by column chromatography on silica the desired product Ae as a white solid; yield 85%.

$^1$H NMR (400 MHz, CDCl$_3$) δ 10.82 (s, 1H), 8.82 (d, J=2.3 Hz, 1H), 7.85 (dd, J=8.7, 2.3 Hz, 1H), 7.15 (d, J=8.8 Hz, 1H), 4.38 (q, J=6.9 Hz, 2H), 4.27 (s, 3H), 3.89 (d, J=11.6 Hz, 2H), 3.49 (m, 2H), 2.93 (t, J=7.5 Hz, 2H), 2.37 (m, 2H), 1.84 (m, 2H), 1.67 (t, J=6.9 Hz 3H), 1.51-1.12 (m, 5H), 1.03 (t, J=7.4 Hz, 3H). MASS: ESI [M+H]$^+$: 490.05. Elemental anal. calcd. for C$_{23}$H$_{31}$N$_5$O$_5$S; C, 56.42; H, 6.38; N, 14.30; O, 16.34; S, 6.55; found C, 56.47; H, 6.33; N, 14.35; O, 16.36; S, 6.53.

Example 6: Compound Af (5-(2-ethoxy-5-((4-(2-hydroxyethyl)piperidin-1-yl)sulfonyl) phenyl)-1-methyl-3-propyl-1H-pyrazolo[4,3-d]pyrimidin-7(6H)-one)

Synthesis of Af; Step 9:

Dissolve the amine 2-(4-piperidinly)ethanol (1 eq) dry DCE and added DIPEA (3 eq) stirred the reaction mixture for 10 minutes at 18° C., added 4-ethoxy-3-(1-methyl-7-oxo-3-propyl-6, 7-dihydro-1H-pyrazolo[4,3-d]pyrimidin-5-yl)benzene-1-sulfonyl chloride (1 eq) and stirred the reaction for 4.5 hours at 35° C. After completion of the reaction, added 30 ml DCM, 30 ml water organic layer was separated. Water layer was re-extracted with 20 ml DCM and the combined organic layer are washed with brine solution, concentrated under vacuum. The residue was purified by column chromatography on silica the desired product Af as a white solid; yield 85%. $^1$H NMR (400 MHz, CDCl$_3$) δ 10.83 (s, 1H), 8.82 (d, J=2.3 Hz, 1H), 7.84 (dd, J=8.7, 2.4 Hz, 1H), 7.15 (d, J=8.8 Hz, 1H), 4.38 (q, J=7.0 Hz, 2H), 4.27 (s, 3H), 3.83 (d, J=11.8 Hz, 2H), 3.66 (t, J=6.3 Hz, 2H), 2.93 (t, J=7.5 Hz, 2H), 2.35 (t, J=11.5 Hz, 2H), 1.86 (m 2H), 1.77 (d, J=11.5 Hz, 2H), 1.65 (t, J=7.0 Hz 3H), 1.50 (m, 2H), 1.14-1.25 (m 3H) 1.03 (t, J=7.4 Hz, 3H). MASS: ESI [M+H]$^+$: 504.05. Elemental anal. calcd. for C$_{24}$H$_{33}$N$_5$O$_5$S; C, 57.24; H, 6.60; N, 13.91; O, 15.88; S, 6.37; found C, 57.34; H, 6.55; N, 13.84; O, 15.95; S, 6.32.

Example 7: Compound Ag (5-(2-ethoxy-5-((4-(2-hydroxyphenyl)piperazin-1-yl)sulfonyl) phenyl)-1-methyl-3-propyl-1H-pyrazolo[4,3-d]pyrimidin-7(6H)-one)

Synthesis of Ag; Step 9

Dissolve 2-(1-piperazinyl)phenol (1 eq) dry DCM and added Pyridine (2 eq) stirred the reaction mixture for 10 minutes at 25° C., added 4-ethoxy-3-(1-methyl-7-oxo-3-propyl-6,7-dihydro-1H-pyrazolo[4,3-d]pyrimidin-5-yl)benzene-1-sulfonyl chloride (1 eq) and stirred the reaction for 5.5 hours at 25° C. After completion of the reaction, added 30 ml DCM, 30 ml water organic layer was separated. Water layer was re-extracted with 20 ml DCM and the combined organic layer are washed with brine solution, concentrated under vacuum. The residue was purified by column chromatography on silica the desired product Ag as a white solid; yield 80%. $^1$H NMR (400 MHz CDCl$_3$): δ; 10.82 (s 1H), 8.88 (d J=2.4 Hz 1H), 7.89 (dd, J=8.8, 2.4 Hz, 1H), 7.20 (d, J=8.8 Hz, 1H), 7.10 (m, 2H), 6.88 (m, 2H) 6.60 (s, 1H) 4.41 (q, J=7.0 Hz, 2H), 4.28 (s 3H), 3.25 (bs 4H), 2.99 (t J=4.8 Hz 4H), 2.92 (t, J=7.6 Hz, 2H), 1.85 (m 2H), 1.67 (t, J=7.0 Hz, 3H). 1.02 (t, J=7.2 Hz 3H). MASS: ESI [M+H]$^+$: 553.00. Elemental anal. calcd. for C$_2$H$_{32}$N$_6$O$_5$S; C, 58.68; H, 5.84; N, 15.21; O, 14.48; S, 5.80; found C, 58.65; H, 5.82; N, 15.26; O, 14.52; S, 5.76.

Example 8: Compound Ah (5-(5-((4-(4-acetylphenyl)piperazin-1-yl)sulfonyl)-2-ethoxy phenyl)-1-methyl-3-propyl-1H-pyrazolo[4,3-d]pyrimidin-7(6H)-one)

Synthesis of Ah; Step 9:

Dissolve 1-[4-(1-piperazinyl)phenyl]ethanone (1 eq) dry acetonitrile and added K$_2$CO$_3$ (3 eq) stirred the reaction mixture for 10 minutes at 20° C., added 4-ethoxy-3-(1-methyl-7-oxo-3-propyl-6,7-dihydro-1H-pyrazolo[4,3-d]pyrimidin-5-yl)benzene-1-sulfonyl chloride (1 eq) and stirred the reaction for 5 hours at 35° C. After completion of the reaction, remove the acetonitrile under vacuum added 30 ml DCM, 30 ml water organic layer was separated. Water layer was re-extracted with 20 ml DCM and the combined organic layer are washed with brine solution, concentrated under vacuum. The residue was purified by column chromatography on silica the desired product Ah as a white solid; yield 90%. $^1$H NMR (400 MHz CDCl$_3$): δ; 10.80 (s 1H), 8.87 (d J=2.4 Hz 1H), 7.88-7.81 (m 3H), 7.17 (d J=8.8 Hz 1H), 6.81 (d J=8.8 Hz 2H) 4.38 (q, J=7.0 Hz, 2H), 4.27 (s, 3H), 3.46 (bs s, 4H), 3.23 (br s 4H), 2.94 (t, J=7.6 Hz, 2H), 2.50 (s, 3H), 1.87 (m, 2H), 1.64 (t, J=7.0 Hz, 3H). 1.03 (t, J=7.2 Hz, 3H). MASS: ESI [M+H]$^+$: 579.00. Elemental anal. calcd. for C$_{29}$H$_{34}$N$_6$O$_5$S; C, 60.19; H, 5.92; N, 14.52; O, 13.82; S, 5.54; found C, 60.15; H, 5.90; N, 14.54; O, 13.80; S, 5.56.

Example 9: Compound Ai (5-(2-ethoxy-5-((4-(pyridin-4-yl)piperazin-1-yl)sulfonyl)phenyl)-1-methyl-3-propyl-1H-pyrazolo[4,3-d]pyrimidin-7(6H)-one)

Synthesis of Ai; Step 9:

Dissolve 1-(4-pyridinyl)piperazine (1 eq) dry CHCl$_3$ and added TEA (3 eq) stirred the reaction mixture for 10 minutes at 10° C., added 4-ethoxy-3-(1-methyl-7-oxo-3-propyl-6,7-dihydro-1H-pyrazolo[4,3-d]pyrimidin-5-yl)benzene-1-sulfonyl chloride (1 eq) and stirred the reaction for 6 hours at 25° C. After completion of the reaction, added 30 ml CHCl$_3$, 30 ml water organic layer was separated. Water layer was re-extracted with 20 ml CHCl$_3$ and the combined organic layer are washed with brine solution, concentrated under vacuum. The residue was purified by column chromatography on silica the desired product Ai as a white solid; yield 93%.

$^1$H NMR (400 MHz, CDCl$_3$) δ 10.82 (s, 1H), 8.84 (s, 1H), 8.26 (d, J=4.8 Hz, 2H), 7.85 (d, J=8.8 Hz, 1H), 7.17 (d, J=8.8 Hz, 1H), 6.60 (d, J=5.0 Hz, 2H), 4.38 (q, J=6.9 Hz, 2H), 4.27 (s, 3H), 3.45 (t, J=4.8 Hz 4H), 3.20 (t, J=4.8 Hz 4H), 2.94 (t, J=7.5 Hz, 2H), 1.88 (m, 2H), 1.64 (t, J=6.9 Hz, 3H), 1.04 (t, J=7.3 Hz, 3H). MASS: ESI [M+H]$^+$: 538.10; Elemental anal. calcd. for C$_{26}$H$_{31}$N$_7$O$_4$S; C, 58.08; H, 5.81; N, 18.24; O, 11.90; S, 5.96; found C, 58.14; H, 5.78; N, 18.21; O, 11.88; S, 5.98.

Example 10: Compound Aj (5-(2-ethoxy-5-((4-(pyridin-2-yl)piperazin-1-yl)sulfonyl) phenyl)-1-methyl-3-propyl-1H-pyrazolo[4,3-d]pyrimidin-7(6H)-one)

Synthesis of Aj; Step 9:

Dissolve 1-(2-pyridinyl)piperazine (1 eq) dry DMF and added CsCO$_3$ (3 eq), stirred the reaction mixture for 10 minutes at 15° C., added 4-ethoxy-3-(1-methyl-7-oxo-3-propyl-6,7-dihydro-1H-pyrazolo[4,3-d]pyrimidin-5-yl)benzene-1-sulfonyl chloride (1 eq) and stirred the reaction for 4 hours at 35° C. After completion of the reaction, added 30 ml EtOAc, 30 ml water organic layer was separated. Water layer was re-extracted with 20 ml EtOAc and the combined organic layer are washed with brine solution, concentrated under vacuum. The residue was purified by column chromatography on silica the desired product Aj as a white solid; yield 91%. $^1$H NMR (400 MHz, CDCl$_3$) δ 10.80 (s, 1H), 8.85 (d, J=2.3 Hz, 1H), 8.14 (d, J=3.6 Hz, 1H), 7.86 (dd, J=8.7, 2.3 Hz, 1H), 7.46 (m, 1H), 7.15 (d, J=8.7 Hz, 1H), 6.64-6.58 (m, 2H), 4.37 (q, J=7.0 Hz, 2H), 4.27 (s, 3H), 3.67 (t, J=4.8 Hz 4H), 3.18 (t, J=4.8 Hz 4H), 2.94 (t, J=7.5 Hz, 2H), 1.87 (m, 2H), 1.64 (t, J=7.0 Hz 3H), 1.04 (t, J=7.4 Hz, 3H). MASS: ESI [M+H]$^+$: 538.10; Elemental anal. calcd. for C$_{26}$H$_{31}$N$_7$O$_4$S; C, 58.08; H, 5.81; N, 18.24; O, 11.90; S, 5.96; found C, 58.12; H, 5.80; N, 18.23; O, 11.86; S, 5.98.

Example 11: Compound Ak (5-(2-ethoxy-5-((4-(pyrimidin-2-yl)piperazin-1-yl)sulfonyl) phenyl)-1-methyl-3-propyl-1H-pyrazolo[4,3-d]pyrimidin-7(6H)-one)

Synthesis of Ak, Step 9:
Dissolve 2-(1-piperazinyl)pyrimidine (1 eq) dry 1,4 dioxane and added TMA (3 eq) stirred the reaction mixture for 10 minutes at 15° C., added 4-ethoxy-3-(1-methyl-7-oxo-3-propyl-6, 7-dihydro-1H-pyrazolo[4,3-d]pyrimidin-5-yl)benzene-1-sulfonyl chloride (1 eq) and stirred the reaction for 6 hours at 27° C. After completion of the reaction, added 30 ml CHCl$_3$, 30 ml water organic layer was separated. Water layer was re-extracted with 20 ml CHCl$_3$ and the combined organic layer are washed with brine solution, concentrated under vacuum. The residue was purified by column chromatography on silica the desired product Ak as a white solid; yield 92%.

$^1$H NMR (400 MHz, CDCl$_3$) δ 10.81 (s, 1H), 8.86 (d, J=2.3 Hz, 1H), 8.28 (d, J=4.7 Hz, 2H), 7.87 (dd, J=8.7, 2.3 Hz, 1H), 7.17 (d, J=8.7 Hz, 1H), 6.51 (t, J=4.7 Hz, 1H), 4.38 (q, J=7.0 Hz, 2H), 4.29 (s, 3H), 3.98 (t, J=4.8 Hz 4H), 3.15 (t, J=4.8 Hz 4H), 2.95 (t, J=7.5 Hz, 2H), 1.95-1.82 (m, 2H), 1.65 (t, J=7.0 Hz, 3H), 1.06 (t, J=7.4 Hz, 3H). MASS: ESI [M+H]$^+$: 539.00. Elemental anal. calcd. for C$_{25}$H$_{30}$N$_8$O$_4$S; C, 55.75; H, 5.61; N, 20.80; O, 11.88; S, 5.95; found C, 55.72; H, 5.64; N, 20.82; O, 11.81; S, 5.92.

Example 12: Compound Al (5-(5-([1,4'-bipiperidin]-1'-ylsulfonyl)-2-ethoxyphenyl)-1-methyl-3-propyl-1H-pyrazolo[4,3-d]pyrimidin-7(6H)-one)

Synthesis of Al; Step 9:
Dissolve 1,4-bipiperidine (1 eq) dry acetone and added K$_2$CO$_3$ (3 eq) stirred the reaction mixture for 10 minutes at 25° C., added 4-ethoxy-3-(1-methyl-7-oxo-3-propyl-6, 7-dihydro-1H-pyrazolo[4,3-d]pyrimidin-5-yl)benzene-1-sulfonyl chloride (1 eq) and stirred the reaction for 4.5 hours at 25° C. After completion of the reaction, remove the acetone under vacuum add 30 ml DCM, 30 ml water organic layer was separated. Water layer was re-extracted with 20 ml DCM and the combined organic layer are washed with brine solution, concentrated under vacuum. The residue was purified by column chromatography on silica the desired product Al as a white solid; yield 90%. $^1$H NMR (400 MHz, CDCl$_3$) δ 10.83 (s, 1H), 8.84 (d, J=2.2 Hz, 1H), 7.87 (dd, J=8.8, 2.2 Hz, 1H), 7.17 (d, J=8.8 Hz, 1H), 4.40 (q, J=7.0 Hz, 2H), 4.30 (s, 3H), 3.94 (d, J=11.5 Hz, 2H), 2.95 (t, J=7.5 Hz, 2H), 2.50 (br s, 4H), 2.35 (s, 2H), 1.88 (m Hz, 4H), 1.75-1.27 (m, 12H), 1.05 (t, J=7.3 Hz, 3H). MASS: ESI [M+H]$^+$: 543.15.

Elemental anal. calcd. for C$_{27}$H$_{38}$N$_6$O$_4$S; C, 59.76; H, 7.06; N, 15.49; O, 11.79; S, 5.91; found C, 59.74; H, 7.08; N, 15.59; O, 11.68; S, 5.90.

Example 13: Compound Am (5-(5-((4-benzylpiperidin-1-yl)sulfonyl)-2-ethoxyphenyl)-1-methyl-3-propyl-1H-pyrazolo[4,3-d]pyrimidin-7(6H)-one)

Synthesis of Am; Step 9:
Dissolve 4-benzylpiperidine (1 eq) dry DCM and added TEA (3 eq) stirred the reaction mixture for 10 minutes at 20° C. 4-ethoxy-3-(1-methyl-7-oxo-3-propyl-6,7-dihydro-1H-pyrazolo[4,3-d]pyrimidin-5-yl)benzene-1-sulfonyl chloride (1 eq) and stirred the reaction for 6 hours at 30° C. After completion of the reaction, added 30 ml DCM, 30 ml water organic layer was separated. Water layer was re-extracted with 20 ml DCM and the combined organic layer are washed with brine solution, concentrated under vacuum. The residue was purified by column chromatography on silica the desired product Am as a white solid; yield 91%. $^1$H NMR (400 MHz, CDCl$_3$) δ 10.84 (s, 1H), 8.82 (d, J=2.3 Hz, 1H), 7.84 (dd, J=8.7, 2.3 Hz, 1H), 7.26 (m, 2H) 7.17 (m, 2H), 7.09 (d, J=7.1 Hz, 2H), 4.39 (q, J=6.9 Hz, 2H), 4.29 (s, 3H), 3.85 (d, J=11.6 Hz, 2H), 2.93 (t, J=7.5 Hz, 2H), 2.54 (d, J=6.6 Hz, 2H), 2.29 (t, J=11.5 Hz, 2H), 1.86 (m, 2H), 1.76-1.61 (m, 4H), 1.41 (m, 2H), 1.02 (t, J=7.4 Hz, 3H). MASS: ESI [M+H]$^+$: 550.05. Elemental anal. calcd. for C$_{29}$H$_{35}$N$_5$O$_4$S; C, 63.37; H, 6.42; N, 12.74; O, 11.64; S, 5.83; found C, 63.42; H, 6.40; N, 12.78; O, 11.62; S, 5.78.

Example 14: Compound An (5-(2-ethoxy-5-((4-methylpiperidin-1-yl)sulfonyl)phenyl)-1-methyl-3-propyl-1H-pyrazolo[4,3-d]pyrimidin-7(6H)-one)

Synthesis of An; Step 9:
Dissolve 4-methylpiperidine (1 eq) dry DCE and added DIPEA (3 eq) stirred the reaction mixture for 10 minutes at 20° C., added 4-ethoxy-3-(1-methyl-7-oxo-3-propyl-6, 7-dihydro-1H-pyrazolo[4,3-d]pyrimidin-5-yl)benzene-1-sulfonyl chloride (1 eq) and stirred the reaction for 6 hours at 30° C. After completion of the reaction, added 30 ml DCM, 30 ml water organic layer was separated. Water layer was re-extracted with 20 ml DCM and the combined organic layer are washed with brine solution, concentrated under vacuum. The residue was purified by column chromatography on silica the desired product An as a white solid; yield 90%.

$^1$H NMR (400 MHz, CDCl$_3$) δ 10.83 (s, 1H), 8.82 (d, J=2.4 Hz, 1H), 7.85 (dd, J=8.8, 2.4 Hz, 1H), 7.15 (d, J=8.8 Hz, 1H), 4.38 (q, J=7.0 Hz, 2H), 4.28 (s, 3H), 3.80 (d, J=11.2 Hz, 2H), 2.93 (t, J=7.6 Hz, 2H), 2.34 (t, J=10.5 Hz, 2H), 1.86 (m, 2H), 1.65 (m 5H), 1.32 (m, 2H), 1.03 (t, J=7.4 Hz, 3H), 0.92 (d, J=5.0 Hz, 3H). MASS: ESI [M+H]$^+$: 474.10; Elemental anal. calcd. for C$_{23}$H$_{31}$N$_5$O$_4$S; C, 57.16; H, 6.21; N, 15.74; O, 14.57; S, 6.31; found C, 57.14; H, 6.17; N, 15.76; O, 14.59; S, 6.33.

Example 15: Compound Ao (tert-butyl (1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)carbamate)

Synthesis of Ao; Step 9:
Dissolve 4-(N-Boc-amino)piperidine (1 eq) dry DCM and added DIPEA (3 eq) stirred the reaction mixture for 10 minutes at 15° C., added 4-ethoxy-3-(1-methyl-7-oxo-3-propyl-6, 7-dihydro-1H-pyrazolo[4,3-d]pyrimidin-5-yl)benzene-1-sulfonyl chloride (1 eq) and stirred the reaction for 6 hours at 30° C. After completion of the reaction, added 30 ml DCM, 30 ml water organic layer was separated. Water layer was re-extracted with 20 ml DCM and the combined organic layer are washed with brine solution, concentrated under vacuum. The residue was purified by column chromatography on silica the desired product Ao as a white solid; yield 90%.

$^1$H NMR (400 MHz, CDCl$_3$) δ 10.85 (s, 1H), 8.82 (d, J=1.9 Hz, 1H), 7.84 (dd, J=8.7, 1.8 Hz, 1H), 7.16 (d, J=8.8 Hz, 1H), 4.39 (q J=6.9 Hz, 2H), 4.28 (s, 3H), 3.74 (br s, 2H), 3.42 (m, 1H), 2.94 (t, J=7.5 Hz, 2H), 2.52 (br s, 2H), 2.00 (d, J=11.2 Hz, 2H), 1.85 (m, 2H), 1.66 (t, J=6.9 Hz, 3H), 1.53 (m, 2H), 1.41 (s, 9H), 1.03 (t, J=7.3 Hz, 3H). MASS: ESI [M+H]$^+$: 575.26 Elemental anal. calcd. for C$_{27}$H$_{38}$N$_6$O$_6$S; C, 56.43; H, 6.66; N, 14.62; O, 16.70; S, 5.58; found C, 56.45; H, 6.56; N, 14.67; O, 16.75; S, 5.56.

Example 16: Compound Ap (5-(5-((4-aminopiperidin-1-yl)sulfonyl)-2-ethoxyphenyl)-1-methyl-3-propyl-1H-pyrazolo[4,3-d]pyrimidin-7(6H)-one)

Synthesis of Ap; Step 9:
Dissolve tert-butyl (1-((4-ethoxy-3-(1-methyl-7-oxo-3-propyl-6, 7-dihydro-1H-pyrazolo[4,3-d]pyrimidin-5-yl)phenyl)sulfonyl)piperidin-4-yl)carbamate (1 eq) dry DCM and added 20% TFA in DCM stirred the reaction mixture at 30° C. for 6 hours. After completion of the reaction, added 30 ml DCM, 30 ml saturated NaHCO$_3$ solution organic layer was separated. Water layer was re-extracted with 20 ml DCM and the combined organic layer are washed with brine solution, concentrated under vacuum. The desired product Ap as a white solid; yield 93%. $^1$H NMR (400 MHz, CDCl$_3$) δ 10.85 (s, 1H), 8.82 (d, J=1.9 Hz, 1H), 7.84 (dd, J=8.7, 1.8 Hz, 1H), 7.16 (d, J=8.8 Hz, 1H), 4.39 (q J=6.9 Hz, 2H), 4.28 (s, 3H), 3.74 (bs, 2H), 3.42 (m, 1H), 2.94 (t, J=7.5 Hz, 2H), 2.52 (bs, 2H), 2.00 (d, J=11.2 Hz, 2H), 1.85 (m, 2H), 1.66 (t, J=6.9 Hz, 3H), 1.53 (m, 2H), 1.03 (t, J=7.3 Hz, 3H), ESI [M+H]$^+$: 475.20; Elemental anal. calcd. For C$_{22}$H$_{30}$N$_6$O$_4$S; C, 55.68; H, 6.37; N, 17.71; O, 13.49; S, 6.76. found C, 55.71; H, 6.40; N, 17.65; O, 13.52; S, 6.73.

Example 17: Compound Ba (5-(3-bromo-4-methoxyphenyl)-1-methyl-3-propyl-1H-pyrazolo[4, 3-d]pyrimidin-7(6H)-one)

Synthesis of Ba; Step 7:
4-amino-1-methyl-3-propyl-1H-pyrazole-5-carboxamide (1 eq) and 3-Bromo-4-methoxybenzaldehyde (1.1 eq) were suspended in ethanol 5 ml and the mixture heated at 70° C. for 2 hours after conformation of forming of imine by TLC. Added CuCl2 (3 eq) and the reaction mixture heated at 75° C. under O$_2$ for 3 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Ba as a white solid; yield 85%. $^1$H NMR (400 MHz DMSO): δ; 8.31 (d J=2.0 Hz 1H), 8.29 (s 1H), 8.14 (dd J=8.8, 2.0 Hz 1H), 7.24 (d J=8.8 Hz) 4.14 (s 3H), 3.93 (s 3H) 2.8 (t J=7.3 Hz 2H), 1.76 (m 2H), 0.95 (t J=7.3 Hz 3H). MASS: ESI [M+2+H]$^+$377.05; Elemental anal. calcd. for C$_{16}$H$_{17}$BrN$_4$O$_2$; C, 50.94; H, 4.54; Br, 21.18; N, 14.85; O, 8.48; found C, 50.89; H, 4.56; Br, 21.21; N, 14.83; O, 8.50.

Example 18: Compound Bb (1-methyl-5-(3-nitrophenyl)-3-propyl-1H-pyrazolo[4,3-d]pyrimidin-7(6H)-one)

Synthesis of Bb; Step 7:
4-amino-1-methyl-3-propyl-1H-pyrazole-5-carboxamide (1 eq) and 3-Nitrobenzaldehyde (1.1 eq) were suspended in methanol 5 ml and the mixture heated at 65° C. for 1.5 hours after conformation of forming of imine by TLC. Added CuCl2 (3 eq) and the reaction mixture heated at 70° C. under O$_2$ for 2.5 hours. After completion of the reaction, the methanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bb as a brown solid; yield 85%. $^1$H NMR (400 MHz DMSO): δ; 8.90 (s 1H), 8.49 (m 1H), 8.35 (m 1H), 7.84-7.80 (m 2H) 4.24 (s 3H), 2.8 (t J=7.3 Hz 2H), 1.80 (m 2H), 0.95 (t J=7.3 Hz 3H). MASS: ESI [M+H]$^+$: 314.12; Elemental anal. calcd. for C$_{15}$H$_{15}$N$_5$O$_3$; C, 57.50; H, 4.83; N, 22.35; O, 15.32; found C, 57.40; H, 4.85; N, 22.38; O, 15.37.

Example 19: Compound Bc (5-(3-bromo-4-fluorophenyl)-1-methyl-3-propyl-1H-pyrazolo [4,3-d]pyrimidin-7(6H)-one)

Synthesis of Bc; Step 7:
4-amino-1-methyl-3-propyl-1H-pyrazole-5-carboxamide (1 eq) and 3-bromo-4-fluorobenzaldehyde (1.1 eq) were suspended in isopropanol 5 ml and the mixture heated at 75° C. for 2 hours after conformation of forming of imine by TLC. Added CuCl2 (3 eq) and the reaction mixture heated at 75° C. under O$_2$ for 3 hours. After completion of the reaction, the isopropanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bc as a white solid; yield 87%. $^1$H NMR (400 MHz DMSO): δ; 12.51 (s 1H), 8.40 (d J=5.2 Hz 1H), 8.13 (S 1H), 7.56 (m 1H) 4.15 (s 3H), 2.8 (t J=7.3 Hz 2H), 1.76 (m 2H), 0.95 (t J=7.3 Hz 3H). MASS: ESI [M+H]$^+$: 365.04; Elemental anal. calcd. for C$_{15}$H$_{14}$BrFN$_4$O; C, 49.33; H, 3.86; Br, 21.88; F, 5.20; N, 15.34; O, 4.38; found C, 49.30; H, 3.87; Br, 21.85; F, 5.22; N, 15.34; O, 4.41.

Example 20: Compound Bd (1-methyl-5-(5-nitrofuran-2-yl)-3-propyl-1H-pyrazolo[4,3-d]pyrimidin-7(6H)-one)

Synthesis of Bd; Step 7:
4-amino-1-methyl-3-propyl-1H-pyrazole-5-carboxamide (1 eq) and 5-Nitro-2-furaldehyde (1.1 eq) were suspended in ethanol 5 ml and the mixture heated at 60° C. for 0.5 hours after conformation of forming of imine by TLC. Added CuCl2 (3 eq) and the reaction mixture heated at 65° C. under O$_2$ for 0.5 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bd as a yellow solid; yield 93%. $^1$H NMR (200 MHz CDCl$_3$): δ; 12.87 (br 1H) 7.85 (br 1H), 7.74 (br 1H), 4.16 (s 3H), 2.8 (br 2H), 1.76 (m 2H), 0.95 (t J=7.3 Hz 3H). MASS: ESI [M+H]$^+$: 304.10; Elemental anal. calcd. for $C_{13}H_{13}N_5O_4$; C, 51.48; H, 4.32; N, 23.09; O, 21.10; found C, 51.39; H, 4.34; N, 23.12; O, 21.14.

Example 21: Compound Be (5-(4-hydroxyphenyl)-1-methyl-3-propyl-1H-pyrazolo[4,3-d]pyrimidin-7(6H)-one)

Synthesis of Be; Step 7:
4-amino-1-methyl-3-propyl-1H-pyrazole-5-carboxamide (1 eq) and 4-hydroxybenzaldehyde (1.1 eq) were suspended in ethanol 5 ml and the mixture heated at 60° C. for 1.5 hours after conformation of forming of imine by TLC. Added CuCl2 (3 eq) and the reaction mixture heated at 70° C. under $O_2$ for 2 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Be as a white solid; yield 90%. $^1$H NMR (400 MHz DMSO) δ; 8.29 (s 1H), 7.93 (d J=8.8 Hz 2H), 6.86 (d J=8.8 Hz 2H) 4.13 (s 3H), 2.78 (t J=7.4 Hz 2H), 1.76 (m 2H), 0.95 (t J=7.4 Hz 3H). MASS: ESI [M+H]$^+$: 285.13. Elemental anal. calcd. for $C_{15}H_{16}N_4O_2$; C, 63.37; H, 5.67; N, 19.71; O, 11.25; found C, 63.32; H, 5.68; N, 19.73; O, 11.27.

Example 22: Compound Bf (5-(4-methoxy-3-nitrophenyl)-1-methyl-3-propyl-1H-pyrazolo [4,3-d]pyrimidin-7(6H)-one)

Synthesis of Bf; Step 7:
4-amino-1-methyl-3-propyl-1H-pyrazole-5-carboxamide (1 eq) and 4-methoxy-3-nitrobenzaldehyde (1.1 eq) were suspended in ethanol 5 ml and the mixture heated at 75° C. for 2 hours after conformation of forming of imine by TLC. Added CuCl$_2$ (3 eq) and the reaction mixture heated at 75° C. under $O_2$ for 2 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bf as a brown solid; yield 88%. $^1$H NMR (400 MHz, DMSO) δ: 12.54 (s 1H) 8.61 (s, 1H), 8.37 (d J=8.8 Hz 1H), 7.39 (d, J=8.8 Hz 1H), 4.13 (s, 3H), 3.84 (s, 3H), 2.78 (t J=7.4 Hz 2H), 1.76 (m 2H), 0.95 (t J=7.4 Hz 3H). MASS: ESI [M+H]$^+$: 344.13; Elemental anal. calcd. for $C_{16}H_{17}N_5O_4$; C, 55.97; H, 4.99; N, 20.40; O, 18.64; found C, 55.87; H, 5.03; N, 20.43; O, 18.67.

Example 23: Compound Bg (5-(4-methoxyphenyl)-1-methyl-3-propyl-1H-pyrazolo[4,3-d]pyrimidin-7(6H)-one)

Synthesis of Bg; Step 7:
4-amino-1-methyl-3-propyl-1H-pyrazole-5-carboxamide (1 eq) and 4-methoxybenzaldehyde (1.1 eq) were suspended in ethanol 5 ml and the mixture heated at 70° C. for 1 hours after conformation of forming of imine by TLC. Added CuCl2 (3 eq) and the reaction mixture heated at 75° C. under $O_2$ for 1 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bg as a white solid; yield 89%. $^1$H NMR (200 MHz CDCl$_3$): δ; 10.37 (br 1H), 8.02 (d J=7.3 Hz 2H), 7.03 (d J=7.3 Hz 2H), 4.28 (s 3H), 3.89 (s 3H), 2.93 (t J=7.4 Hz 2H), 1.87 (m 2H), 1.03 (t J=7.4 Hz 3H). MASS: ESI [M+H]$^+$: 299.15; Elemental anal. calcd. for $C_{16}H_{18}N_4O_2$; C, 64.41; H, 6.08; N, 18.78; O, 10.73; found C, 64.37; H, 6.12; N, 18.71; O, 10.81.

Example 24: Compound Bh (5-(4-chlorophenyl)-1-methyl-3-propyl-1H-pyrazolo[4,3-d]pyrimidin-7(6H)-one)

Synthesis of Bh; Step 7:
4-amino-1-methyl-3-propyl-1H-pyrazole-5-carboxamide (1 eq) and 4-chlorobenzaldehyde (1.1 eq) were suspended in ethanol 5 ml and the mixture heated at 70° C. for 1.5 hours after conformation of forming of imine by TLC. Added CuCl2 (3 eq) and the reaction mixture heated at 75° C. under $O_2$ for 1 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bh as a white solid; yield 90%. $^1$H NMR (200 MHz CDCl$_3$): δ; 11.51 (s 1H), 8.1 (d J=8.6 Hz 2H), 7.49 (d J=8.6 Hz 2H), 4.3 (s 3H), 2.93 (t J=7.5 Hz 2H), 1.96 (m 2H), 1.03 (t J=7.5 Hz 3H). MASS: ESI [M+H]$^+$: 303.09; Elemental anal. calcd. for $C_{15}H_{15}ClN_4O$; C, 59.51; H, 4.99; Cl, 11.71; N, 18.51; O, 5.28; found C, 59.44; H, 5.01; Cl, 11.72; N, 18.53; O, 5.30.

Example 25: Compound Bi (1-methyl-3-propyl-5-(2,4,5-trimethoxyphenyl)-1H-pyrazolo [4,3-d]pyrimidin-7(6H)-one)

Synthesis of Bi; Step 7:
4-amino-1-methyl-3-propyl-1H-pyrazole-5-carboxamide (1 eq) and 2,4,5-trimethoxybenzaldehyde (1 eq) were suspended in ethanol 5 ml and the mixture heated at 60° C. for 0.5 hours after conformation of forming of imine by TLC. Added CuCl2 (3 eq) and the reaction mixture heated at 75° C. under $O_2$ for 0.5 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bi as a white solid; yield 87%. $^1$H NMR (200 MHz CDCl$_3$): δ; 11.0 (s 1H), 8.03 (s 1H), 6.59 (s 1H), 4.42 (s 3H), 4.06 (s 3H), 3.98 (s 6H), 2.93 (t J=7.3 Hz 2H), 1.57 (m 2H), 1.04 (t J=7.3 Hz 3H). MASS: ESI [M+H]$^+$: 359.17; Elemental anal. calcd. for $C_{18}H_{22}N_4O_4$; C, 60.32; H, 6.19; N, 15.63; O, 17.86; found C, 60.29; H, 6.23; N, 15.67; O, 17.91.

Example 26: Compound Bj (5-(3-fluoro-4-methoxyphenyl)-1-methyl-3-propyl-1H-pyrazolo [4,3-d]pyrimidin-7(6H)-one)

Synthesis of Bj; Step 7:
4-amino-1-methyl-3-propyl-1H-pyrazole-5-carboxamide (1 eq) and 3-fluoro-4-methoxybenzaldehyde (1.1 eq) were suspended in ethanol 5 ml and the mixture heated at 75° C. for 2 hours after conformation of forming of imine by TLC. Added CuCl2 (3 eq) and the reaction mixture heated at 75° C. under $O_2$ for 1.5 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bj as a white solid; yield 87%. $^1$H NMR (500 MHz CDCl$_3$): δ; 11.04 (s 1H), 8.04 (dd J=8.7, 2.2 Hz 1H), 7.88 (d J=8.8 Hz 1H), 7.07 (d J=2.2 Hz 1H), 4.44 (s 3H), 4.12 (s 3H), 2.93 (t J=7.7 Hz 2H), 1.90 (m 2H), 1.05 (tJ=7.5 Hz 3H). MASS: ESI [M+H]$^+$: 317.14. Elemental anal. calcd. for $C_{16}H_{17}FN_4O_2$; C, 60.75; H, 5.42; F, 6.01; N, 17.71; O, 10.12; found C, 60.81; H, 5.59; F, 6.03; N, 17.68; O, 10.15.

Example 27: Compound Bk (5-(3,5-dimethoxyphenyl)-1-methyl-3-propyl-1H-pyrazolo[4,3-d]pyrimidin-7(6H)-one)

Synthesis of Bk; Step 7:
4-amino-1-methyl-3-propyl-1H-pyrazole-5-carboxamide (1 eq) and 3,5-dimethoxybenzaldehyde (1.1 eq) were suspended in ethanol 5 ml and the mixture heated at 60° C. for 1 hours after conformation of forming of imine by TLC. Added CuCl2 (3 eq) and the reaction mixture heated at 70° C. under $O_2$ for 0.5 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bk as a white solid; yield 90%. $^1$H NMR (200 MHz CDCl$_3$): δ; 7.25 (d J=2.0 Hz 2H), 6.6 (d J=2.0 Hz 1H), 4.29 (s 3H), 3.88 (s 6H), 2.93 (t J=7.4 Hz 2H), 1.87 (m 2H), 1.04 (tJ=7.3 Hz 3H). MASS: ESI [M+H]$^+$: 329.16; Elemental anal. calcd. for $C_{17}H_{20}N_4O_3$; C, 62.18; H, 6.14; N, 17.06; O, 14.62; found C, 62.21; H, 6.11; N, 17.12; O, 14.56.

Example 28: Compound Bl (5-(3-chlorophenyl)-1-methyl-3-propyl-1H-pyrazolo[4,3-d]pyrimidin-7(6H)-one)

Synthesis of Bl; Step 7:
4-amino-1-methyl-3-propyl-1H-pyrazole-5-carboxamide (1 eq) and 3-chlorobenzaldehyde (1.1 eq) were suspended in ethanol 5 ml and the mixture heated at 75° C. for 1.5 hours after conformation of forming of imine by TLC. Added CuCl2 (3 eq) and the reaction mixture heated at 75° C. under $O_2$ for 1.5 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bl as a white solid; yield 90%. $^1$H NMR (200 MHz CDCl$_3$) δ 12.06 (s 1H), 8.22 (s 1H), 8.08 (d J=7.6 Hz 1H) 7.45 (m, 2H) 4.05 (s, 3H), 2.94 (t, J=7.4 Hz, 2H), 1.86 (m, 2H), 1.04 (t, J=7.4 Hz, 3H). MASS: ESI [M+H]$^+$: 303.09; Elemental anal. calcd. for $C_{15}H_{15}ClN_4O$; C, 59.51; H, 4.99; Cl, 11.71; N, 18.51; O, 5.28; found C, 59.48; H, 4.51; Cl, 11.69; N, 18.49; O, 5.33.

Example 29: Compound Bm (5-(2-fluorophenyl)-1-methyl-3-propyl-1H-pyrazolo[4,3-d]pyrimidin-7(6H)-one)

Synthesis of Bm; Step 7:
4-amino-1-methyl-3-propyl-1H-pyrazole-5-carboxamide (1 eq) and 2-chlorobenzaldehyde (1.1 eq) were suspended in ethanol 5 ml and the mixture heated at 65° C. for 2 hours after conformation of forming of imine by TLC. Added CuCl2 (3 eq) and the reaction mixture heated at 70° C. under $O_2$ for 2 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bm as a white solid; yield 88%. $^1$H NMR (200 MHz CDCl$_3$) δ 12.06 (s 1H), 8.01 (M, 1H), 7.45 (m, 1H), 7.32 (td, J=7.8, 1.5 Hz, 1H), 7.21 (td, J=7.5, 1.4 Hz, 1H), 4.05 (s, 3H), 3.03 (t, J=7.4 Hz, 2H), 1.86 (m, 2H), 1.06 (t, J=7.4 Hz, 3H). MASS: ESI [M+H]$^+$: 287.12; Elemental anal. calcd. for $C_{15}H_{15}FN_4O$; C, 62.93; H, 5.28; F, 6.64; N, 19.57; O, 5.59; found C, 62.88; H, 5.31; F, 6.64; N, 19.57; O, 5.61.

Example 30: Compound Bn (5-(3-fluorophenyl)-1-methyl-3-propyl-1H-pyrazolo[4,3-d]pyrimidin-7(6H)-one)

Synthesis of Bn; Step 7:
4-amino-1-methyl-3-propyl-1H-pyrazole-5-carboxamide (1 eq) and 3-fluorobenzaldehyde (1.1 eq) were suspended in ethanol 5 ml and the mixture heated at 75° C. for 2 hours after conformation of forming of imine by TLC. Added CuCl2 (3 eq) and the reaction mixture heated at 75° C. under $O_2$ for 2 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bn as a white solid; yield 90%. $^1$H NMR (200 MHz CDCl$_3$) δ 12.06 (s 1H), 7.91 (m 1H), 7.48 (m 1H), 7.40 (m 1H), 7.31 (m 1H), 4.05 (s, 3H), 3.03 (t, J=7.4 Hz, 2H), 1.86 (m, 2H), 1.06 (t, J=7.4 Hz, 3H). MASS: ESI [M+H]$^+$: 329.16; Elemental anal. calcd. for $C_{15}H_{15}FN_4O$; C, 62.93; H, 5.28; F, 6.64; N, 19.57; O, 5.59; found C, 62.95; H, 5.31; F, 6.59; N, 19.52; O, 5.64.

Example 31: Compound Bo (5-(4-hydroxy-3-nitrophenyl)-1-methyl-3-propyl-1H-pyrazolo [4,3-d]pyrimidin-7(6H)-one)

Synthesis of Bo; Step 7:
4-amino-1-methyl-3-propyl-1H-pyrazole-5-carboxamide (1 eq) and 4-hydroxy-3-nitrobenzaldehyde (1.1 eq) were suspended in ethanol 5 ml and the mixture heated at 70° C. for 1.5 hours after conformation of forming of imine by TLC. Added CuCl2 (3 eq) and the reaction mixture heated at 75° C. under $O_2$ for 1 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bo as a yellow solid; yield 90%. $^1$H NMR (400 MHz, DMSO) δ 12.49 (s, 1H), 8.64 (s, 1H), 8.25 (d, J=8.7 Hz, 1H), 7.24 (d, J=8.7 Hz, 1H), 4.14 (s, 3H), 2.79 (t, J=7.5 Hz, 2H), 1.86-1.65 (m, 2H), 0.95 (t, J=7.4 Hz, 3H). MASS: ESI [M+H]$^+$: 330.11; Elemental anal. calcd. for $C_{15}H_{16}N_5O_4$; C, 54.71; H, 4.59; N, 21.27; O, 19.43; found C, 54.68; H, 4.61; N, 21.31; O, 19.40.

Example 32: Compound Bp (5-(3,4-dimethoxyphenyl)-1-methyl-3-propyl-1H-pyrazolo[4,3-d]pyrimidin-7(6H)-one)

Synthesis of Bp; Step 7:
4-amino-1-methyl-3-propyl-1H-pyrazole-5-carboxamide (1 eq) and 3,4-dimethoxybenzaldehyde (1.1 eq) were suspended in ethanol 5 ml and the mixture heated at 70° C. for 1.5 hours after conformation of forming of imine by TLC. Added CuCl2 (3 eq) and the reaction mixture heated at 70° C. under $O_2$ for 1.5 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bp as a white solid; yield 90%. $^1$H NMR (200 MHz CDCl$_3$) δ 10.58 (s 1H), 7.65-7.55 (m 2H) 6.97 (d J=8.4 Hz 1H) 4.27 (s, 3H), 2.92 (t, J=7.3 Hz, 2H), 1.86 (m, 2H), 1.04 (t, J=7.3 Hz, 3H). MASS: ESI [M+H]$^+$: 329.16; Elemental anal. calcd. for $C_{17}H_{21}N_4O_3$; C, 62.18; H, 6.14; N, 17.06; O, 14.62; found C, 62.21; H, 6.10; N, 17.20; O, 14.59.

Example 33: Compound Bq (5-(benzo[d][1,3]dioxol-5-yl)-1-methyl-3-propyl-1H-pyrazolo [4,3-d]pyrimidin-7(6H)-one)

Synthesis of Bq; Step 7:
4-amino-1-methyl-3-propyl-1H-pyrazole-5-carboxamide (1 eq) and Piperonal (1.1 eq) were suspended in ethanol 5 ml and the mixture heated at 75° C. for 2 hours after conformation of forming of imine by TLC. Added CuCl2 (3 eq) and the reaction mixture heated at 75° C. under $O_2$ for 1 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Bq as a white solid; yield 89%. $^1$H NMR (200 MHz CDCl$_3$) δ 10.49 (s 1H), 7.65 (s 1H), 7.57 (d J=8.1 Hz 1H) 6.92 (d J=8.1 Hz 1H) 6.07 (s, 2H) 4.28 (s, 3H), 2.92 (t, J=7.7 Hz, 2H), 1.86 (m, 2H), 1.04 (t, J=7.2 Hz, 3H). MASS: ESI [M+H]$^+$: 313.12; Elemental anal. calcd. for $C_{16}H_{17}N_4O$; C, 61.53; H, 5.16; N, 17.94; O, 15.37; found C, 61.49; H, 5.19; N, 17.91; O, 15.41.

Example 34: Compound Br (1-methyl-3-propyl-5-(pyridin-3-yl)-1H-pyrazolo[4,3-d]pyrimidin-7(6H)-one)

Synthesis of Br; Step 7:
4-amino-1-methyl-3-propyl-1H-pyrazole-5-carboxamide (1 eq) and 3-Pyridinecarboxaldehyde (1.1 eq) were suspended in ethanol 5 ml and the mixture heated at 70° C. for 2 hours after conformation of forming of imine by TLC. Added CuCl2 (3 eq) and the reaction mixture heated at 70° C. under $O_2$ for 1.5 hours. After completion of the reaction, the ethanol was removed under vacuum. Then workup with ethyl acetate and water. Separate the organic layer and Water layer re-extracted with 2×25 ml ethyl acetate. The combined organic layers are washed with brine solution, concentrated under vacuum. The residue was purified by column chromatography on silica the desired product Br as a brown solid; yield 88%. $^1$H NMR (200 MHz CDCl$_3$): δ; 12.06 (s 1H), 9.43 (br 1H) 8.78 (br 1H), 8.52 (d J=7.8 Hz 1H), 7.47 (br 1H), 4.30 (s 3H), 2.94 (t J=7.3 Hz 2H), 1.87 (m 2H), 1.03 (t J=7.3 Hz 3H). MASS: ESI [M+H]$^+$: 270.13 Elemental anal. calcd. for $C_{14}H_{15}N_5O$; C, 62.44; H, 5.61; N, 26.01; O, 5.94; found C, 62.39; H, 5.54; N, 26.11; O, 5.96.

Example 35: PDE5 Enzyme Inhibitory Assay (In Vitro)

The PDE5 inhibitory activity (IC$_{50}$) of the invented compound was checked by using commercially available purified human PDE5A active (Signalchem, Canada: Cat No. P93-31G), expressed by baculovirus in sf9 insect cells and PDE Glo Phosphodiesterase Assay kit from Promega (Cat No. V1361). The assays were performed by following the manufacturer recommended protocol.

The IC$_{50}$ value of reference molecule i.e. sildenafil was (5.6 nM), which was almost similar with literature reported value. The screening for PDE5 inhibitory activity of all the pyrazolopyrimidinone based compounds was determined at 750 nM and 1.5 µM concentrations. The results showed these molecules were highly active against the PDE5A. Some of the compounds have shown better IC$_{50}$ values compared to reference compound.

Example 36: IC$_{50}$ Determination

In order to determine the IC$_{50}$ of the active molecules a nine point titration in duplicate against the PDE5A was performed and found some of the invented compounds were more active than that of reference. Some of the representative molecules showed an IC$_{50}$ viz. compound Aa: 0.8 nM (FIG. 2), compound Ab 4.8 nM. Data analysis was performed with GraphPad Prism®, version 5.00, for Windows using a sigmoidal dose-response (variable slope) equation. Each point represents an average of two replicates per concentration.

Example 37: In Vivo Efficacy of Representative Compound Aa Using 'Conscious Rabbit Model'

Nitric oxide is the main neurotransmitter which mediates smooth muscle relaxation by activating the guanylate cyclise during penile erection, which in turn increases the cGMP level. In penile tissue cGMP is predominantly metabolized by PDE5, hence an inhibitor of PDE5 increases cGMP, enhances relaxation of smooth muscle in the corpus cavernosum, and induces penile erection (Moreland R B, et al Life Sci 1998, 62, 309-318.). In order to check the in vivo activity of the most effective molecule, we followed a well accepted model for penile erection called Conscious Rabbit model (E Bischoff et al Int. J. Impot. Res. 2001, 13, 230-235).

Briefly, compound Aa was dissolved in Transcutol and diluted with 20% Cremophor-EL in distilled water at a ratio of 3:7. This solution was injected into the ear vein of a group of five healthy male rabbit (3-3.5 kg weight) in a volume of 0.5 ml/kg. The event was followed 5 minutes later by another equal volume saline injection containing Sodium nitroprusside (0.2 mg/kg), which acts as a donor of Nitric oxide (NO). Length of uncovered penile mucosa was measured with a sliding caliper at different time points for an hour after administration of the test compounds. The area under the curve (AUC) was calculated by Graph Pad Software. Controls experiments were performed with the SNP alone injections. The results (FIG. 3) show that indeed compound-Aa is working either equally or more efficiently than reference. The AUC value of Compound-Aa (722) is comparably higher than that of reference Sildenafil (330).

Advantages of the Present Invention

1. The present invention provides the novel structural entities as PDE5 inhibitors for the treatment of impotence.
2. The present invention provides new generation pyrazolopymidinone compounds with better PK parameters as PDE5 inhibitors for the treatment of impotence.
3. The in vivo efficacy of invented compounds is better than the existing pyrazolopyrimidine class of compounds.
4. The present invention covers diversity in the claimed structures as per formula 1, representing 2 classes of compounds 1A and 1B.
5. The process mentioned for synthesis of these compounds gives excellent yields.
6. The process offered is scalable.
7. Many of the compounds shows nanomolar potency for PDE5 inhibition.
8. The present invention also provides isoform selectivity of these compounds for different PDE enzymes to find enzyme specificity.

Abbreviations

ACN: acetonitrile
ATP: adenosine triphosphate
AMP: adenosine monophosphate
cAMP: cyclic adenosine monophosphate
$CDCl_3$: dueterated chloroform
cGMP: cyclic guanosine monophosphate
$CHCl_3$: chloroform
$ClSO_3H$: chlorosulphonic acid
$^{13}CNMR$: carbon nuclear magnetic resonance
$CuCl_2$: copper (II) chloride
DCM or $CH_2Cl_2$: dichloromethane
DIPEA: diisopropyl ethyl amine
DMAP: 4-dimethylaminopyridine
DMF: dimethylformamide
DMSO: dimethylsulfoxide
EtOAc: ethylacetate
EtOH: ethanol
FDA: food and drug administration
GMP: guanosine monophosphate
GTP: guanosine triphosphate
h or hr: hour
HCl: hydrochloric acid
$HNO_3$: nitric acid
$H_2SO_4$: sulphuric acid
$^1HNMR$: proton nuclear magnetic resonance
HRMS: high-resolution mass spectrometry
$IC_{50}$: 50% inhibitory concentration
J: coupling constant (Hz)
MeOH: methanol
$(MeO)_2SO_2$: dimethyl sulfate
MHz: Megahertz
mg: milli gram
µg: microgram
µL: micro liter
Mmol: milli mole
m/z: mass-to-charge ratio
NaOH: sodium hydroxide
$NH_4Cl$: ammonium chloride
nM: nanomolar
PDE: phosphodiesterase
PDE5: phosphodiesterase5
PKA: protein kinase A
PTSA: p-toluenesulfonic acid
Py: Pyridine
rf: reflux
rt: room temperature
$SOCl_2$: thionyl chloride
TEA: triethyl amine
THF: tetrahydrofuran
TLC: thin layer chromatography
TMA: trimethyl amine

We claim:
1. A compound or a pharmaceutically acceptable salt thereof having a formula

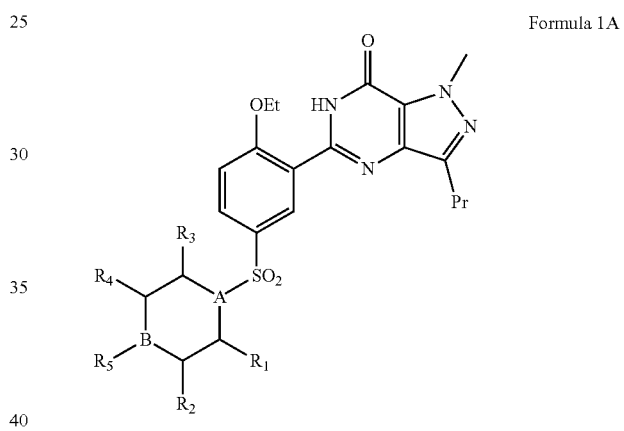

Formula 1A wherein Formula 1A includes a cyclic ring directly bonded to —$SO_2$, wherein the —$SO_2$ is also bonded to an aryl ring at $4^{th}$ position relative to an —OEt substitution on the aryl ring,
wherein the cyclic ring is a six membered ring containing at least one substitution,
wherein A represents —N, —S, —CH, CR,
wherein B represents —S, —CH, CR, —N,
wherein R is BocHN, a substituted aryl, a heteroaryl, an alkyl, a heterocycloalkane with substitution selected from the group consisting of a ketone, an aryl, a methyl, an ethyl, a propyl, a butyl, a pentyl, a hexyl, a heptyl, an octyl, a nonyl, and a decyl optionally having a hydroxyl, an amino, and a halo group at the terminal position of the carbon chain optionally having unsaturation on carbon chain at any position,
wherein $R_1$ to $R_4$ are each independently selected from H, an alkyl, an aryl, a halo, an oxy, a hydroxy, an alkoxy, an alkyl halide, an alkyne ether, an allyl ether, a substituted alkene, an amino, a formyl, and a nitro with substitutions optionally having heteroaryl substitutions,
wherein $R_5$ is selected from an aryl, a halo, an oxy, a hydroxy, an alkoxy, an alkyl halide, an alkyne ether, an allyl ether, a substituted alkene, an amino, a formyl, and a nitro with substitutions optionally having heteroaryl substitutions, wherein, the heteroaryl group is selected from the group consisting of a thiophenyl, a thiobenzyl, a quinolyl, a quinazolinyl, an isoquinolyl, a benzopyranyl, and a tetrazolyl.

2. The compound as claimed in claim 1, wherein the representative compounds of formula 1A are selected from the group consisting of:

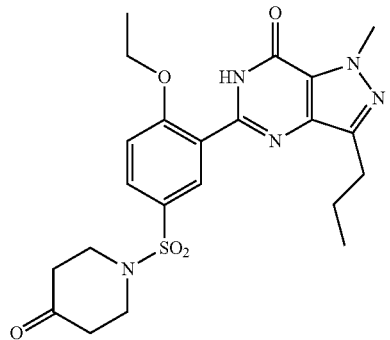 [SMILES: CCCc1nn(C)c2c(=O)[nH]c(-c3cc(S(=O)(=O)N4CCC(=O)CC4)ccc3OCC)nc12]

5-(2-ethoxy-5-((4-oxopiperidin-1-yl)sulfonyl)phenyl)-1-methyl-3-propyl-1H-pyrazolo[4,3-d]pyrimidin-7(6H)-one,

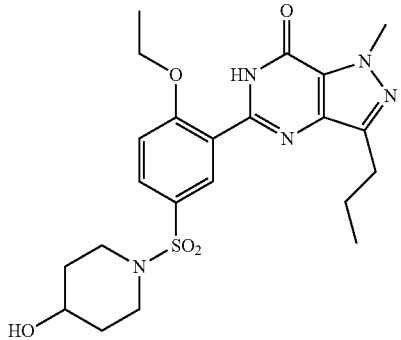 [SMILES: CCCc1nn(C)c2c(=O)[nH]c(-c3cc(S(=O)(=O)N4CCC(O)CC4)ccc3OCC)nc12]

5-(2-ethoxy-5-((4-hydroxypiperidin-1-yl)sulfonyl)phenyl)-1-methyl-3-propyl-1H-pyrazolo[4,3-d]pyrimidin-7(6H)-one,

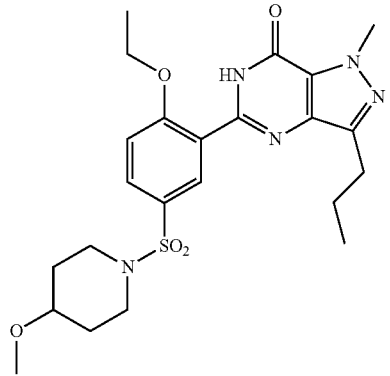 [SMILES: CCCc1nn(C)c2c(=O)[nH]c(-c3cc(S(=O)(=O)N4CCC(OC)CC4)ccc3OCC)nc12]

5-(2-ethoxy-5-((4-methoxypiperidin-1-yl)sulfonyl)phenyl)-1-methyl-3-propyl-1H-pyrazolo[4,3-d]pyrimidin-7(6H)-one,

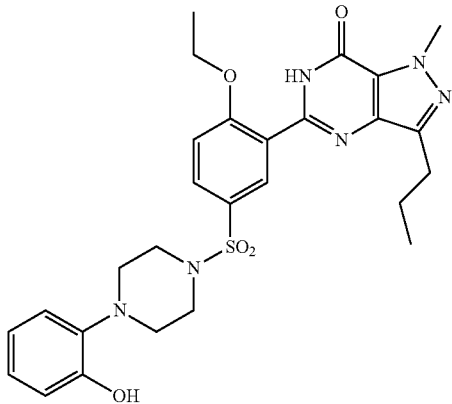 [SMILES: CCCc1nn(C)c2c(=O)[nH]c(-c3cc(S(=O)(=O)N4CCN(c5ccccc5O)CC4)ccc3OCC)nc12]

5-(2-ethoxy-5-((4-(2-hydroxyphenyl)piperazin-1-yl)sulfonyl) phenyl)-1-methyl-3-propyl-1H-pyrazolo[4,3-d]pyrimidin-7(6H)-one),

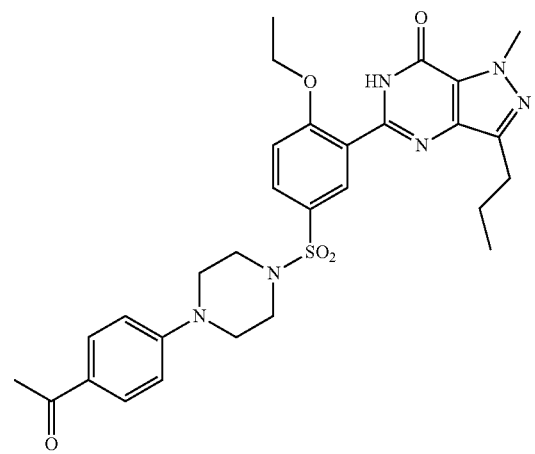 [SMILES: CCCc1nn(C)c2c(=O)[nH]c(-c3cc(S(=O)(=O)N4CCN(c5ccc(C(C)=O)cc5)CC4)ccc3OCC)nc12]

5-(5-((4-(4-acetylphenyl)piperazin-1-yl)sulfonyl)-2-ethoxy phenyl)-1-methyl-3-propyl-1H-pyrazolo[4,3-d]pyrimidin-7(6H)-one,

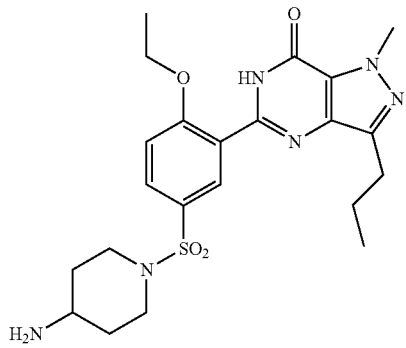 [SMILES: CCCc1nn(C)c2c(=O)[nH]c(-c3cc(S(=O)(=O)N4CCC(N)CC4)ccc3OCC)nc12]

5-(5-((4-aminopiperidin-1-yl)sulfonyl)-2-ethoxyphenyl)-1-methyl-3-propyl-1H-pyrazolo[4,3-d]pyrimidin-7 (6H)-one,

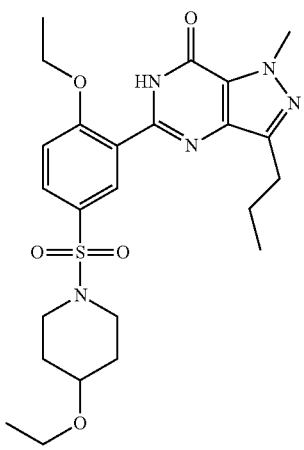 [SMILES: CCCc1nn(C)c2c(=O)[nH]c(-c3cc(S(=O)(=O)N4CCC(OCC)CC4)ccc3OCC)nc12]

5-(2-ethoxy-5-((4-ethoxypiperidin-1-yl)sulfonyl)phenyl)-1-methyl-3-propyl-1H-pyrazolo[4,3-d]pyrimidin-7(6H)-one,

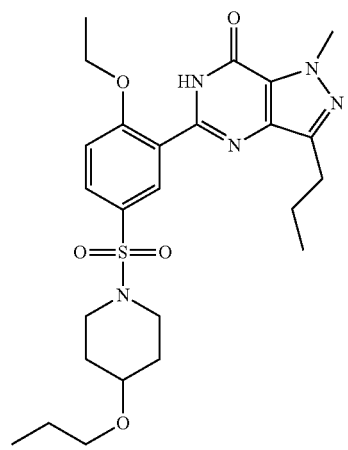

5-(2-ethoxy-5-((4-propoxypiperidin-1-yl)sulfonyl)phenyl)-1-methyl-3-propyl-1H-pyrazolo[4,3-d]pyrimidin-7(6H)-one,

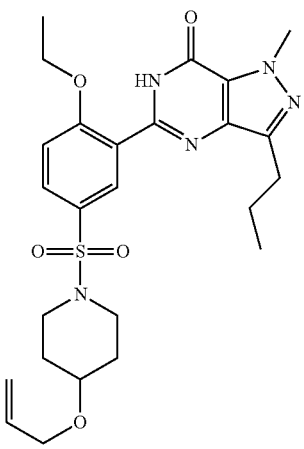 [SMILES: C=CCOC1CCN(S(=O)(=O)c2ccc(OCC)c(-c3nc4c(CCC)nn(C)c4c(=O)[nH]3)c2)CC1]

5-(5-((4-(allyloxy)piperidin-1-yl)sulfonyl)-2-ethoxyphenyl)-1-methyl-3-propyl-1H-pyrazolo[4,3-d]pyrimidin-7(6H)-one,

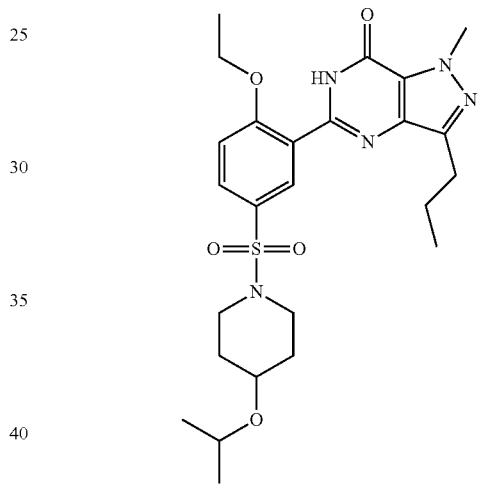

5-(2-ethoxy-5-((4-isopropoxypiperidin-1-yl)sulfonyl)phenyl)-1-methyl-3-propyl-1H-pyrazolo[4,3-d]pyrimidin-7(6H)-one,

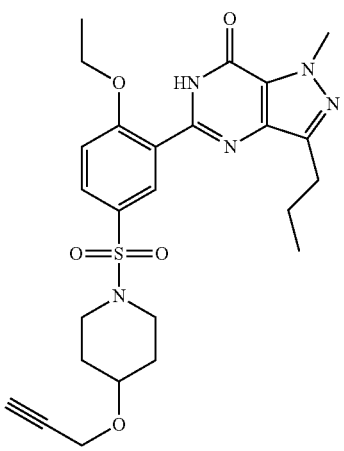 [SMILES: C#CCOC1CCN(S(=O)(=O)c2ccc(OCC)c(-c3nc4c(CCC)nn(C)c4c(=O)[nH]3)c2)CC1]

5-(2-ethoxy-5-((4-(prop-2-yn-1-yloxy)piperidin-1-yl)sulfonyl)phenyl)-1-methyl-3-propyl-1H-pyrazolo[4,3-d]pyrimidin-7(6H)-one,

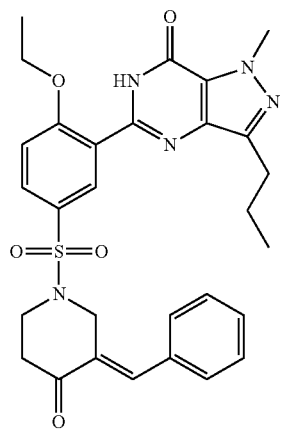 [SMILES: CCCc1nn(C)c2c(=O)[nH]c(-c3cc(S(=O)(=O)N4CCC(=O)/C(=C/c5ccccc5)C4)ccc3OCC)nc12]

(E)-5-(5-((3-benzylidene-4-oxopiperidin-1-yl)sulfonyl)-2-ethoxyphenyl)-1-methyl-3-propyl-1H-pyrazolo[4,3-d]pyrimidin-7(6H)-one,

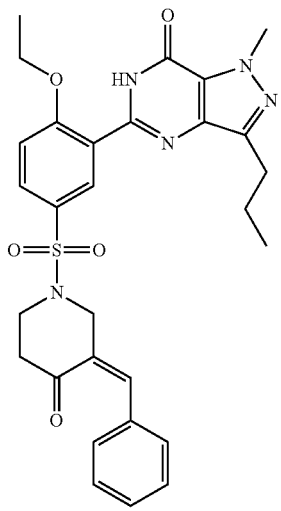 [SMILES: CCCc1nn(C)c2c(=O)[nH]c(-c3cc(S(=O)(=O)N4CCC(=O)/C(=C\c5ccccc5)C4)ccc3OCC)nc12]

(Z)-5-(5-((3-benzylidene-4-oxopiperidin-1-yl)sulfonyl)-2-ethoxyphenyl)-1-methyl-3-propyl-1H-pyrazolo[4,3-d]pyrimidin-7(6H)-one,

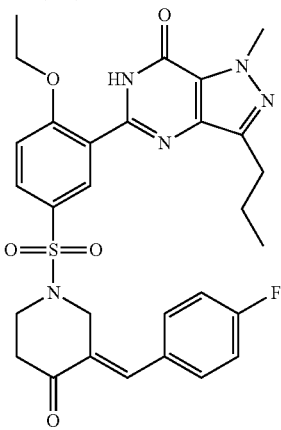 [SMILES: CCCc1nn(C)c2c(=O)[nH]c(-c3cc(S(=O)(=O)N4CCC(=O)/C(=C/c5ccc(F)cc5)C4)ccc3OCC)nc12]

(E)-5-(2-ethoxy-5-((3-(4-fluorobenzylidene)-4-oxopiperidin-1-yl)sulfonyl)phenyl)-1-methyl-3-propyl-1H-pyrazolo[4,3-d]pyrimidin-7(6H)-one,

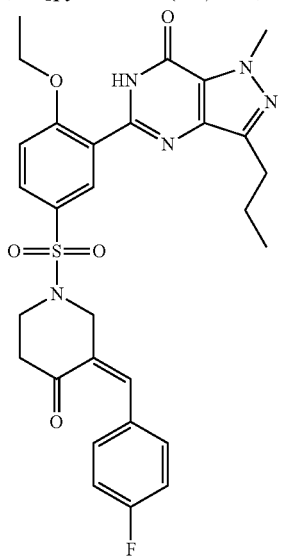

(Z)-5-(2-ethoxy-5-((3-(4-fluorobenzylidene)-4-oxopiperidin-1-yl)sulfonyl)phenyl)-1-methyl-3-propyl-1H-pyrazolo[4,3-d]pyrimidin-7(6H)-one,

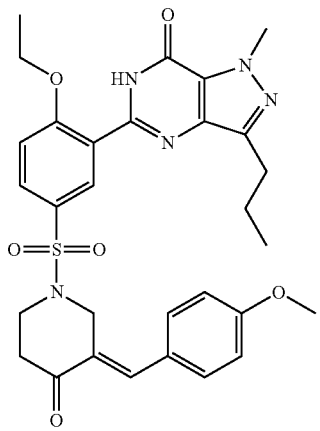 [SMILES: CCCc1nn(C)c2c(=O)[nH]c(-c3cc(S(=O)(=O)N4CCC(=O)/C(=C/c5ccc(OC)cc5)C4)ccc3OCC)nc12]

(E)-5-(2-ethoxy-5-((3-(4-methoxybenzylidene)-4-oxopiperidin-1-yl)sulfonyl)phenyl)-1-methyl-3-propyl-1H-pyrazolo[4,3-d]pyrimidin-7(6H)-one,

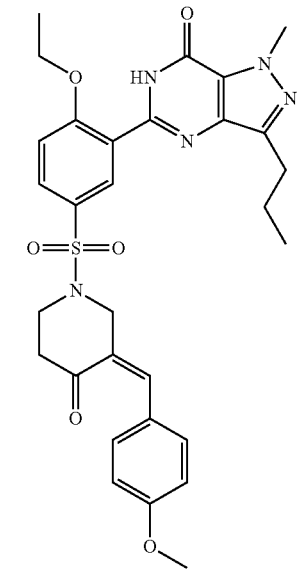 [SMILES: CCCc1nn(C)c2c(=O)[nH]c(-c3cc(S(=O)(=O)N4CCC(=O)/C(=C\c5ccc(OC)cc5)C4)ccc3OCC)nc12]

(Z)-5-(2-ethoxy-5-((3-(4-methoxybenzylidene)-4-oxopiperidin-1-yl)sulfonyl)phenyl)-1-methyl-3-propyl-1H-pyrazolo[4,3-d]pyrimidin-7(6H)-one,

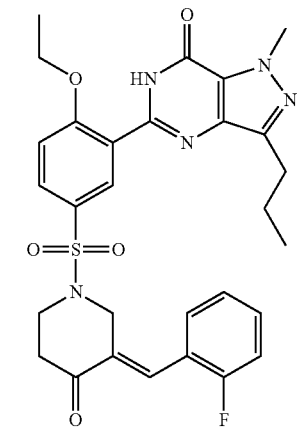 [SMILES: CCCc1nn(C)c2c(=O)[nH]c(-c3cc(S(=O)(=O)N4CCC(=O)/C(=C/c5ccccc5F)C4)ccc3OCC)nc12]

(E)-5-(2-ethoxy-5-((3-(2-fluorobenzylidene)-4-oxopiperidin-1-yl)sulfonyl)phenyl)-1-methyl-3-propyl-1H-pyrazolo[4,3-d]pyrimidin-7(6H)-one,

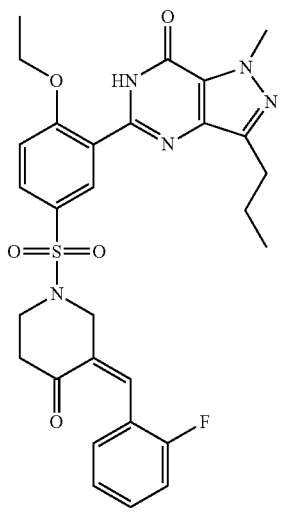 [SMILES: CCCc1nn(C)c2c(=O)[nH]c(-c3cc(S(=O)(=O)N4CCC(=O)/C(=C\c5ccccc5F)C4)ccc3OCC)nc12]

(Z)-5-(2-ethoxy-5-((3-(2-fluorobenzylidene)-4-oxopiperidin-1-yl)sulfonyl)phenyl)-1-methyl-3-propyl-1H-pyrazolo[4,3-d]pyrimidin-7(6H)-one,

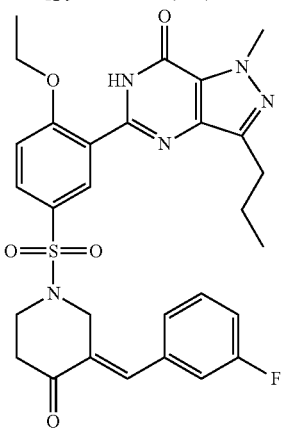

(E)-5-(2-ethoxy-5-((3-(3-fluorobenzylidene)-4-oxopiperidin-1-yl)sulfonyl)phenyl)-1-methyl-3-propyl-1H-pyrazolo[4,3-d]pyrimidin-7(6H)-one,

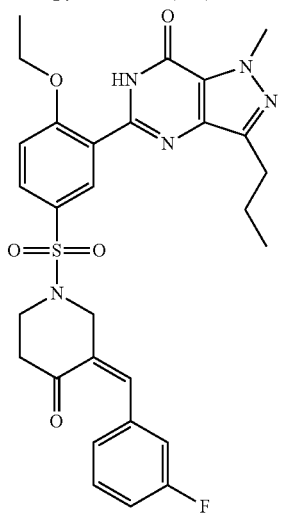

(Z)-5-(2-ethoxy-5-((3-(3-fluorobenzylidene)-4-oxopiperidin-1-yl)sulfonyl)phenyl)-1-methyl-3-propyl-1H-pyrazolo[4,3-d]pyrimidin-7(6H)-one,

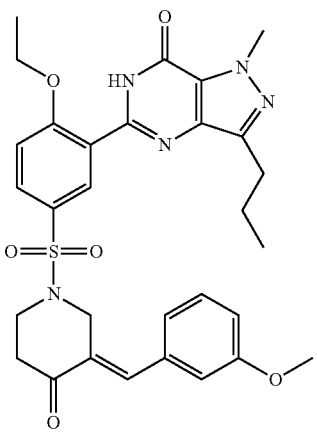 [SMILES: CCCc1nn(C)c2c(=O)[nH]c(-c3cc(S(=O)(=O)N4CCC(=O)/C(=C/c5cccc(OC)c5)C4)ccc3OCC)nc12]

(E)-5-(2-ethoxy-5-((-3-(3-methoxybenzylidene)-4-oxopiperidin-1-yl) sulfonyl)phenyl)-1-methyl-3-propyl-1H-pyrazolo[4,3-d]pyrimidin-7(6H)-one,

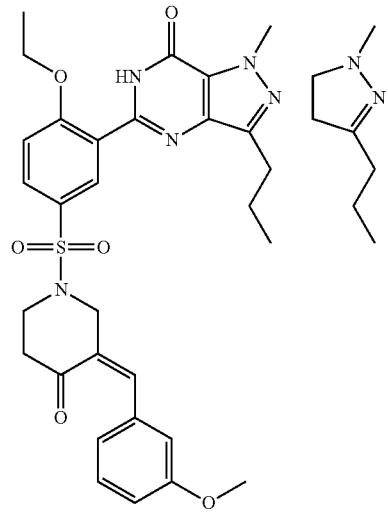

(Z)-5-(2-ethoxy-5-((3-(3-methoxybenzylidene)-4-oxopiperidin-1-yl)sulfonyl)phenyl)-1-methyl-3-propyl-1H-pyrazolo[4,3-d]pyrimidin-7(6H)-one,

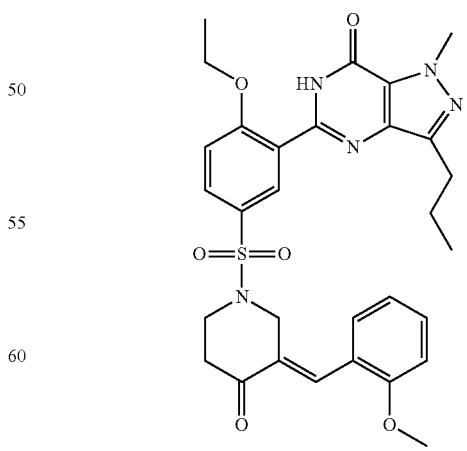

(E)-5-(2-ethoxy-5-((3-(2-methoxybenzylidene)-4-oxopiperidin-1-yl)sulfonyl)phenyl)-1-methyl-3-propyl-1H-pyrazolo[4,3-d]pyrimidin-7(6H)-one,

61

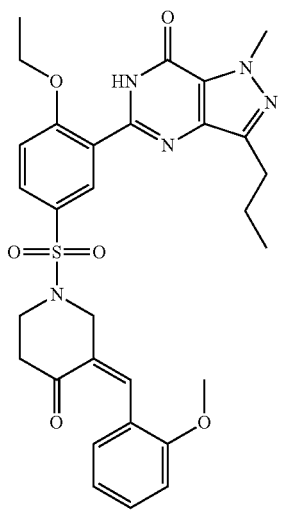 [SMILES: CCCc1nn(C)c2c(=O)[nH]c(-c3cc(S(=O)(=O)N4CCC(=O)/C(=C\c5ccccc5OC)C4)ccc3OCC)nc12]

(Z)-5-(2-ethoxy-5-((3-(2-methoxybenzylidene)-4-oxopiperidin-1-yl)sulfonyl)phenyl)-1-methyl-3-propyl-1H-pyrazolo[4,3-d]pyrimidin-7(6H)-one,

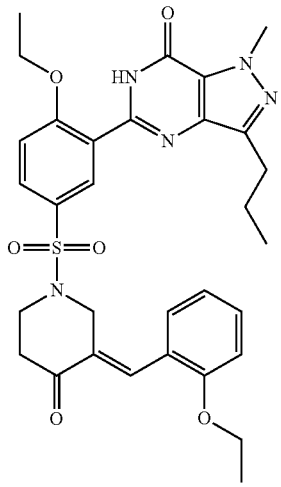 [SMILES: CCCc1nn(C)c2c(=O)[nH]c(-c3cc(S(=O)(=O)N4CCC(=O)/C(=C/c5ccccc5OCC)C4)ccc3OCC)nc12]

(E)-5-(2-ethoxy-5-((3-(2-ethoxybenzylidene)-4-oxopiperidin-1-yl)sulfonyl)phenyl)-1-methyl-3-propyl-1H-pyrazolo[4,3-d]pyrimidin-7(6H)-one,

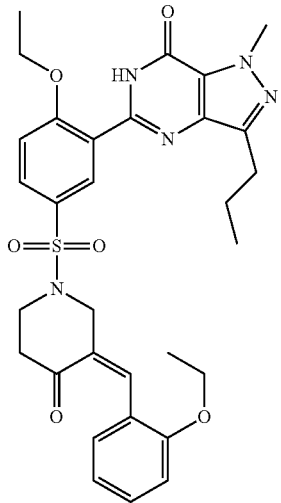 [SMILES: CCCc1nn(C)c2c(=O)[nH]c(-c3cc(S(=O)(=O)N4CCC(=O)/C(=C\c5ccccc5OCC)C4)ccc3OCC)nc12]

(Z)-5-(2-ethoxy-5-((3-(2-ethoxybenzylidene)-4-oxopiperidin-1-yl)sulfonyl)phenyl)-1-methyl-3-propyl-1H-pyrazolo[4,3-d]pyrimidin-7(6H)-one,

62

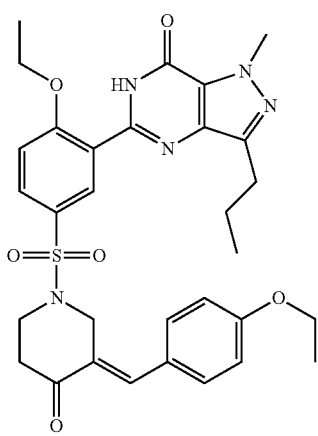 [SMILES: CCCc1nn(C)c2c(=O)[nH]c(-c3cc(S(=O)(=O)N4CCC(=O)/C(=C/c5ccc(OCC)cc5)C4)ccc3OCC)nc12]

(E)-5-(2-ethoxy-5-((3-(4-ethoxybenzylidene)-4-oxopiperidin-1-yl)sulfonyl)phenyl)-1-methyl-3-propyl-1H-pyrazolo[4,3-d]pyrimidin-7(6H)-one,

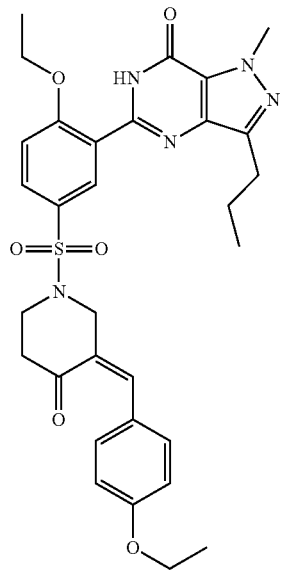 [SMILES: CCCc1nn(C)c2c(=O)[nH]c(-c3cc(S(=O)(=O)N4CCC(=O)/C(=C\c5ccc(OCC)cc5)C4)ccc3OCC)nc12]

(Z)-5-(2-ethoxy-5-((3-(4-ethoxybenzylidene)-4-oxopiperidin-1-yl)sulfonyl)phenyl)-1-methyl-3-propyl-1H-pryazolo[4,3-d]pyrimidin-7(6H)-one,

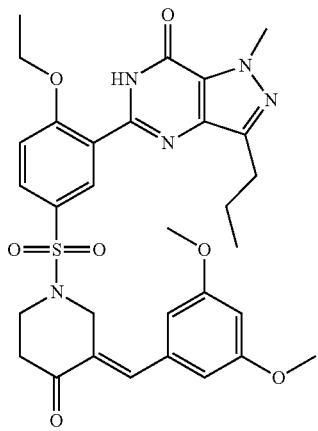 [SMILES: CCCc1nn(C)c2c(=O)[nH]c(-c3cc(S(=O)(=O)N4CCC(=O)/C(=C/c5cc(OC)cc(OC)c5)C4)ccc3OCC)nc12]

(E)-5-(5-((3-(3,5-dimethoxybenzylidene)-4-oxopiperidin-1-yl)sulfonyl)-2-ethoxyphenyl)-1-methyl-3-propyl-1H-pyrazolo[4,3-d]pyrimidin-7(6H)-one,

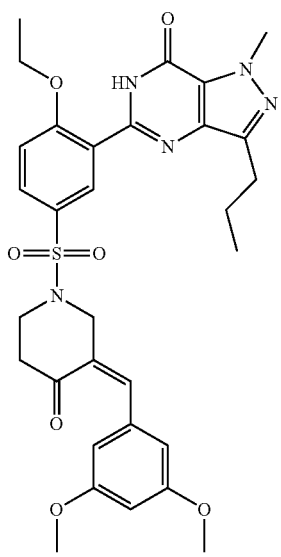 [SMILES: CCCc1nn(C)c2c(=O)[nH]c(-c3cc(S(=O)(=O)N4CCC(=O)/C(=C\c5cc(OC)cc(OC)c5)C4)ccc3OCC)nc12]

(Z)-5-(5-((3-(3,5-dimethoxybenzylidene)-4-oxopiperidin-1-yl)sulfonyl)-2-ethoxyphenyl)-1-methyl-3-propyl-1H-pyrazolo[4,3-d]pyrimidin-7(6H)-one,

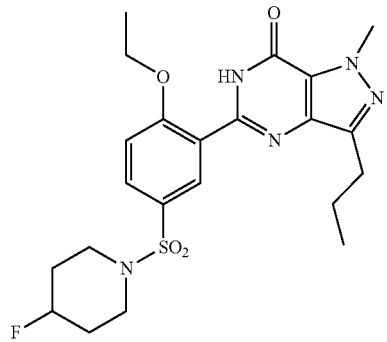 [SMILES: CCCc1nn(C)c2c(=O)[nH]c(-c3cc(S(=O)(=O)N4CCC(F)CC4)ccc3OCC)nc12]

5-(2-ethoxy-5-((4-fluoropiperidin-1-yl)sulfonyl)phenyl)-1-methyl-3-propyl-1H-pyrazolo[4,3-d]pyrimidin-7(6H)-one,

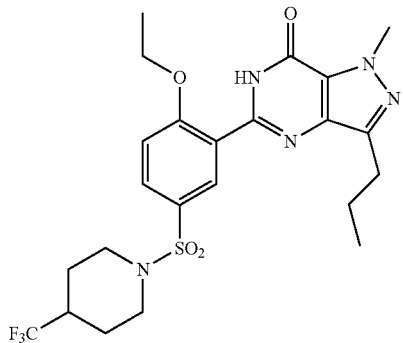 [SMILES: CCCc1nn(C)c2c(=O)[nH]c(-c3cc(S(=O)(=O)N4CCC(C(F)(F)F)CC4)ccc3OCC)nc12]

5-(2-ethoxy-5-((4-(trifluoromethyl)piperidin-1-yl)sulfonyl)phenyl)-1-methyl-3-propyl-1H-pyrazolo[4,3-d]pyrimidin-7(6H)-one.

3. A compound or a pharmaceutically acceptable salt thereof selected from the group consisting of:

5-(2-ethoxy-5-((4-(hydroxymethyl)piperidin-1-yl)sulfonyl) phenyl)-1-methyl-3-propyl-1H-pyrazolo[4,3-d]pyrimidin-7(6H)-one,

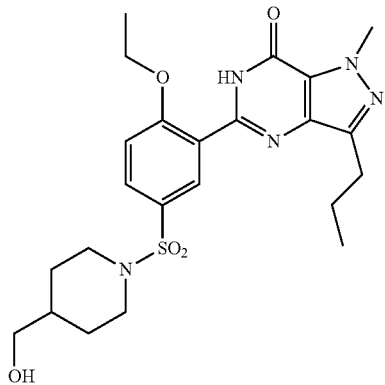 [SMILES: CCCc1nn(C)c2c(=O)[nH]c(-c3cc(S(=O)(=O)N4CCC(CO)CC4)ccc3OCC)nc12]

5-(2-ethoxy-5-((4-(2-hydroxyethyl)piperidin-1-yl)sulfonyl) phenyl)-1-methyl-3-propyl-1H-pyrazolo[4,3-d]pyrimidin-7(6H)-one,

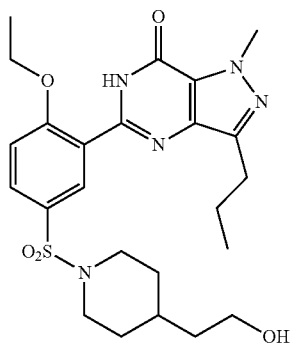 [SMILES: CCCc1nn(C)c2c(=O)[nH]c(-c3cc(S(=O)(=O)N4CCC(CCO)CC4)ccc3OCC)nc12]

5-(2-ethoxy-5-((4-(pyridine-4-yl)piperazin-1-yl)sulfonyl) phenyl)-1-methyl-3-propyl-1H-pyrazolo[4,3-d]pyrimidin-7(6H)-one

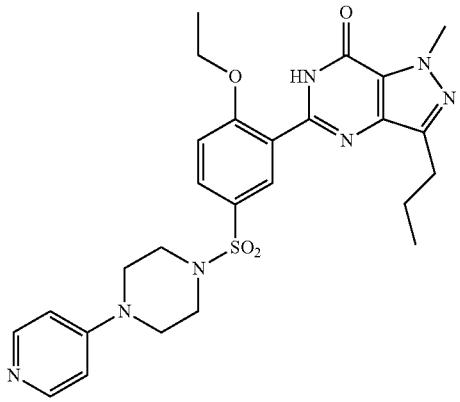 [SMILES: CCCc1nn(C)c2c(=O)[nH]c(-c3cc(S(=O)(=O)N4CCN(c5ccncc5)CC4)ccc3OCC)nc12]

5-(2-ethoxy-5-((4-(pyrimidin-2-yl)piperazin-1-yl)sulfonyl) phenyl)-1-methyl-3-propyl-1H-pyrazolo[4,3-d]pyrimidin-7(6H)-one,

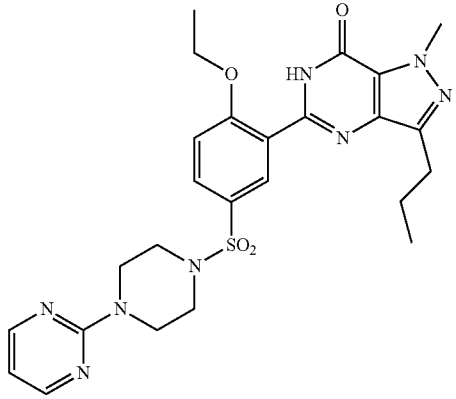 [SMILES: CCCc1nn(C)c2c(=O)[nH]c(-c3cc(S(=O)(=O)N4CCN(c5ncccn5)CC4)ccc3OCC)nc12]

tert-butyl (1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)carbamate,

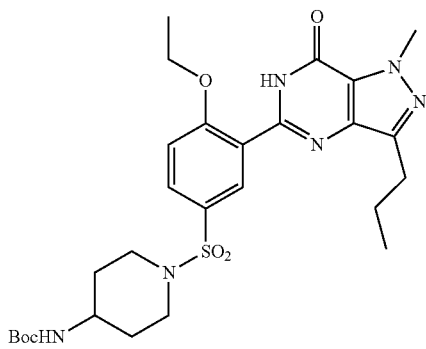 [SMILES: CCCc1nn(C)c2c(=O)[nH]c(-c3cc(S(=O)(=O)N4CCC(NC(=O)OC(C)(C)C)CC4)ccc3OCC)nc12]

5-(5-((4-(aminomethyl)piperidin-1-yl)sulfonyl)-2-ethoxyphenyl)-1-methyl-3-propyl-1H-pyrazolo[4,3-d]pyrimidin-7(6H)-one,

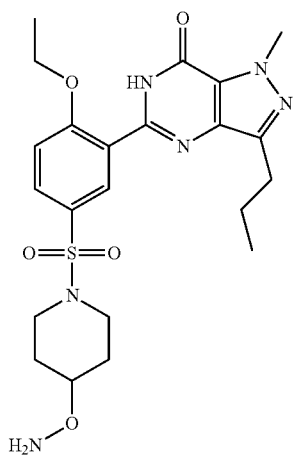 [SMILES: CCCc1nn(C)c2c(=O)[nH]c(-c3cc(S(=O)(=O)N4CCC(ON)CC4)ccc3OCC)nc12]

5-(5-((4-(2-aminoethyl)piperidin-1-yl) sulfonyl)-2-ethoxyphenyl)-1-methyl-3-propyl-1H-pyrazolo[4,3-d]pyrimidin-7(6H)-one,

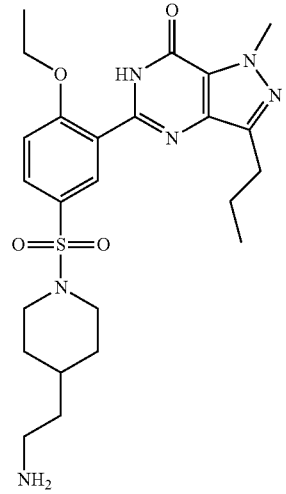 [SMILES: CCCc1nn(C)c2c(=O)[nH]c(-c3cc(S(=O)(=O)N4CCC(CCN)CC4)ccc3OCC)nc12]

5-(2-ethoxy-5-((3-oxopiperazin-1-yl)sulfonyl)phenyl)-1-methyl-3-propyl-1H-pyrazolo[4,3-d]pyrimidin-7 (6H)-one,

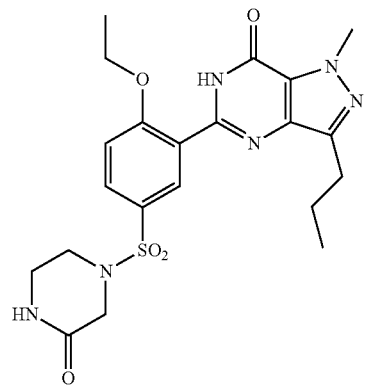 [SMILES: CCCc1nn(C)c2c(=O)[nH]c(-c3cc(S(=O)(=O)N4CCNC(=O)C4)ccc3OCC)nc12]

5-(5-([1,4'-bipiperidin]-1'-ylsulfonyl)-2-ethoxyphenyl)-1-methyl-3-propyl-1H-pyrazolo[4,3-d]pyrimidin-7 (6H)-one,

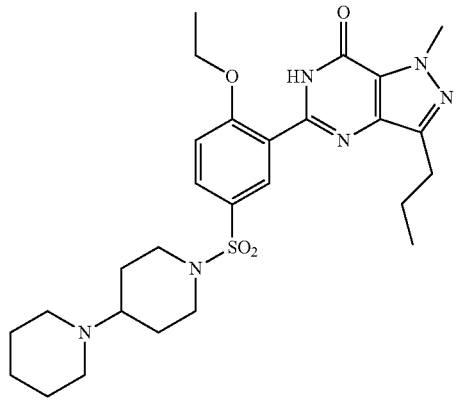 [SMILES: CCCc1nn(C)c2c(=O)[nH]c(-c3cc(S(=O)(=O)N4CCC(N5CCCCC5)CC4)ccc3OCC)nc12]

5-(5-((4-benzylpiperidin-1-yl) sulfonyl)-2-ethoxyphenyl)-1-methyl-3-propyl-1H-pyrazolo[4,3-d]pyrimidin-7 (6H)-one,

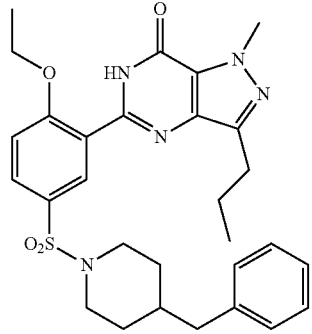 [SMILES: CCCc1nn(C)c2c(=O)[nH]c(-c3cc(S(=O)(=O)N4CCC(Cc5ccccc5)CC4)ccc3OCC)nc12]

5-(2-ethoxy-5-((4-methylpiperidin-1-yl) sulfonyl)phenyl)-1-methyl-3-propyl-1H-pyrazolo[4,3-d]pyrimidin-7 (6H)-one,

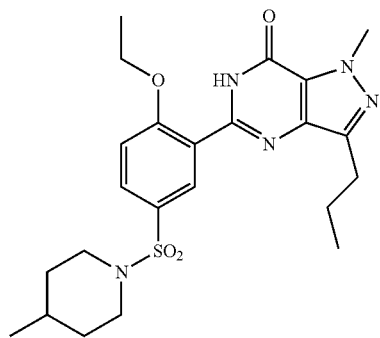 [SMILES: CCCc1nn(C)c2c(=O)[nH]c(-c3cc(S(=O)(=O)N4CCC(C)CC4)ccc3OCC)nc12]

5-(2-ethoxy-5-((4-(pyrrolidin-1-yl)piperidin-1-yl)sulfonyl)phenyl)-1-methyl-3-propyl-1H-pyrazolo[4,3-d]pyrimidin-7(6H)-one,

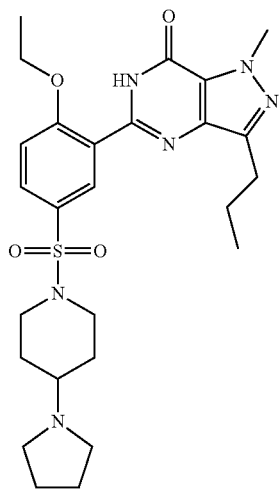 [SMILES: CCCc1nn(C)c2c(=O)[nH]c(-c3cc(S(=O)(=O)N4CCC(N5CCCC5)CC4)ccc3OCC)nc12]

5-(2-ethoxy-5-((4-(pyridine-3-yl)piperazin-1-yl)sulfonyl)phenyl)-1-methyl-3-propyl-1H-pyrazolo[4,3-d]pyrimidin-7(6H)-one,

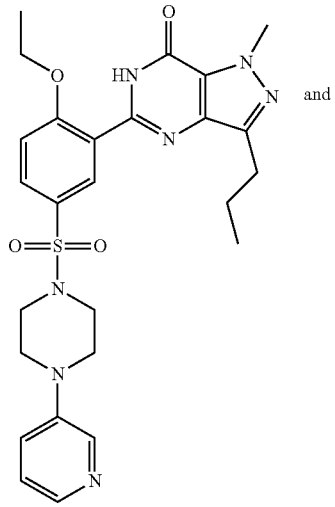 [SMILES: CCCc1nn(C)c2c(=O)[nH]c(-c3cc(S(=O)(=O)N4CCN(c5cccnc5)CC4)ccc3OCC)nc12]

5-(5-((4,4-difluoropiperidin-1-yl)sulfonyl)-2-ethoxyphenyl)-1-methyl-3-propyl-1H-pyrazolo[4,3-d]pyrimidin-7(6H)-one,

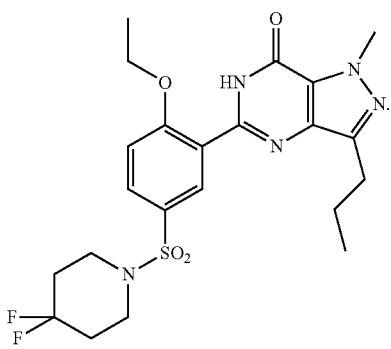 [SMILES: CCCc1nn(C)c2c(=O)[nH]c(-c3cc(S(=O)(=O)N4CCC(F)(F)CC4)ccc3OCC)nc12]

4. A pharmaceutical composition comprising an effective amount of the compound of formula 1A as claimed in claim 1, optionally along with a pharmaceutically acceptable salt, excipient, diluent, and carrier.

5. The pharmaceutical composition as claimed in claim 4, wherein the pharmaceutically acceptable carrier containing aqueous solution is selected from the group consisting of water, buffered saline, glycol, glycerol, olive oil and liposome.

6. The pharmaceutical composition as claimed in claim 4, wherein the dose of compound of formula 1A is between 0.1 mg/kg to 100 mg/kg.

7. A process for the preparation of the compound or a pharmaceutically acceptable salt thereof of the Formula 1A as claimed in claim 1, comprising:
   (i) reacting diethyl oxalate and 2-pentanone to obtain ethyl 3-propyl-1H-pyrazole-5-carboxylate (compound 1);
   (ii) reacting compound e of step (i) with dimethyl sulfate to obtain ethyl 1-methyl-3-propyl-1H-pyrazole-5-carboxylate (compound 2);

(iii) treating compound 2 of step (ii) with NaOH solution to obtain 1-methyl-3-propyl-1H-pyrazole-5-carboxylic acid (compound 3);

(iv) reacting compound 3 of step (iii) with conc. $H_2SO_4$ and nitric acid to obtain 1-methyl-4-nitro-3-propyl-1H-pyrazole-5-carboxylic acid (compound 4);

(v) reacting compound 4 of step (iv) with $SOCl_2$ to obtain 1-methyl-4-nitro-3-propyl-1H-pyrazole-5-carboxamide (compound 5);

(vi) treating compound 5 of step (v) with $EtOH:H_2O$, Fe powder and $NH_4Cl$ to obtain 4-amino-1-methyl-3-propyl-1H-pyrazole-5-carboxamide (compound 6);

Compound 6

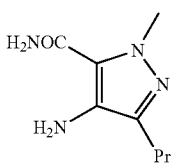

(vii) reacting compound 6 of step (vi) with 2-ethoxybenzaldehyde to obtain 5-(2-ethoxyphenyl)-1-methyl-3-propyl-1H-pyrazolo[4,3-d]pyrimidin-7(6H)-one (compound 7);

(viii) treating compound 7 of step (vii) with chlorosulphonic acid to obtain 4-ethoxy-3-(6,7-dihydro-1-methyl-7-oxo-3-propyl-1H-pyrazolo[4,3-d]pyrimidin-5-yl)benzene-1-sulfonyl chloride (compound 8);

Compound 8

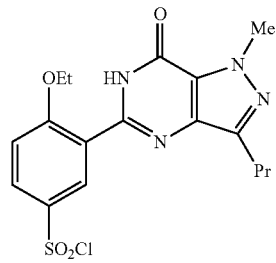

(ix) reacting compound 8 of step (viii), with an amino compound selected from the group consisting of cyclic, acyclic, aliphatic and aromatic amino in the presence of a base in a solvent at a temperature ranging between 10 to 35° C. for a period ranging between 45 min to 4 hrs, adding cold water to quench the reaction and obtaining the compound of formula 1A.

* * * * *

UNITED STATES PATENT AND TRADEMARK OFFICE
CERTIFICATE OF CORRECTION

PATENT NO. : 10,017,511 B2
APPLICATION NO. : 15/115573
DATED : July 10, 2018
INVENTOR(S) : Sanghapal Damodhar Sawant et al.

Page 1 of 1

It is certified that error appears in the above-identified patent and that said Letters Patent is hereby corrected as shown below:

In the Claims

Column 65, Claim 3, Lines 50-65:

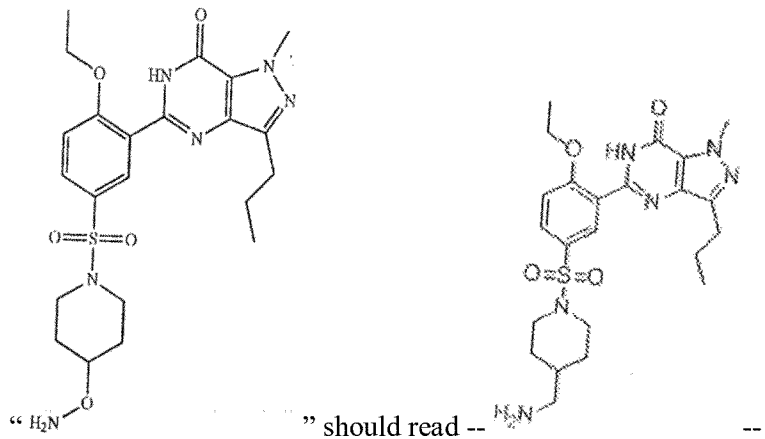

Column 68, Claim 7, Line 65:
"compound e" should read --compound 1--

Signed and Sealed this
Fifth Day of May, 2020

Andrei Iancu
*Director of the United States Patent and Trademark Office*